United States Patent
Zijlstra et al.

(10) Patent No.: US 10,585,102 B2
(45) Date of Patent: Mar. 10, 2020

(54) CHARACTERIZATION OF CANCER USING DETECTION OF ACTIVATED LEUKOCYTE CELL ADHESION MOLECULE (ALCAM) SHEDDING

(71) Applicant: Vanderbilt University, Nashville, TN (US)

(72) Inventors: Andries Zijlstra, Nashville, TN (US); Amanda G. Hansen, Nashville, TN (US); Shanna Arnold, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 55 days.

(21) Appl. No.: 14/433,519

(22) PCT Filed: Oct. 11, 2013

(86) PCT No.: PCT/US2013/064696
§ 371 (c)(1),
(2) Date: Apr. 3, 2015

(87) PCT Pub. No.: WO2014/059372
PCT Pub. Date: Apr. 17, 2014

(65) Prior Publication Data
US 2015/0253331 A1 Sep. 10, 2015

Related U.S. Application Data

(60) Provisional application No. 61/712,556, filed on Oct. 11, 2012.

(51) Int. Cl.
*G01N 33/53* (2006.01)
*G01N 33/574* (2006.01)

(52) U.S. Cl.
CPC . *G01N 33/57488* (2013.01); *G01N 33/57407* (2013.01); *G01N 33/57419* (2013.01); *G01N 33/57438* (2013.01); *G01N 2333/70503* (2013.01)

(58) Field of Classification Search
CPC .. G01N 33/48; G01N 33/483; G01N 33/4833; G01N 33/487; G01N 33/50; G01N 33/5008; G01N 33/5091; G01N 33/53; G01N 33/574; G01N 33/577; G01N 33/68; G01N 33/6842; C07K 14/705; C07K 14/70503
See application file for complete search history.

(56) References Cited

U.S. PATENT DOCUMENTS

2011/0151580 A1* 6/2011 Diamandis ....... G01N 33/57415
436/501

OTHER PUBLICATIONS

Wu, A.H.B., Clinica Chimica Acta, 369: 119-124, 2006.*
Micciche, F. et al., PLoS One, 6(2): pp. 1-9, Feb. 2001.*
Ni, C., et al., PLoS One, 8(8): 1-8, 2013.*
Kristiansen, G., et al., The Prostate, 54: 34-43, 2003.*
Weichert, W., J. Clin. Pathol., 57: 1160-1164, 2004.*
Rosso, O., et al., Mol. Cancer Res., 5(12): 1246-1253, 2007.*
Van Kilsdonk, J.W.J., et al, European Journal of Cell biology, 89: 415-427, 2010.*
Thongboonkerd, V., et al., Kidney international, 62: 1461-1469, 2002.*
Tomita, K., et al., UroOncology, 3(3-4): 121-129, 2003.*
R&D Systems information on clone #105902, downloaded Jan. 19, 2017 from www.rndsystems.com/products/human-alcam-cd166-antibody-105902_mab6561.*
Van Kempen, L.C.L.T., et al., The Journal of Biological Chemistry, 276(28): 25783-25790, 2001.*
Ofori-Acquah, Translational Research 151(3): 122-128, 2008.*
Egloff, S.A., et al., Oncotarget, 8(1): 722-741, 2017.*
Witzel I, Schröder C, Müller V, Zander H, Tachezy M, Ihnen M, et al. Detection of Activated Leukocyte Cell Adhesion Molecule in the Serum of Breast Cancer Patients and Implications for Prognosis. Oncology. 2012;82(6):305-312.
Micciché F, Da Riva L, Fabbi M, Pilotti S, Mondellini P, Ferrini S, et al. Activated leukocyte cell adhesion molecule expression and shedding in thyroid tumors. PLoS ONE. 2011;6(2):e17141.
Ihnen M, Müller V, Wirtz RM, Schröder C, Krenkel S, Witzel I, et al. Predictive impact of activated leukocyte cell adhesion molecule (ALCAM/CD166) in breast cancer. Breast Cancer Res Treat. 2008;112(3):419-427.
Carbotti G, Orengo AM, Mezzanzanica D, et al. Activated leukocyte cell adhesion molecule soluble form: a potential biomarker of epithelial ovarian cancer is increased in type II tumors. Int. J. Cancer 2012.
Ihnen M, Kress K, Kersten JF, et al. Relevance of activated leukocyte cell adhesion molecule (ALCAM) in tumor tissue and sera of cervical cancer patients. BMC Cancer 2012;12:140.
Tachezy M, Zander H, Marx AH, et al. ALCAM (CD166) expression and serum levels in pancreatic cancer. PLoS ONE 2012;7(6):e39018.
Tachezy M, Effenberger K, Zander H, et al. ALCAM (CD166) expression and serum levels are markers for poor survival of esophageal cancer patients. Int. J. Cancer 2012;131(2):396-405.
Hansen, A. G., Freeman, T. J., Arnold, S. A., Starchenko, A., jones-paris, C. R., Gilger, M. A., Washington, M. K., Fan, K.-H., Shyr, Y., Beauchamp, R. D., et al. (2013). Elevated ALCAM Shedding in Colorectal Cancer Correlates with Poor Patient Outcome. Cancer Res 73, 2955-2964.
Hansen, Amanda G. et al. "ALCAM/CD166 Is a TGFβ Responsive Marker and Functional Regulator of Prostate Cancer Metastasis to Bone." Cancer research74.5 (2014): 1404-1415. PMC. Web. Apr. 27, 2015.

* cited by examiner

Primary Examiner — Mark Halvorson
(74) Attorney, Agent, or Firm — Stites & Harbison PLLC; Mandy Wilson Decker; Sean P. Ritchie

(57) ABSTRACT

The presently-disclosed subject matter includes labels for use in the identification of shed ALCAM in s sample from a subject. Further included are methods for characterizing, monitoring, evaluating treatment efficacy, or evaluating the progression of cancer in a subject that comprise providing a biological sample from the subject, determining the presence or amount of shed ALCAM in the biological sample, and then comparing the presence or the amount of the shed ALCAM to a reference. Differences between the presence or amount of shed ALCAM relative to the reference can be used to diagnose, prognosticate, treat, monitor, or otherwise characterize a cancer in a subject. Further provided are kits comprising a reagent and/or antibody for diagnosing, prognosticating, monitoring, or otherwise characterizing a cancer in a subject.

3 Claims, 48 Drawing Sheets

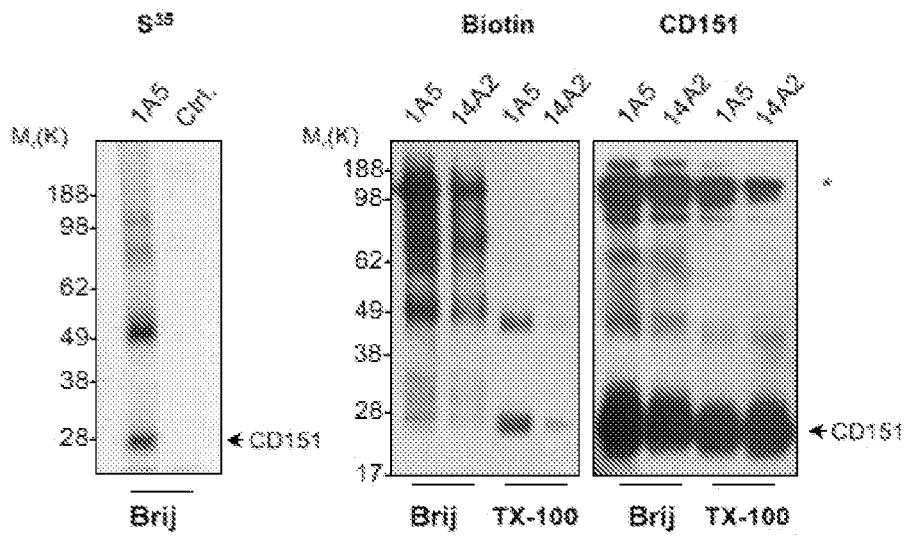
Figure 16B
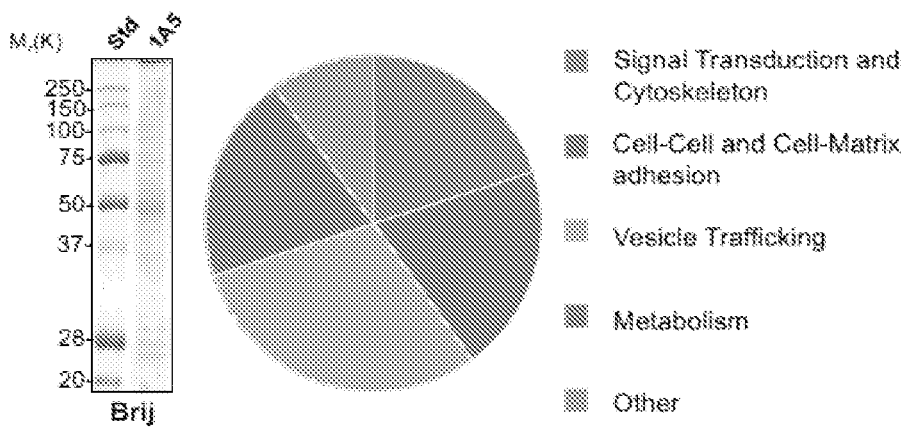
Figure 16C
Targets Identified by Mass Spectrometry.
| Established Partners | Gene # | Uniprot ID | Ref. |
|---|---|---|
| CD151 (TSPAN24) | 977 | P48509 | |
| Integrin subunit α3 (ITGA3) | 3672 | P26006 | |
| Integrin subunit β1 (ITGB1) | 3688 | P05556 | |
| MMP14 (MT1-MMP) | 4323 | P50281 | |
| PI 4-kinase type 2-alpha (PIK42A) | 55361 | Q9BTU6 | |
| Putative Partners | | |
| ALCAM (CD166) | 214 | Q13740 | |
| CUB domain-containing protein-1 | 64866 | Q9H5V8 | |
| Claudin domain-containing protein-1 | 56650 | Q9NY35 | |
| EGF-like repeat and discoidin I-like | 10085 | O43854 | |
| CD44 antigen precursor | 960 | P16070 | |
Figure 16D

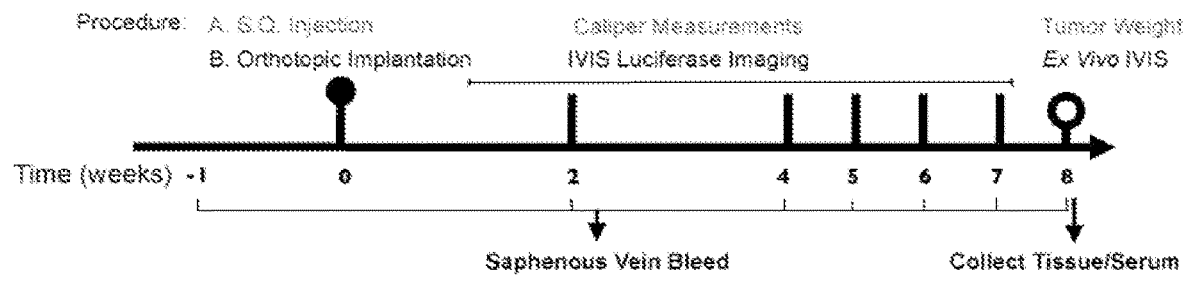
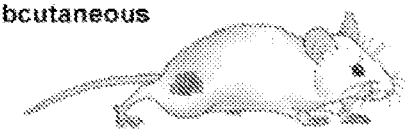 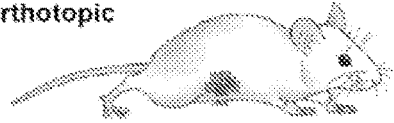
Figure 24A
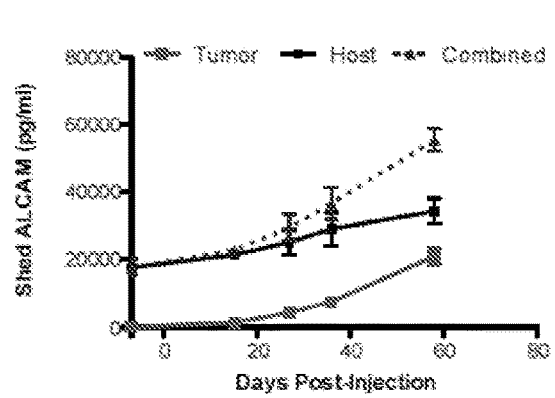 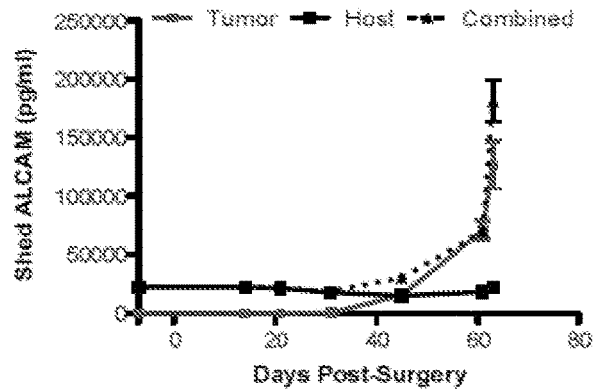
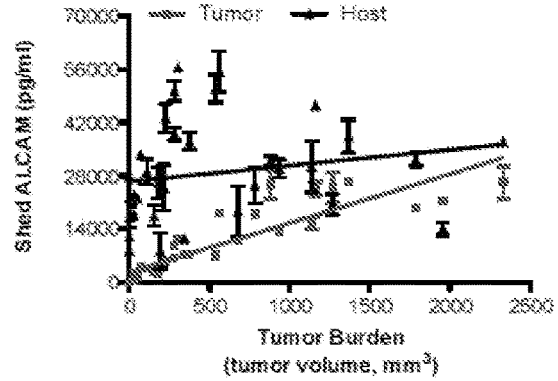 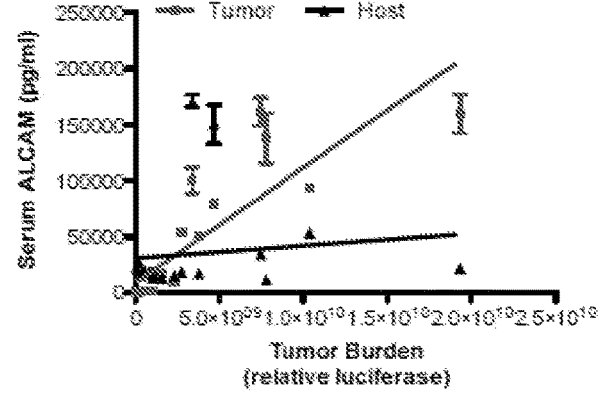
Figure 24B  Figure 24C Serum TNF-alpha post-1hr. LPS

CHARACTERIZATION OF CANCER USING DETECTION OF ACTIVATED LEUKOCYTE CELL ADHESION MOLECULE (ALCAM) SHEDDING

RELATED APPLICATIONS

This application claims priority from U.S. Provisional Application Ser. No. 61/712,556, filed Oct. 11, 2012, the entire disclosure of which is incorporated herein by this reference.

GOVERNMENT INTEREST

This invention was made with government support under grant numbers CA120711-01, CA143081-01, CA143081-03, CA040035, CA9060625, UL1TR000445, CA136228, CA009592, CA098131, CA136228, HL007751, and DK079341 awarded by the National Institutes of Health. The government has certain rights in the invention.

TECHNICAL FIELD

The presently-disclosed subject matter relates to characterization of cancer using detection of activated leukocyte cell adhesion molecule (ALCAM) shedding. Characterization includes monitoring a cancer, providing a diagnosis, providing a prognosis, providing a theranosis, and evaluation treatment efficacy and/or progression of a cancer in a subject by determining a presence or an amount of shed ALCAM in a biological sample from the subject.

INTRODUCTION

Cancer treatment is currently hindered in large part because of poor diagnostic, prognostic, and monitoring systems and methods. For example, colorectal cancer (CRC) is the third most frequently diagnosed cancer, and second leading cause of cancer-related deaths in the United States. Current prognosis for CRC patients predominantly rely on pathologic UICC/AJCC tumor node metastasis (TNM) staging classification. Although TNM staging successfully stratifies high-risk patients, there is significant variability in the rate of disease progression within each stage. Particular concern exists for early stage disease (Stage I and II) where patients can progress more rapidly than expected. It is well known that approximately 30% of stage II CRC patients die of recurrent and metastatic disease. Identification of patients at risk of recurrence/progression could inform clinicians on adjuvant chemotherapeutic treatment decisions.

Furthermore, bladder cancer (BCa) is another example of a widespread cancer, and BCa is the fourth most common cancer in men in the United States with an estimated 55,600 new cases in 2012 and a five-year relative survival of 71%, 35% and 5% for local, regional and distant disease, respectively. Within 5 years of initial diagnosis, 60-70% of patients with non-muscle invasive BCa will recur locally after transurethral resection and another 20-50% will progress to invasive disease, ultimately requiring complete surgical resection of the bladder (cystectomy). Moreover, approximately 50% of patients undergoing radical cystectomy will recur with metastases within two years. The risk of progression and recurrence necessitates frequent follow-up, invasive monitoring, and repeated clinical interventions which decreases quality of life and makes lifelong management of BCa more costly than any other cancer. Furthermore, despite proven survival benefit, neoadjuvant chemotherapy is underutilized due to an inability to accurately predict recurrence and monitor treatment response that would justify the risk of exposure of an aging patient population with multiple comorbidities to chemotherapy-associated toxicities.

These observations highlight the need for prognostic indicators that identify patients likely to benefit from aggressive intervention. Biomarkers can assist in identifying those patients that require more aggressive intervention or patients at risk of relapse after initial treatment. Promising clinical tests including ONCOTYPE DX™ and COLOPRINT™ evaluate possible disease progression by assessing gene expression. These tests are not yet widely applied possibly because their epigenetic evaluation reflects on gene expression which does not always reliably predict actual cellular behavior. Thus, existing prognostic tests do not report on cancer progression. Furthermore, the heterogeneous nature of genetic drivers, particularly in BCa, limits their use as predicative biomarkers.

Accordingly, clinical intervention would greatly benefit from further understanding of the molecular mechanisms that drive metastasis as well as molecular indicators that identify patients at risk of disease progression. There remains a need in the art for a methods and compositions for diagnosing, prognosticating, and monitoring the progression of certain cancers.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes a shed ALCAM label for use in the identification of shed ALCAM in a sample from a subject. The label can include an antibody, which itself can be an isolated antibody. The label can produce a signal which can be detected, such as an optical signal or the like. In some embodiments the optical signal can include fluorescence. In this regard, in some embodiments the label comprises an antibody and a signal-producing moiety conjugated to the antibody. The antibody can selectively bind to shed ALCAM, whereas the signal-producing moiety can produce a signal that can be detected (e.g., fluoresce).

In some embodiments the label can recognize the C-terminal of ALCAM, shed ALCAM, or a combination thereof. In other embodiments the label can recognize the N-terminal ALCAM, shed ALCAM, or a combination thereof. In some embodiments the label is detectable with the use of ELSIA.

The presently-disclosed subject matter also includes a method for characterizing, monitoring, or characterizing and monitoring a cancer in a subject. In some embodiments the methods comprise providing a biological sample from the subject, determining a presence or an amount of shed ALCAM in the biological sample, and comparing the presence or the amount of the shed ALCAM in the biological sample to a reference, wherein the cancer is characterized and/or monitored based on a measurable difference in the presence or the amount of the shed ALCAM from the biological sample as compared to the reference. In different implementations, the step of characterizing can include providing a diagnosis, prognosis, theranosis, or combination thereof of the cancer.

In yet other embodiments a method is provided for evaluating the treatment efficacy, progression, or both of a cancer in a subject. In some embodiments the methods comprise providing a biological sample from the subject, determining a presence or an amount of shed ALCAM in the biological sample, and comparing the presence or the amount of the shed ALCAM to a reference, wherein the treatment efficacy and/or progression of the cancer is evaluated based on a measurable difference in the presence or the amount of the shed ALCAM as compared to the reference.

In the present methods there can be provided a step of contacting the biological sample with an antibody that selectively binds shed ALCAM. In this regard, some embodied antibodies can recognize the C-terminal ALCAM, shed ALCAM, or a combination thereof, or they can recognize the N-terminal ALCAM, shed ALCAM, or a combination thereof. In some embodiments the step of determining a presence or an amount of shed ALCAM in the biological sample therefore includes the use of an ELISA.

In the present methods the cancer can include, but is not limited to, a precancerous or cancerous pathology selected from the group consisting of urogenital cancer, bladder cancer, renal cell cancer, colorectal cancer, and combinations thereof. Thus, in some embodiments the cancer is urogenital cancer. In some embodiments the cancer is bladder cancer. In some embodiments the cancer is renal cell cancer. In some embodiments the cancer is colorectal cancer.

As described above, the present methods can include comparing the presence or the amount of shed ALCAM to a reference. In some embodiments the reference comprises a level of the shed ALCAM in one or more samples from one or more individuals without the cancer. In some embodiments the reference comprises a level of the shed ALCAM in a sample from the subject taken over a time course. In some embodiments the reference comprises a sample from the subject collected prior to initiation of treatment for the cancer and/or onset of the cancer and the biological sample is collected after initiation of the treatment or onset of the cancer. In some embodiments the reference comprises a standard sample, control data, or both. The reference can also include any value calculated from one or more different possible references.

In further embodiments, the present methods comprise providing a series of biological samples collected from the subject over a time course, and then determining a presence or an amount of shed ALCAM in each of the series of biological samples. In some embodiments wherein the series of biological samples comprises a first biological sample collected prior to initiation of treatment for the cancer and/or onset of the cancer and a second biological sample collected after initiation of the treatment or onset of the cancer.

In some embodiments the biological sample comprises tissue, urine, serum, blood, spinal fluid, or the like or combinations thereof. In some embodiments the step of providing the biological sample from the subject comprises extracting the sample. Furthermore, in some embodiments the step of providing the biological sample from the subject comprises isolating the shed ALCAM from the sample.

In some embodiments the methods can be carried out in vitro or in vivo. In certain embodiments of the present methods there is further provided a step of determining an amount of intact ALCAM, and, optionally, in some embodiments the methods comprise calculating a ratio of intact ALCAM to shed ALCAM. In yet other embodiments of the present methods there is provided a step of selecting a treatment or modifying a treatment for the cancer based on the amount of the shed ALCAM determined. In some embodied methods a reagent is used.

Additionally, the presently-disclosed subject matter includes a kit that comprises a reagent that can carry out any of the presently-disclosed methods. In some embodiments the kit can further comprise an antibody that selectively binds shed ALCAM. In certain embodiments the antibody recognizes the C-terminal of ALCAM, and in other embodiments the antibody recognizes the N-terminal of ALCAM.

Embodiments of kits can further comprise a reference standard sample and/or control data. The standard sample, the control data, or both can be for a cancer, a non-cancer, or a combination thereof. The cancer can include, but is not limited to, a precancerous or cancerous pathology selected from the group consisting of urogenital cancer, bladder cancer, renal cell cancer, and colorectal cancer.

Further features and advantages of the present presently-disclosed subject matter will become evident to those of ordinary skill in the art after a study of the present application.

BRIEF DESCRIPTION OF THE DRAWINGS

FIG. 24 shows that ALCAM shedding correlates with tumor burden. (A) Schematic representation of in vivo strategy for S.Q. and orthotopic tumor models. B and C) Circulating levels of soluble host and tumor-derived ALCAM detectable in mice bearing subcutaneous injected PC3 cells (B) or PC3 cells orthotopically implanted into the prostate (C). Levels of ALCAM are shown as a function of time (top) or tumor burden at the time of experiment completion (bottom). Each point reflects mean of duplicate measurements±SD.

DESCRIPTION OF EXEMPLARY EMBODIMENTS

Figure 1A:
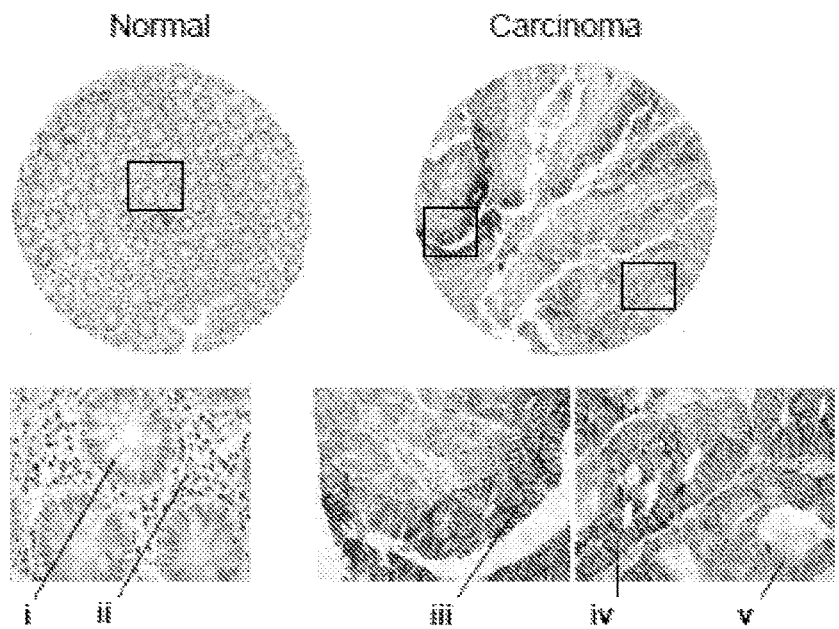
FIG. 1 shows ALCAM expression in colorectal carcinoma and its correlation to patient outcome. A) Representative immunohistochemical staining for ALCAM in normal and tumor colon sections using an antibody directed to the extracellular domain of ALCAM (HPA010926). B) Expression of ALCAM in CRC cell lines evaluated by immunoblotting (left) and microarray analysis (right, GDS1761). Expression (mRNA) of ALCAM (C) and ADAM17 (D) in a cohort of 250 colorectal cancer patients was correlated to patient survival after dichotomizing the population across its mean expression into patients with "High ALCAM" and "Low ALCAM". E) Using an ALCAM sandwich ELISA, circulating levels of shed ALCAM were evaluated in serum from cancer-free patients (n=48) and compared to serum from CRC patients at time of diagnosis (pre-op, n=42) and serum from patient at time of followup after treatment (post-op, n=19). F) CRC patients were stratified according to stage (I-IV) and compared to cancer-free patients (n=48) and healthy adults (n=6). Box plots show the mean, standard deviation and full range of the expression data. Survival is presented with Kaplan-Meier plots and log-rank test was used to evaluate significance.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter meets some or all of the above-identified needs, as will become evident to those of ordinary skill in the art after a study of information provided in this document. To avoid excessive repetition, this Description does not list or suggest all possible combinations of such features.

The presently-disclosed subject matter includes methods of characterizing a cancer using detection of activated leukocyte cell adhesion molecule (ALCAM) shedding. Characterization includes monitoring a cancer, providing a diagnosis, providing a prognosis, providing a theranosis, and evaluation treatment efficacy and/or progression of a cancer in a subject by determining a presence or an amount of shed ALCAM in a biological sample from the subject.

ALCAM (Activated Leukocyte Cell Adhesion Molecule) is a cell-cell adhesion protein that has been identified in a broad array of biological processes including inflammatory responses, neuronal outgrowth, and migration and metastasis. ALCAM consists of five extracellular IgG-like domains, a transmembrane domain and a short cytoplasmic domain. ALCAM can be proteolytically processed by ADAM17, thereby generating a soluble ALCAM component and a truncated membrane-bound ALCAM containing the transmembrane and cytoplasmic domain. At the clinical level, shed ALCAM is detectable in the serum or other biological samples of cancer patients. The present inventors have found that cell adhesion is disrupted when the ectodomain of ALCAM is shed from malignant tumor cells during invasive transformation by ADAM17-mediated cleavage. Consequently, ALCAM shedding is a molecular indicator of a cellular activity, and can present itself pathologically in invasive and/or disseminated diseases.

Unlike most candidate biomarkers, ALCAM expression is not tissue-restricted and it is commonly found in most epithelia and related carcinomas. ALCAM contributes to tumor progression by controlling migration. The present inventors have found that the molecular activity of ALCAM appears to be regulated through shedding of its extracellular domain. Consequently, certain advanced disease tissues express ALCAM but exhibit an elevated level of ALCAM shedding.

In some embodiments, a method for characterizing and/or monitoring a cancer in a subject includes providing a biological sample from the subject; determining a presence or an amount of shed ALCAM in the biological sample; and comparing the presence or the amount of the shed ALCAM in the biological sample to a reference, wherein the cancer is characterized and/or monitored based on a measurable difference in the presence or the amount of the shed ALCAM from the biological sample as compared to the reference.

In some embodiments, the presently-disclosed subject matter includes a method for evaluating treatment efficacy and/or progression of a cancer in a subject, which involves providing a biological sample from the subject; determining a presence or an amount of shed ALCAM in the biological sample; and comparing the presence or the amount of the shed ALCAM to a reference, wherein the treatment efficacy and/or progression of the cancer is evaluated based on a measurable difference in the presence or the amount of the shed ALCAM as compared to the reference.

The presently-disclosed subject matter includes antibodies and kits useful for characterizing, monitoring, evaluating treatment efficacy of, and/or evaluating progression of a cancer in a subject. In some embodiments, the antibody is an isolated antibody or antigen-binding fragment thereof that specifically binds to at least one of C-terminus of shed ALCAM and N-terminus of shed ALCAM. In some embodiments, the kit includes an antibody that selectively binds shed ALCAM. In some embodiments, the kit further includes a reference.

The term "characterizing" and "characterize" are used herein to refer to providing a diagnosis, a prognosis, and/or a theranosis of a cancer. The terms "diagnosing" and "diagnosis" as used herein refer to methods by which the skilled artisan can estimate and even determine whether or not a subject is suffering from a given disease or condition. The skilled artisan often makes a diagnosis on the basis of one or more diagnostic indicators, such as for example a biomarker, the amount (including presence or absence) of which is indicative of the presence, severity, or absence of the condition.

Along with diagnosis, clinical cancer prognosis is also an area of great concern and interest. It is important to know the aggressiveness of the cancer cells and the likelihood of tumor recurrence in order to plan the most effective therapy. If a more accurate prognosis can be made or even a potential risk for developing the cancer assessed, appropriate therapy, and in some instances less severe therapy for the patient can be chosen. Measurement of shed ALCAM can be useful in order to separate subjects with good prognosis and/or low risk of developing cancer who will need no therapy or limited therapy from those more likely to develop cancer or suffer a recurrence of cancer who might benefit from more intensive treatments.

As such, "making a diagnosis" or "diagnosing", as used herein, is further inclusive of determining a risk of developing cancer or determining a prognosis, which can provide for predicting a clinical outcome (with or without medical treatment), selecting an appropriate treatment (or whether treatment would be effective), or monitoring a current treatment and potentially changing the treatment, based on the measure of the shed ALCAM disclosed herein. Diagnostic testing that involves treatment, such as treatment monitoring or decision making can be referred to as "theranosis." Further, in some embodiments of the presently disclosed subject matter, multiple determinations of the shed ALCAM over time can be made to facilitate diagnosis and/or prognosis. A temporal change in the biomarker can be used to predict a clinical outcome, monitor the progression of the cancer and/or efficacy of appropriate therapies directed against the cancer. In such an embodiment, for example, one might expect to see a decrease and/or an increase in the amount of shed ALCAM in a biological sample over time during the course of effective therapy.

As used here, the term "shed ALCAM" refers to shedding of the cell adhesion molecule ALCAM, that is to say, ALCAM that has been shed into a biological sample. As will be known to one of ordinary skill in the art, shed ALCAM is distinct from ALCAM that might be expressed and detected by measuring gene products, such as mRNA or expressed protein, i.e., intact ALCAM. In some embodiments, it can be useful to further detect intact ALCAM, and to determine a ratio of intact ALCAM to shed ALCAM, which can be useful in characterizing the cancer. As such, when "determining a presence or an amount of shed ALCAM" is described herein, it is inclusive of "determining a ratio of intact ALCAM to shed ALCAM," and unless otherwise apparent, reference to "shed ALCAM" is inclusive of "a ratio of intact ALCAM to shed ALCAM."

The presently disclosed subject matter further provides in some embodiments a method for determining whether to initiate or continue treatment of a cancer in a subject and/or a method for evaluating treatment efficacy and/or progression of a cancer in a subject. As used herein, the terms "treatment" or "treating" relate to any treatment of a condition of interest, including but not limited to prophylactic treatment and therapeutic treatment.

The terms "correlated" and "correlating," as used herein in reference to the use of detection of shed ALCAM as disclosed herein, refers to comparing the presence or quantity of the shed ALCAM in a subject to its presence or quantity in subjects known to suffer from, or known to be at risk of, a given condition (e.g., a particular cancer); or in subjects known to be free of a given condition, i.e. "normal subjects" or "control subjects". For example, a level of shed ALCAM disclosed herein in a biological sample can be compared to a shed ALCAM level determined to be associated with a specific type of cancer. The sample's biomarker level is said to have been correlated with a diagnosis; that is, the skilled artisan can use the biomarker level to determine whether the subject suffers from a specific type of cancer, and respond accordingly. Alternatively, the sample's biomarker level can be compared to a control level of the shed ALCAM known to be associated with a good outcome (e.g., the absence of cancer), such as an average level found in a population of normal subjects.

As used herein the term "cancer" can refer to a precancerous or cancerous pathology. In some embodiments the cancer is selected from the group consisting of carcinoma, lymphoma, blastoma, sarcoma and leukemia. The term cancer is also inclusive of other known cancers, including, but not limited to, squamous cell cancer, lung cancer, cancer of the peritoneum, hepatocellular cancer, gastric or stomach cancer, gastrointestinal cancer, urogenital cancer. pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma, head and neck cancer, and lymphoma.

In some embodiments, the reference can be a level of the shed ALCAM in a sample from the subject taken over a time course. In some embodiments, the reference can be a sample from the subject collected prior to initiation of treatment for the cancer and/or onset of the cancer and the biological sample can be collected after initiation of the treatment or onset of the cancer. In some embodiments, the reference can be a standard sample. In some embodiments, the reference can include control data. Thus, the terms "reference" or "control level" are used herein to refer to any presence and/or amount of the shed ALCAM to which the presence and/or amount of shed ALCAM in the biological sample is being compared.

In certain embodiments, shed ALCAM is correlated to a condition or disease by merely its presence or absence. In other embodiments, a threshold level of shed ALCAM can be established (e.g., a particular amount of shed ALCAM), and the level of the indicator in a subject sample can simply be compared to the threshold level.

The phrase "determining the prognosis" as used herein refers to methods by which the skilled artisan can predict the course or outcome of a condition in a subject. The term "prognosis" does not refer to the ability to predict the course or outcome of a condition with 100% accuracy, or even that a given course or outcome is predictably more or less likely to occur based on the presence, absence or levels of a biomarker. Instead, the skilled artisan will understand that the term "prognosis" refers to an increased probability that a certain course or outcome will occur; that is, that a course or outcome is more likely to occur in a subject exhibiting a given condition, when compared to those individuals not exhibiting the condition. For example, in individuals not exhibiting the condition, the chance of a given outcome may be very low (e.g., <1%), or even absent. In contrast, in individuals exhibiting the condition (e.g., elevated levels of shed ALCAM), the chance of a given outcome (e.g., suffering from a cancer or poor prognosis in connection with a cancer) may be high. In certain embodiments, a prognosis is about a 5% chance of a given expected outcome, about a 7% chance, about a 10% chance, about a 12% chance, about a 15% chance, about a 20% chance, about a 25% chance, about a 30% chance, about a 40% chance, about a 50% chance, about a 60% chance, about a 75% chance, about a 90% chance, or about a 95% chance.

The skilled artisan will understand that associating a prognostic indicator with a predisposition to an adverse outcome is a statistical analysis. For example, a biomarker level (e.g., quantity of shed ALCAM in a sample) of greater than a control level in some embodiments can signal that a subject is more likely to suffer from a cancer than subjects with a level less than or equal to the control level, as determined by a level of statistical significance. Additionally, a change in marker concentration from baseline levels can be reflective of subject prognosis, and the degree of change in marker level can be related to the severity of adverse events. Statistical significance is often determined by comparing two or more populations, and determining a confidence interval and/or a p value. See, e.g., Dowdy and Wearden, Statistics for Research, John Wiley & Sons, New York, 1983, incorporated herein by reference in its entirety. Exemplary confidence intervals of the present subject matter are 90%, 95%, 97.5%, 98%, 99%, 99.5%, 99.9% and 99.99%, while exemplary p values are 0.1, 0.05, 0.025, 0.02, 0.01, 0.005, 0.001, and 0.0001.

The "amount" of a biomarker determined from a sample refers to a qualitative (e.g., present or not in the measured sample), quantitative (e.g., how much is present), or both measurement of the biomarker. The "control level" can be an amount (including the qualitative presence or absence) or range of amounts of the biomarker found in a comparable biological sample in subjects free of a cancer, or at least free of the cancer of interest being tested.

The term "biological sample" is used herein refers to a sample derived from a subject. The sample can include body fluids (e.g., peripheral fluids), tissue samples, cells, or a combination thereof. Examples include, blood, serum, plasma, a tissue sample (including, but not limited to, a formalin-fixed tissue sample, a biopsy sample, or a sample obtained at the time of or from a resection), cerebrospinal fluid, urine, sweat, cells recovered from stool, and the like.

The terms "specific binding" or "specifically binds" as used herein refers to a measure of the capacity of a probe, such as an antibody, to bind a target polynucleotide with specificity.

In some embodiments, the shed ALCAM can be detected using a staining assay, as describe herein. In some embodiments, the shed ALCAM can be detected using an ELISA, as described herein.

Further with respect to the methods of the presently disclosed subject matter, a preferred subject is a vertebrate subject. A preferred vertebrate is warm-blooded; a preferred warm-blooded vertebrate is a mammal. A preferred mammal is most preferably a human. As used herein, the term "subject" includes both human and animal subjects. Thus, veterinary therapeutic uses are provided in accordance with the presently disclosed subject matter.

As such, the presently disclosed subject matter provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Thus, also provided is the diagnosis and treatment of livestock, including, but not limited to, domesticated swine, ruminants, ungulates, horses (including race horses), and the like.

The presently-disclosed subject matter is further illustrated by the following specific but non-limiting examples. The following examples may include compilations of data that are representative of data gathered at various times during the course of development and experimentation related to the present invention.

EXAMPLES

Example 1

In this Example, procedures were conducted to determine whether ALCAM shedding in human primary colorectal cancers reflects a unique molecular progression of the tumor and consequently acts as a prognostic biomarker. For this purpose a novel dual stain was developed to detect both the extracellular and the intracellular domain of ALCAM within the same tissue. As described below, ALCAM shedding in the primary tumor correlates strongly with a poor clinical outcome, especially in stage II patients in which disease-specific survival was significantly worse when the tumor tissue exhibited high ALCAM shedding.

Materials and Methods

Cell Lines and Mice

The continuous cell lines for cancer of the breast (MDA-MB-231 and MCF-7), prostate (PC3 and Du145) and colon (RKO, DLD, LOVO, LS174t, HCT116, HCA7, Scko1, Caco2, HT29, KM12c and KM12) were cultured in their appropriate basal media (DMEM or RPMI) with 10% FBS to confluence before lysis with 1% Triton-X 100 in PBS. ALCAM knockout mice (c57bl/6 ALCAM−/−) were purchased from Jackson Laboratories. Mouse tissues were surgically resected, snap frozen and subsequently extracted with 1% Triton-X 100 lysis buffer.

Western Blot Analysis

SDS-PAGE under non-reducing conditions and transfer of proteins to a PVDF membrane has been described previously (31). After blocking with 5% skimmed milk in PBS/0.05% Tween-20, blots were probed with primary antibodies for extracellular ALCAM (Clone 105902; R&D Systems) and selected hybridoma clones, followed by peroxidase-conjugated secondary antibody and ECL (Perkin-Elmer) detection.

Lentivirus-delivered RNA Interference

Four individual constructs containing shRNAs for human ALCAM and a negative control (scrambled sequence) were obtained from Sigma-Aldrich (St. Louis, Mo.) (Mission shRNA). Constructs were packaged for viral production and infection and tested for target knockdown. For viral packaging, constructs were co-transfected into 293T cells using Fugene HD (Roche Applied Science, Indianapolis, Ind.)). Media containing viruses were collected 48 hr after transfection. PC3 cells were infected with the viruses in the presence of Polybrene (8 μg/ml) for 24 hr and then subjected to selection by 5 μg/ml puromycin. Two constructs with ≥90% knockdown efficiency as determined by immunoblotting and flow cytometry were used for further studies.

Human Material

Tissue specimens from 250 colorectal cancer patient enrolled at Vanderbilt Medical Center (VMC, Nashville, Tenn., n=55) and Moffitt Cancer Center (MCC, Tampa, Fla., n=195) were used for gene-expression microarray analyses. All patients had a diagnosis of colorectal adenocarcinoma. Each cancer specimen was staged according to American Joint Commission on Cancer (AJCC) guidelines (stages I-IV), and 10 normal adjacent specimens were deemed to contain only normal colonic tissue by a certified gastrointestinal pathologist. VMC 55 includes 14 patients from the University of Alabama-Birmingham Medical Center (Birmingham, Ala.). Microarray data for the NCI cell lines was obtained through the NCBI Gene Expression Omnibus (GEO data set GDS1761).

A tissue microarray containing 75 primary colorectal carcinomas and 12 normal age and sex-matched colorectal mucosa was constructed using 2 mm cores in triplicate. Specimens from 69 CRC patients and 12 normal colonic mucosa were suitable to be used in the dual staining analysis. Subsequent expansion of this dataset was accomplished by selection of 36 stage II patients under IRB #120063 providing analysis for a total of 105 CRC and 12 normal mucosa with triplicate representation of each patient. Collection of serum from control (n=6), non-cancer patients (n=48) and colorectal patients immediately before surgery (pre-op, n=71) or after treatment (followup, n=20) at was accomplished at VMC under IRB#121365.

ALCAM Dual Immunofluorescence Stain

Immunofluorescent staining for ALCAM in tissues was performed with hybridoma HPA010926 (Sigma Prestige Antibodies) directed against the extracellular domain and clone 1G3A1 directed against the intracellular domain. Sections cut from patient tissue and tissue microarrays were deparaffinized in xylene and rehydrated. Sections were blocked in 20% Aqua Block™ after pressure cooker antigen retrieval in citrate buffer (pH 6.0). Samples were immunostained with mouse monoclonal intracellular ALCAM antibody, 1G3A1, (3 μg/ml) and rabbit monoclonal extracellular ALCAM antibody, HPA010926 (1:250 dilution). The arrays were incubated with Alexa-546 Goat anti-rabbit (1:500) and Alexa-647 Goat anti-mouse secondary antibody (1:500, LifeTechnologies). The sections were counterstained with 2 μg/ml of Hoechst for 2 mins, and mounted with Prolong® Gold Antifade.

Image Acquisition and Quantitative Analysis of ALCAM Shedding

Tissue microarrays were imaged using the Ariol® SL-50 platform from Genetix (Sunnyvale, Calif.). Image analysis and quantitation were performed using the open-source software ImageJ (FIJI). The analysis pipeline was designed as follows: a) The tumor area was selected using the free-hand selection tool. b) The color image was split into its red, green and blue component channels. c) Image thresholding was used to generate the detectable region of intracellular ALCAM staining (red channel) and extracellular ALCAM staining (green channel). d) Intact ALCAM was determined as the area of co-localized intracellular and extracellular ALCAM (red and green channel) while ALCAM shedding was determined as the area of intracellular ALCAM that lacks extracellular ALCAM (red but no green). The sum of these two represents total ALCAM expression.

Statistical Analysis

Descriptive statistics were applied to show patient's basic characteristics stratified by ALCAM shedding score. Wilcoxon rank sum test and Kruskal-Wallis test were applied to exam the mRNA expression difference between normal tissues and cancer tissues or the ALCAM shedding percentage among normal patients and cancer patients in all different stages. Kaplan-Meier curve was used to estimate the survival probability for each group, with corresponding p-value and hazard ratio calculated from log-rank test. Receiver Operating Characteristic (ROC) curves were used to identify the optimal specificity and sensitivity for patient stratification. For survival analysis the patient population was dichotomized across a value of ALCAM shedding or intact ALCAM as defined by the ROC curves. For ALCAM shedding this was 0.75 and for intact ALCAM this was 0.15 For shedding the p-values of all statistical tests were two-sided and considered significant when p<0.05 where * denotes p<0.05,  denotes p<0.01 and * denotes p<0.001. All statistics were completed using either R, SPSS or GraphPad Prism. Multivariable analysis using logistic regression was performed on stage II patients (n=66; median follow-up, 70 months; median age of diagnosis, 67 years). The variables included were ALCAM shedding, age at time of diagnosis, race and gender with an incidence of 51.5% (34 events) for overall survival and 26.9% (18 events) for disease specific survival.

Results

Figure 1B:
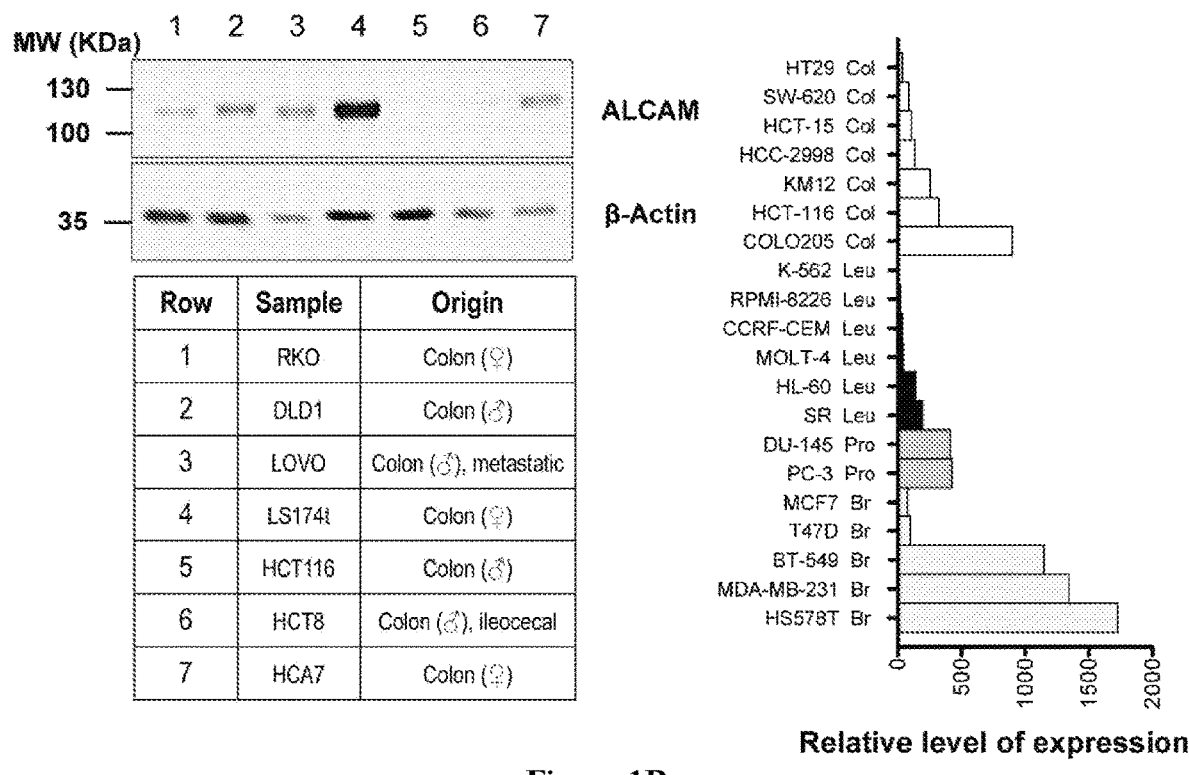
Figure 2A:
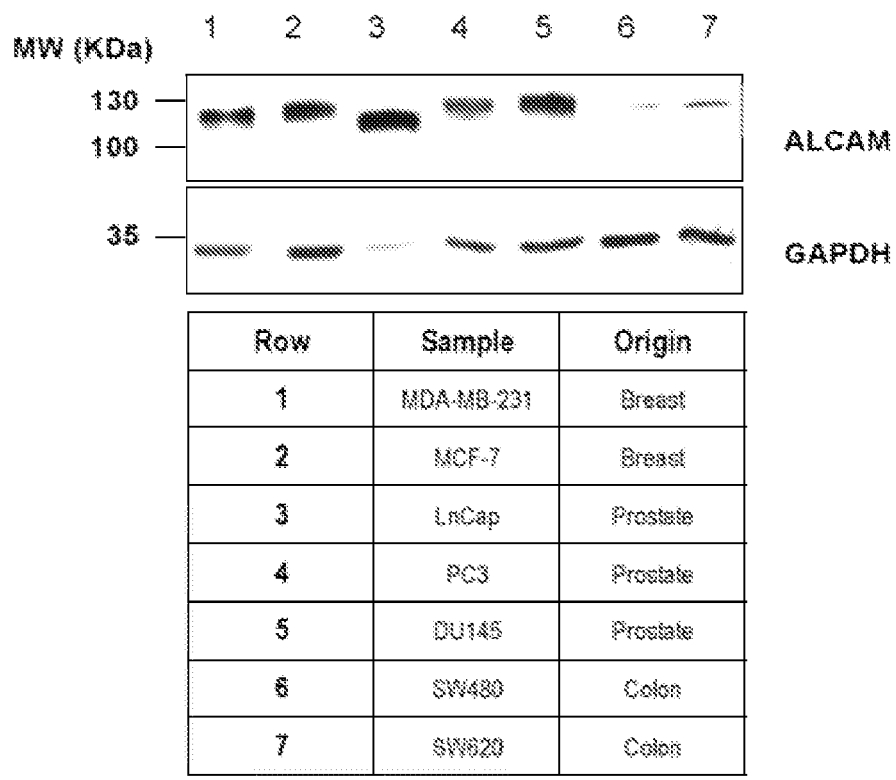
FIG. 2 shows ALCAM expression in continuous cancer cell lines. Lysates from human cancer cell lines immunoblotted for ALCAM using an antibody specific for its extracellular domain.
Figure 2B:
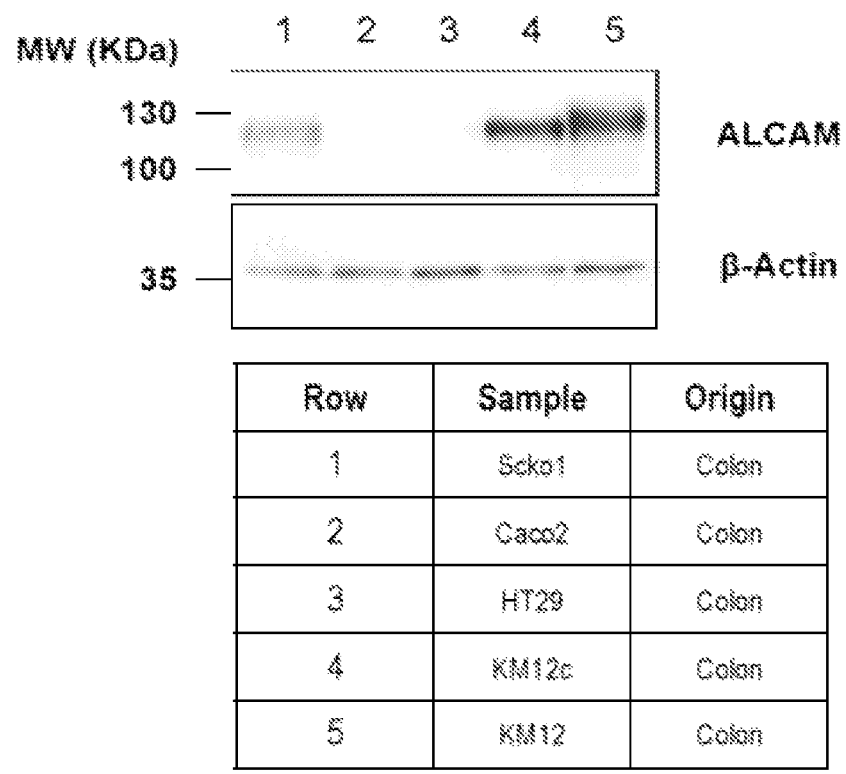

Correlation of ALCAM and ADAM17 Expression with Survival of Colorectal Cancer Patients In normal colorectal tissue, immunohistochemical staining for the extracellular domain of ALCAM using HPA10926 reveals the protein at areas of cell-cell contact within the epithelial cells of the colonic crypts and in hemopoietic cell populations of the stroma (FIG. 1A(i and ii)). In contrast to normal colon, the concomitant staining of colorectal cancer tissue reveals a very heterogeneous staining. Within the same tumor, some regions exhibit elevated ALCAM (FIG. 1A(iii)) while others exhibit irregular staining (iv) or lack ALCAM staining all-together (v). Similar heterogeneity of ALCAM staining is observed in a publicly available tissue microarray (proteinatlas.org). ALCAM protein expression is detectable in 12/14 CRC cell lines (FIGS. 1B and 2). Expression of the ALCAM mRNA in CRC cell lines among the NCI60 (Col) is intermediate between the low expressing leukemia (Leu) cell lines and the high expressing breast cancer (Br) cell lines (FIG. 1B).

Figure 1C:
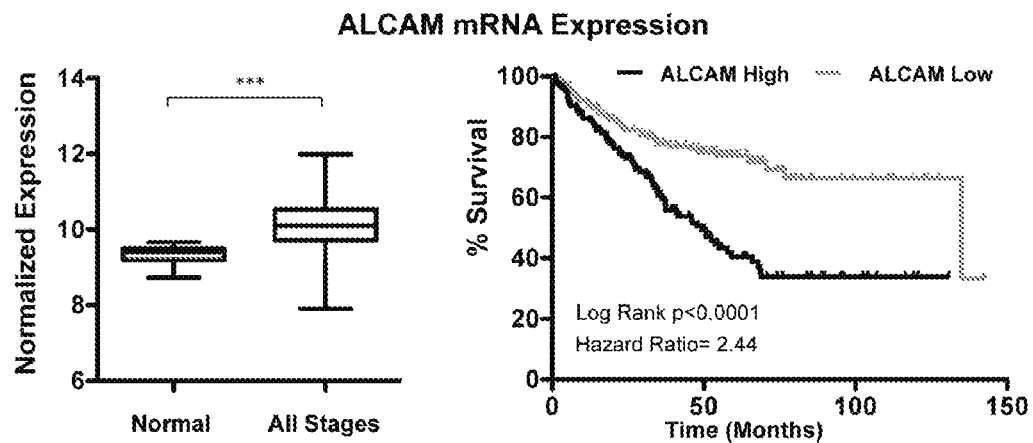
Figure 1D:
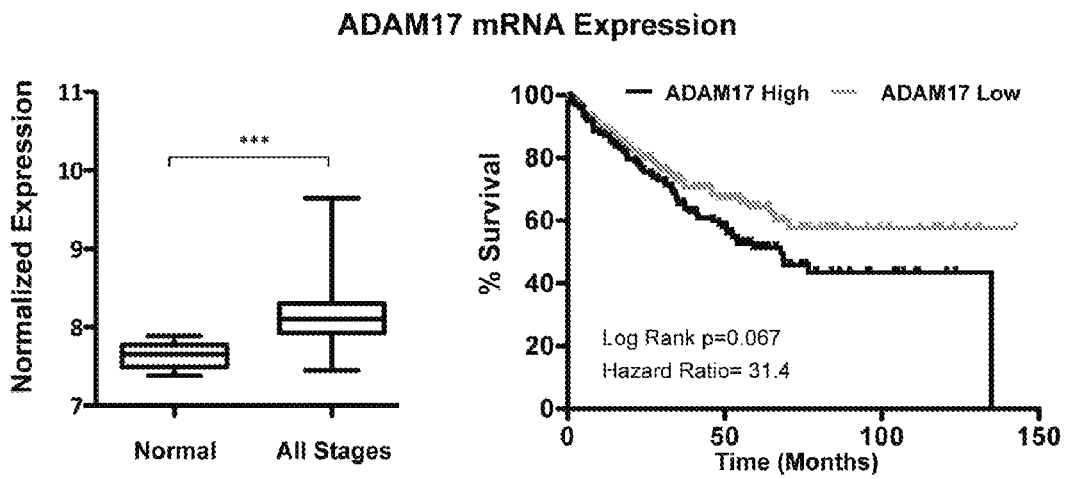
Figure 1E:
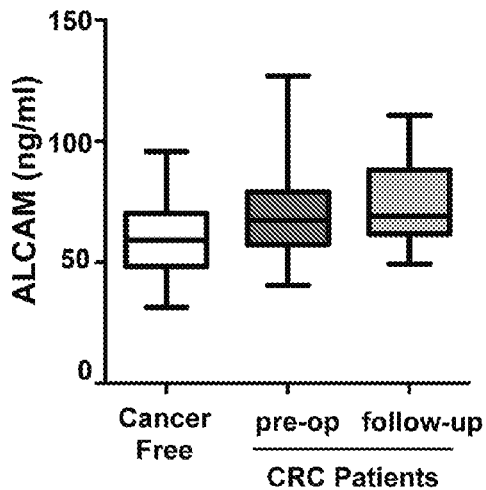
Figure 1F:
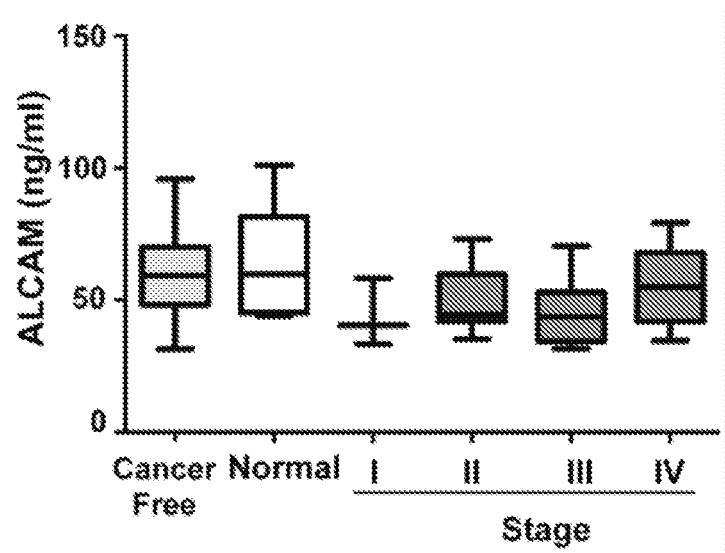

To evaluate ALCAM mRNA expression in colorectal cancer, a single cohort consisting of 250 patients obtained through a multi-institutional collection (VUMC, UAMC and Moffitt Cancer Center) was analyzed. ALCAM mRNA is elevated in cancer patients (FIG. 1C, p<0.001) and univariate analysis revealed that high ALCAM expression was in fact associated with significantly decreased survival (FIG. 1C, p<0.0001). Similarly, expression of ADAM17 (the sheddase of ALCAM) was also significantly elevated in colorectal cancer (FIG. 1D, p<0.0001). The elevated expression in CRC together with its established ability to cleave ALCAM suggests that ADAM17 is available to cleave ALCAM and increase its shedding within the tumor microenvironment. The soluble extracellular domain can be detected in the serum of some cancer patients. However, ALCAM-specific ELISA of serum from CRC patients did not reveal a correlation between disease progression and increase in circulating ALCAM when comparing serum obtained from cancer free patients and serum obtained from CRC patients prior to, and after therapy (FIG. 1E). Detailed comparison of cancer free patients and normal healthy individuals versus increasing stages of CRC patients revealed no significant correlation with circulating levels of ALCAM (FIG. 1F).

Figure 3:
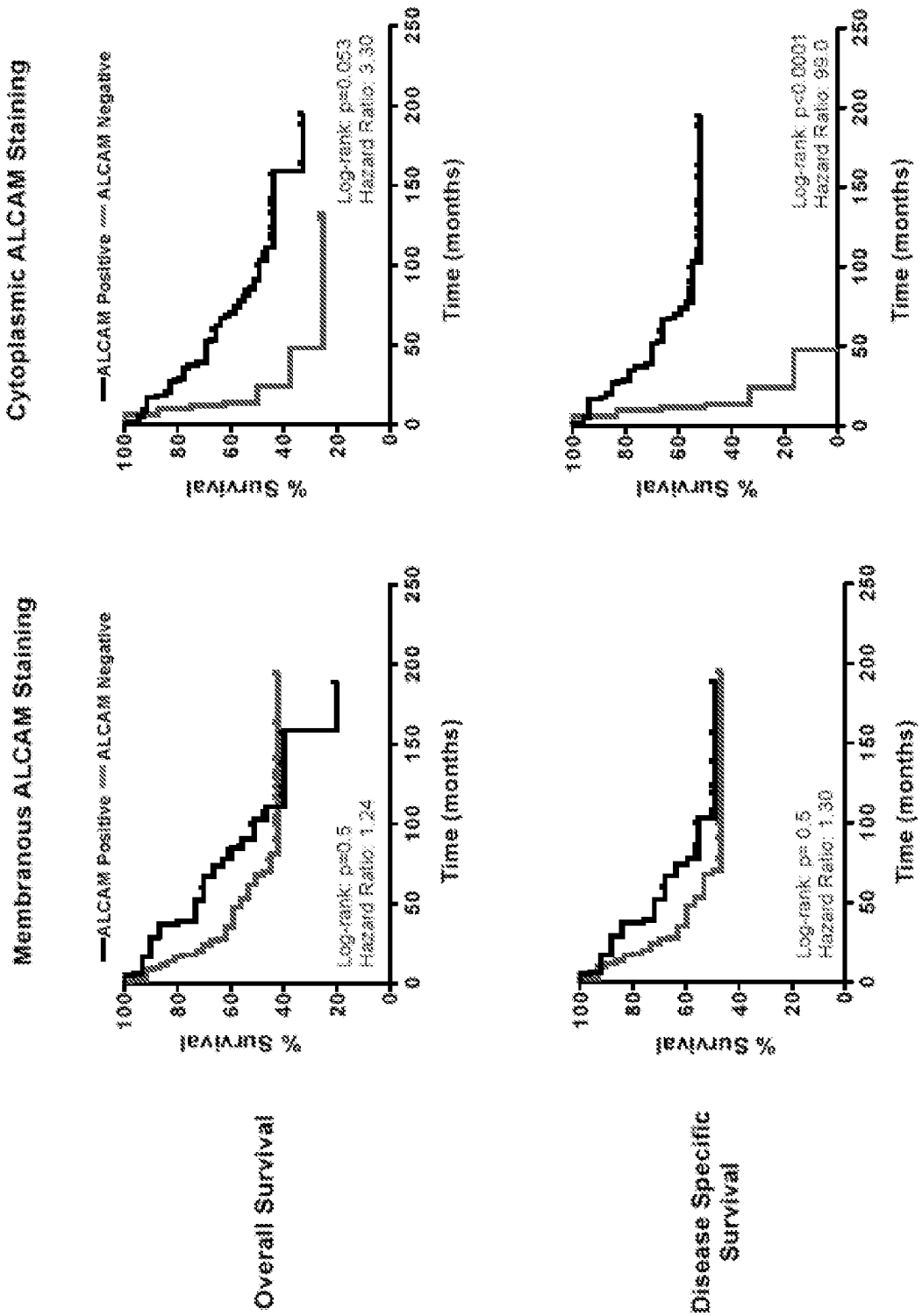
FIG. 3 shows that the lack of cytoplasmic ALCAM corresponds with poor patient outcome. A tissue microarray of 75 CRC and 12 normal colonic tissues was stained by traditional IHC for the extracellular domain of ALCAM. Membranous and cytoplasmic staining was stained and scored by an independent pathologist in a blinded manner.

The histological detection of membranous ALCAM had been found to correspond negatively with patient survival. Using an antibody to the extracellular domain of ALCAM, a histological evaluation of a 69-patient cohort was performed (FIG. 3). While the presence or absence of membrane staining did not correspond with overall or disease specific survival, the loss of detectable cytoplasmic ALCAM corresponded with very poor prognosis. However, only 8/69 patients (12%) were negative for cytoplasmic ALCAM while 39/69 (56%) lacked membranous ALCAM. This loss of ALCAM from the membrane (with concomitant retention of cytoplasmic staining) is likely to be due to shedding of the ectodomain from the cell surface.

Figure 4A:
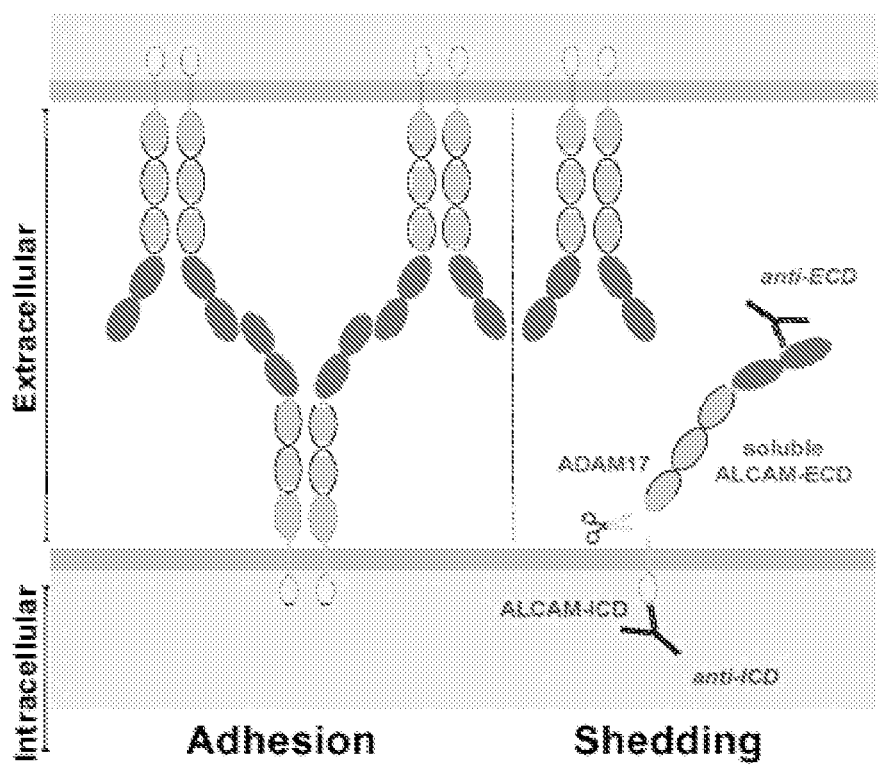
FIG. 4 shows the specificity of anti-ALCAM ICD confirmed by analysis of ALCAM in ALCAM−/− mice. A) Schematic representation of ALCAM and its organization as a cell-cell adhesion molecule. Individual domains are presented as ovals (extracellular IgG-like domain) or rectangles (intracellular domain). B) The antibody 1G3A1 specific for the cytoplasmic tail of ALCAM was used to immunoblot 40 µg of liver extracts from wild type and ALCAM−/− mice. C) ALCAM specificity of individual clones was evaluated by outcompeting antibody binding with the immunizing peptide in immunofluorescence staining of human lung tissue sections.
Figure 4B:
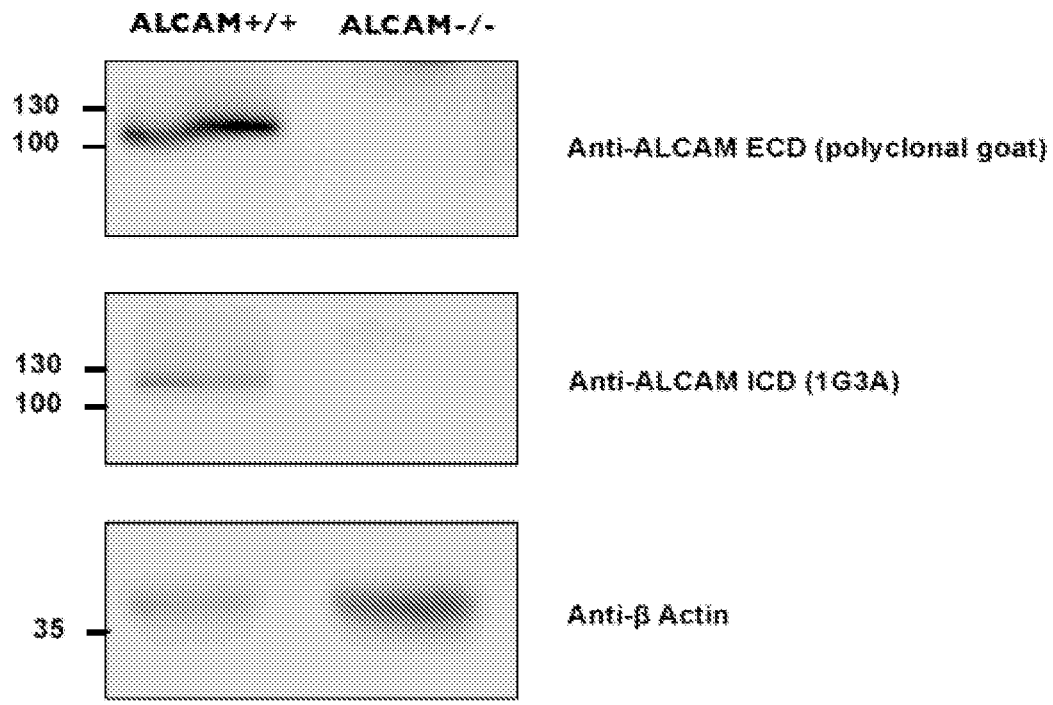
Figure 4C:
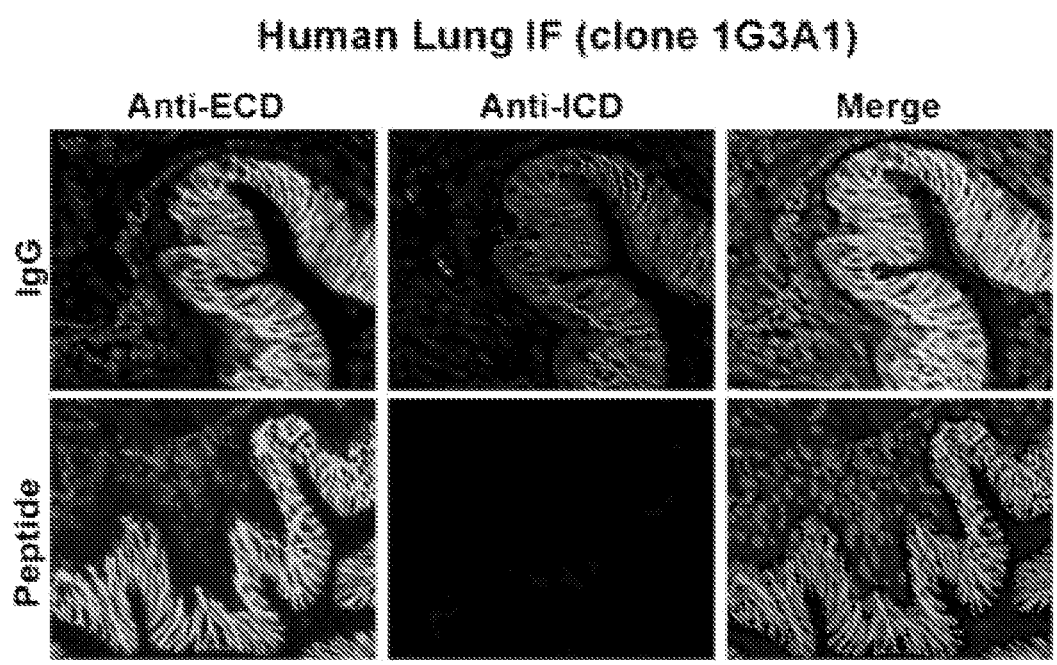
Figure 5:
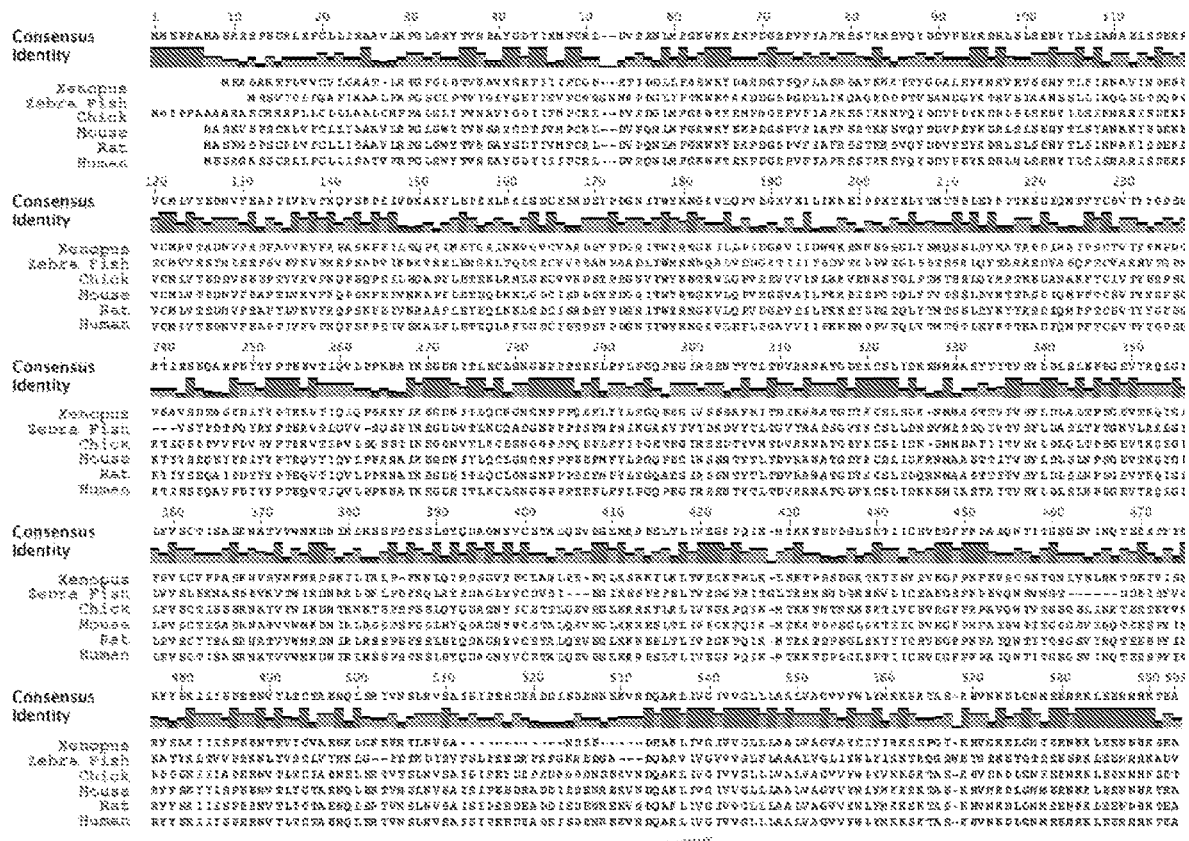
FIG. 5 shows multi-species sequence alignment was carried our using the Geneious™ bioinformatics software. Along the top of each alignment is the sequence identity plot comparing the sequence across species. Green peaks are 100% identity among species; yellow and red are lower identities. Immunogen sequence is located in the cytoplasmic tail consisting of a highly conserved 14 amino acid sequence.
Figure 6A:
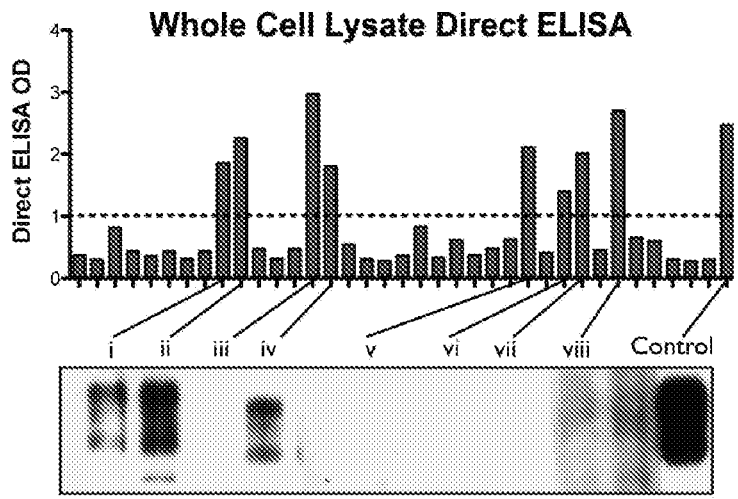
FIG. 6 shows the screening and validation of an antibody specific to the cytoplasmic domain of ALCAM. A) B) Individual hybridoma clones reactive to the immunizing peptide were screened by direct ELISA using whole cell lysate from a cell line expressing high levels of ALCAM (PC3). A 1.0 OD was used to select clones for further validation by immunoblotting cutoff. Three high-titre clones chosen for further validation were 1G3A1 (ii), 1G3B3 (iv), and 1G3CF (i). B) Hybridoma clones 1G3A1, 1G3B3, and 1G3CF were further for specificity to ALCAM by comparing their reactivity to ALCAM with a commercial antibody (directed against the extracellular domain) using lysates from parental PC3 cells and PC3 cells with shRNA-mediated knockdown of ALCAM. C) ALCAM specificity of individual clones was further evaluated by outcompeting antibody binding with the immunizing peptide in Immunoblots of whole cell lysates (PC3). D) Specificity of purified 1G3A1 against the cytoplasmic tail of ALCAM was confirmed by immunoblotting intact ALCAM (whole cell lysate; Lys.) and shed ALCAM (conditioned medium; C.M.) from PC3 cells.
Figure 6B:
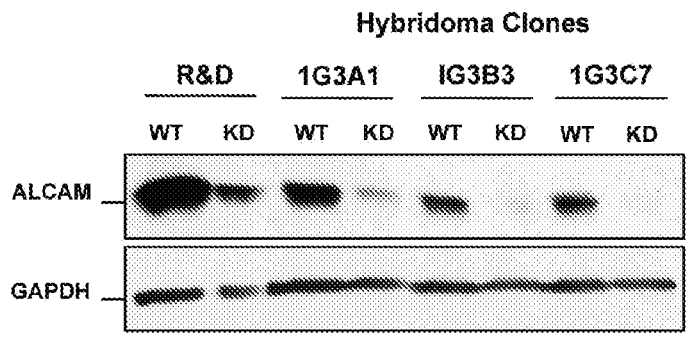
Figure 6C:
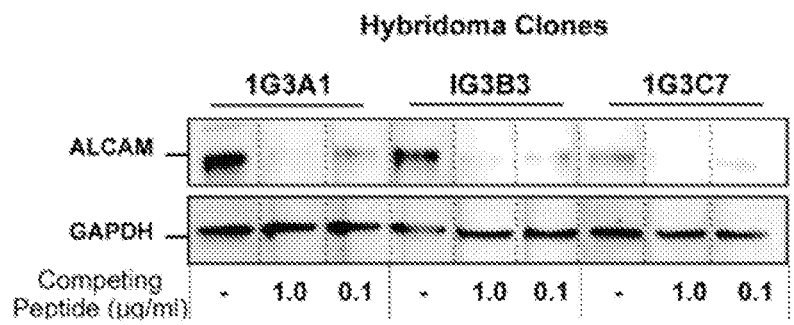
Figure 6D:
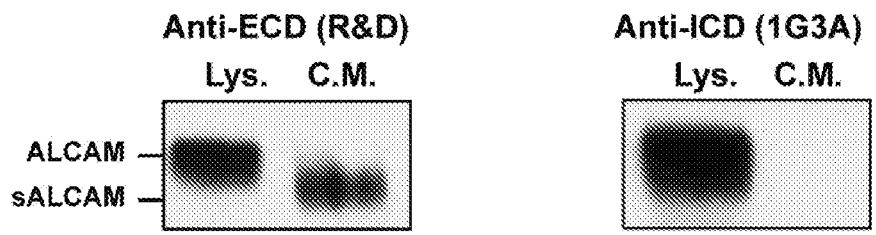

Production and Validation of an Antibody Specific for the Cytoplasmic Domain of ALCAM Since ALCAM shedding occurs on the surface of the tumor cells, it is possible that shedding might be detectable within the tumor tissue itself. In order to achieve this, an ALCAM dual-stain based on independent detection of the intracellular and extracellular domains with domain-specific antibodies was developed (FIG. 4A). Using these antibodies in histological staining of normal and tumor tissue sections should enable the detection of ALCAM shedding in situ (Table 1). To accomplish this, a unique antibody directed to the cytoplasmic tail of ALCAM was generated using a 14 AA sequence from the cytoplasmic tail (FIG. 5) conjugated to KHL to immunize four A/J mice. Spleens from two seropositive mice were fused and 125 viable hybridomas selected from >8000 antigen-reactive clones were evaluated by comparing reactivity to native ALCAM and KLH using direct ELISA (FIG. 6A). ALCAM-specific hybridomas were validated by immunoblotting using whole cell lysate to confirm binding to intact ALCAM protein (FIG. 6A). Antibody specificity for ALCAM was verified by comparing reactivity with lysates from control and ALCAM knockdown cells (FIG. 6B) and mouse tissue from wild type and ALCAM−/− mice (FIG. 4B). Antigen specificity was confirmed by competitive blocking using the immunizing peptide during immunoblotting (0.1 or 1 μg/ml, FIG. 6C) and histological staining (1 μg/ml, FIG. 4C). As expected, peptide competition with the immunizing peptide resulted in a loss of Intracellular ALCAM. The stable hybridoma 1G3A1 was selected as the most promising antibody based on its reactivity in ELISA, immunoblot, immunofluorescence and standard immunohistochemistry. Specificity of 1G3A1 for the cytoplasmic tail of ALCAM was defined by its ability to detect intact ALCAM in cell lysates but not shed ALCAM in conditioned medium (FIG. 6D). In contrast, the commercial antibody against the extracellular domain of ALCAM (R&D) detects intact as well as shed ALCAM which lacks the cytoplasmic domain.

TABLE 1

Depiction of ALCAM immunoreactivity for HPA1096 which reacts with the extracellular domain and 1G3A1 which is specific for the intracellular domain.

| | Antibody reactivity | | ALCAM Schematic | |
| --- | --- | --- | --- | --- |
| ALCAM Status | Intracellular Domain (1G3A1) | Extracelluar Domain (HPA 10926) | HPA10926 | 1G3A1 |
| Intact ALCAM | + | + | | |
| ALCAM Shedding | + | − | | |
| ALCAM Absent | − | − | | |

Figure 7A:
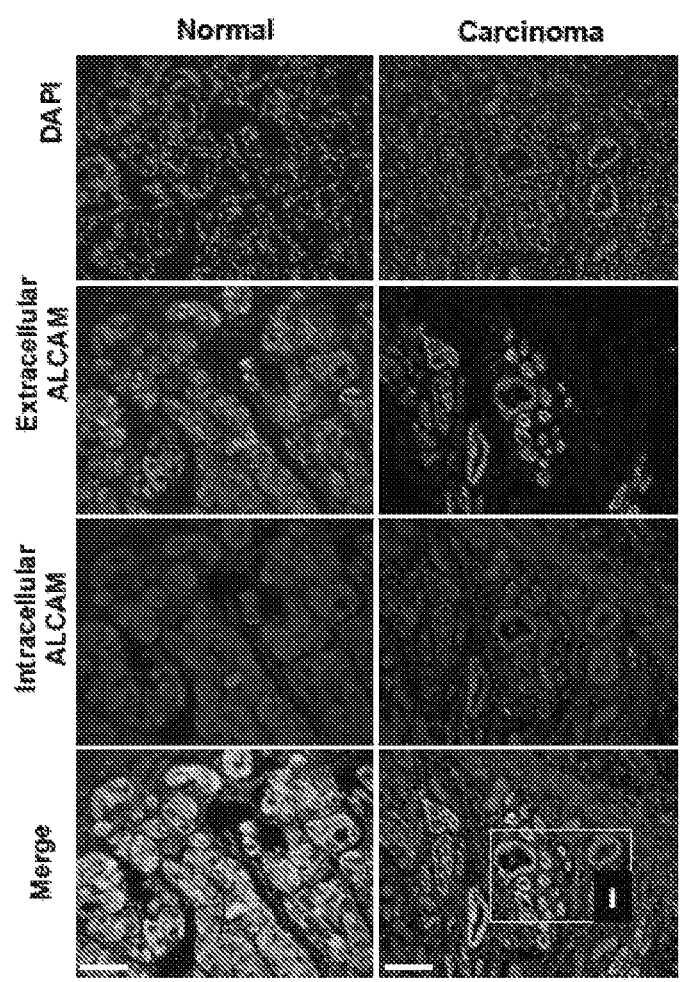
FIG. 7 shows the detection of ALCAM shedding in cancers of the stomach and colon. The ALCAM dual stain composed of the antibody HPA010926 directed against the extracellular domain (green) and antibody 1G3A1 directed against the intracellular domain (red) was used to identify locations within the tissue that exhibited ALCAM shedding in cancers of the stomach (A) and colon (B), scale bar=64 µm. Images of nuclear stain (blue) were merged with images of HPA010926 (green) and 1G3A1 (red) staining. Insets (C) present magnified regions i and ii from stomach and colon carcinoma. Areas of ALCAM shedding are identified by the presence of 1G3A1 staining (red) and an absence of HPA010926 (green) staining. Arrow: intact ALCAM, Arrow Head: ALCAM shedding. Scale bar=320 µm.
Figure 7B:
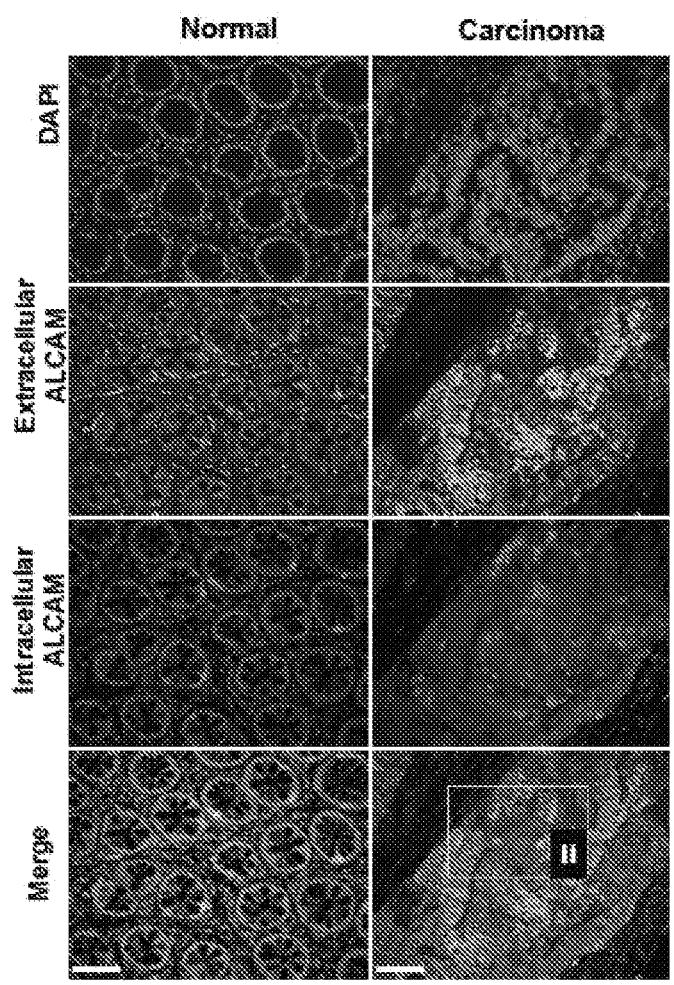
Figure 7C:
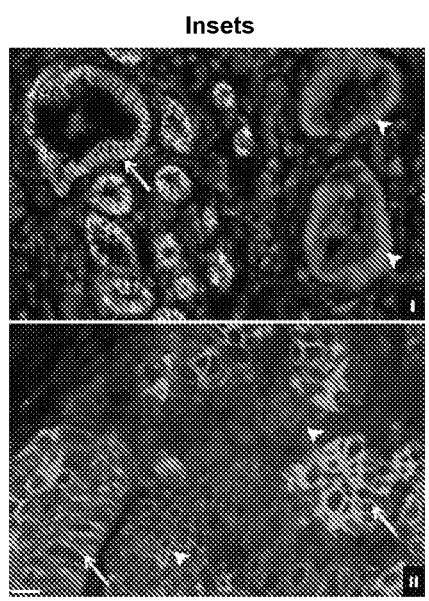
Figure 8:
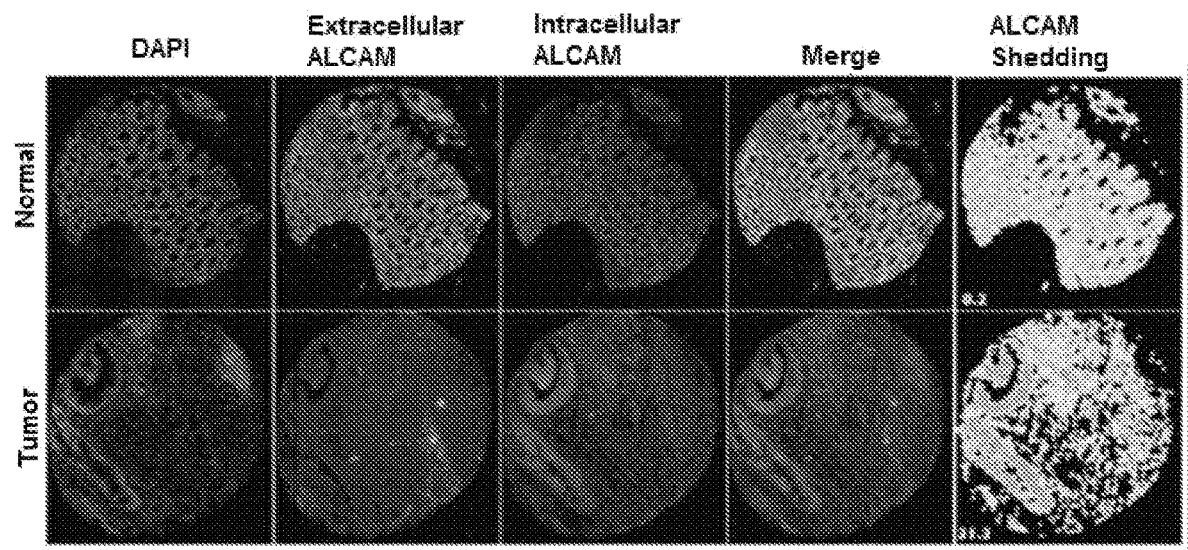
FIG. 8 shows the quantitative analysis of ALCAM shedding in CRC. The ALCAM dual stain was used to detection the extracellular domain (green) and intracellular domain (red) of ALCAM in normal colonic mucosa (A) and colorectal cancer (B). ALCAM shedding was defined as the detection of ALCAM-ICD in the absence of co-localized ALCAM-ECD. The results of this analysis presents ALCAM shedding quantitatively as the fraction of total detectable ALCAM from which the extracellular domain is absent.

Dual-staining for the Intracellular and Extracellular Domains of ALCAM in Normal and Tumor Tissue Using the antibody 1G3A1 to specifically detect the cytoplasmic domain of ALCAM together with the commercial antibody HPA010926 specific for the extracellular domain, we developed a dual-staining procedure for ALCAM in human tissues (FIGS. 7 and 8). Three-color staining (Nuclei: blue, Extracellular Domain: green, Intracellular Domain: red) was performed on tissues along the digestive tract including stomach (FIG. 7A) and colon (FIG. 7B). In normal tissues, detection of the extracellular and cytoplasmic domains of ALCAM coincided, thereby suggesting that ALCAM is expressed and present in its intact form (FIG. 7C, arrow). However, within tumor tissues the intracellular domain (Red) is often seen in the absence of the extracellular domain (Green) indicating that the extracellular domain of ALCAM was shed (FIG. 7C, arrow head). In gastric cancer, entire glandular structures appear to lack staining for the extracellular domain while others are fully positive (FIG. 7Ci). This all-or-none staining for the extracellular domain suggests that ALCAM-shedding is activated at a macroscopic level within the tissue architecture of the stomach. In colorectal carcinoma tissue ALCAM staining is more heterogeneous with small populations of cells within the same histological structure exhibiting different levels of staining for the ALCAM extracellular domain (FIG. 7Cii). The irregular staining in CRC suggests that ALCAM shedding is occurring throughout the tumor but regulated at a cellular level.

Quantitative Analysis of ALCAM Shedding

Figure 9:
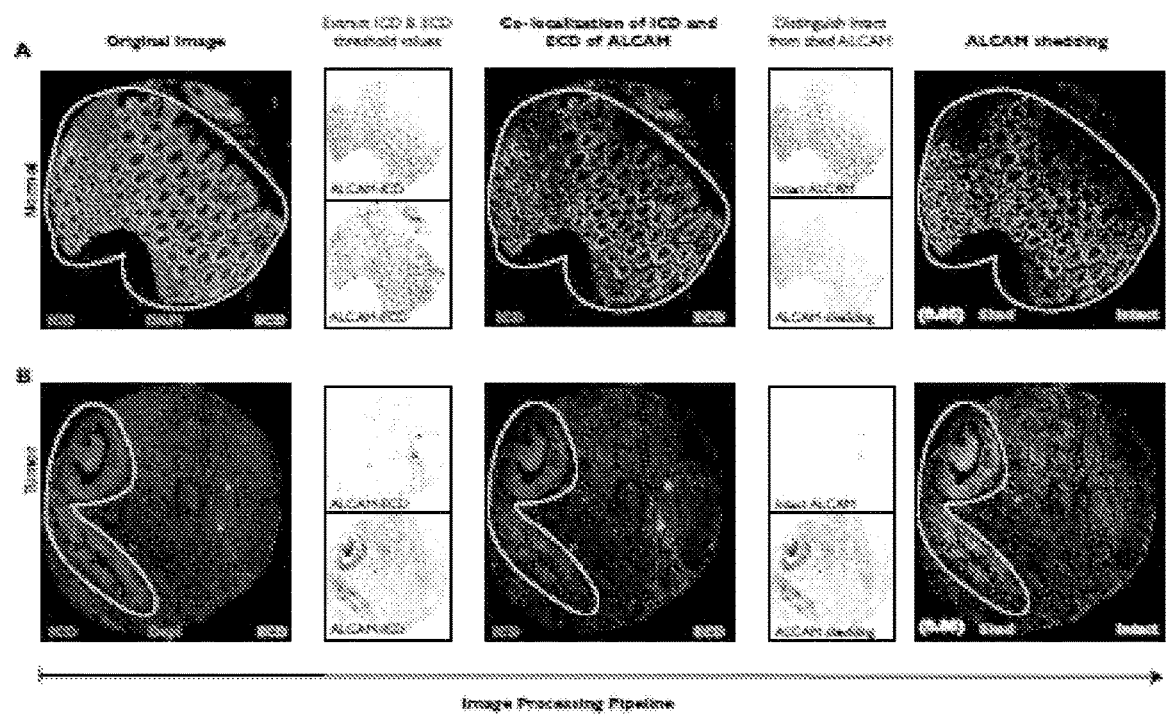
FIG. 9 shows the image processing pipeline implemented using FIJI. Images obtained of normal (A) and tumor (B) tissues through scanning on the Ariol® platform were processed to obtain the fraction of ALCAM shed. The original images was separated into its individual color channels and threshold values were obtained for the red channel (AL-CAM-ICD) and the green channel (ALCAM-ECD). A co-localization of these thresholded areas was used to distinguish intact ALCAM (both ALCAM-ICD and -ECD, yellow) from shed ALCAM (only ALCAM-ICD, teal). Quantitatively ALCAM shedding is defined as the fraction of detectable ALCAM from which the extracellular domain is absent.

To visualize ALCAM shedding, HPA010926 (Sigma) was used to detect the extracellular domain and 1G3A1 (FIG. 6) to detect the intracellular domain. Shedding of ALCAM was defined for the selected tumor area as the presence of the intracellular domain of ALCAM and the absence of the extracellular domain of ALCAM (FIG. 8). Immunofluorescent staining for each domain was completed simultaneously on sections from paraffin-embedded colorectal cancer tissue which were digitally scanned and quantitatively assessed using ImageJ (FIG. 9). Shedding was defined as the loss of the extracellular domain and retention of the cytoplasmic domain. Shedding data is presented graphically in FIGS. 8A and 8B. Quantitatively ALCAM shedding is the fraction of detectable ALCAM from which the extracellular domain is absent ([Total ALCAM-Intact ALCAM]/Total ALCAM). In normal colonic mucosa, detection of the extracellular and intracellular domains overlap extensively, demonstrating the predominant presence of intact ALCAM (yellow) and little ALCAM shedding (teal) (FIG. 8A, last panel). Conversely, in tumor sections the intracellular domain of ALCAM remains detectable while the extracellular ALCAM is frequently absent, indicating that ALCAM is shed (FIG. 8A, last panel).

ALCAM Shedding Corresponds with Reduced Patient Survival

Figure 10A:
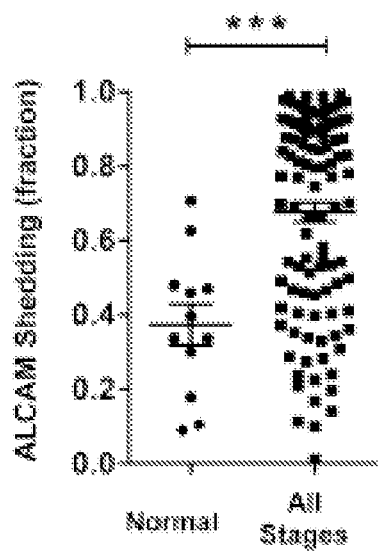
FIG. 10 shows ALCAM shedding in CRC correlates with poor survival. Scatter plots demonstrate the differences in ALCAM shedding between normal colonic mucosa and CRC tumors as a single population (A), stratified across histological stage (B), or separated according to survival (C). Kaplan-Meier survival curves of CRC patients with high versus low ALCAM shedding were generated and log-rank tests performed to evaluate the correlation of ALCAM shedding with overall survival of patients at all stages (D), overall survival of stage II patients (E) or disease-specific survival of stage II patients (F). Scatter plots show the mean and SEM with statistical evaluation by Mann-Whitney for selected groups (A and C) or Kruskal-Wallis with Dunn's multiple comparison restricted to normal (B).
Figure 10B:
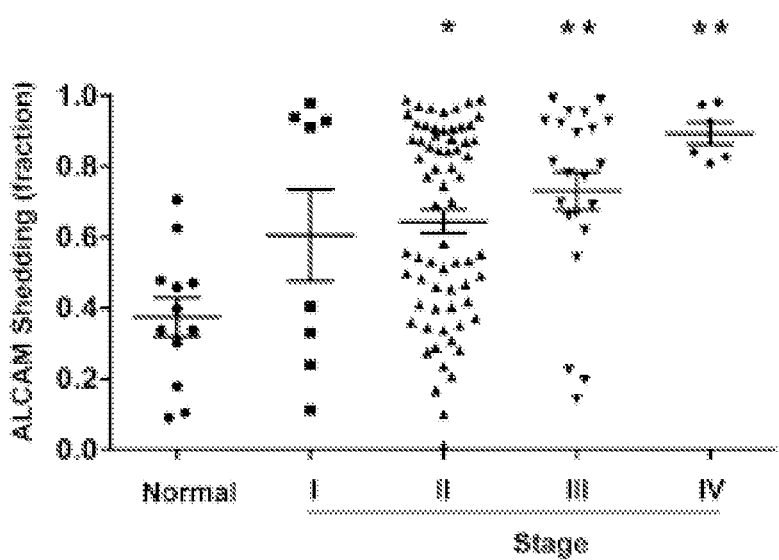
Figure 10C:
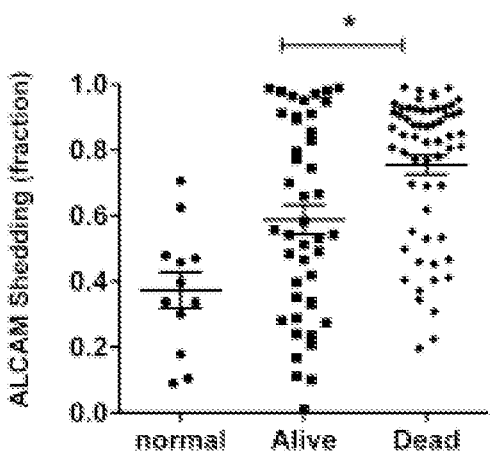

Since ALCAM shedding is clearly elevated in tumors, without being bound by theory or mechanism, ALCAM shedding can be an accurate prognostic marker for colorectal cancer. To evaluate this, histological detection of ALCAM shedding was performed on specimens from 105 CRC patients and 12 healthy controls (see Table 2 for patient demographics). For each specimen, ALCAM shedding was quantified as described for FIG. 8. For each patient, the mean value across three specimens was used to evaluate the correlation between ALCAM shedding and patient survival. ALCAM shedding is clearly elevated in tissue from CRC (FIG. 10A). Shedding is already increased in some stage I CRC patients and is significantly increased for stage II, III and IV patients. Indeed ANOVA analysis confirms significant elevation across the increasing stages (mean fraction shed=0.64, 0.73, and 0.89, for stage II, III, and IV, FIG. 10B). Moreover, ALCAM shedding was elevated in patients that died during the course of their disease. The presence of elevated ALCAM shedding in stage II patients may suggest that patients with elevated ALCAM shedding have a worse outcome.

TABLE 2

Comparison of High and Low ALCAM shedding colon cancer with respect to Age, Sex, and Staging.

| Characteristic | Total | Low ALCAM Shedding* | High ALCAM Shedding* |
|---|---|---|---|
| N (%) | 105 | 50 (47.6) | 55 (52.4) |
| Age at Dx [Range] | 63.7 [10-90] | 61.5 [26-89] | 65.6 [10-90] |
| AJCC Stage (%) | | | |
| I | 8 (10.7) | 4 (50) | 4 (50) |
| II | 66 (42.7) | 35 (53) | 31 (45.9) |
| III | 25 (37.3) | 10 (40) | 15 (60) |
| IV | 6 (9.3) | 0 (0) | 6 (100) |
| Sex (%) | | | |
| M | 52 (49.3) | 27 (52) | 25 (48) |
| F | 53 (50.7) | 23 (43) | 30 (57) |
| Average ALCAM Shedding Score [Range] | 0.68 [0.011-0.99] | 0.42 [0.011-0.75] | 0.89 [0.77-0.99] |

*Low and High ALCAM are dicotomized across the fraction of ALCAM that is shed being equal to 0.75.

Figure 10D:
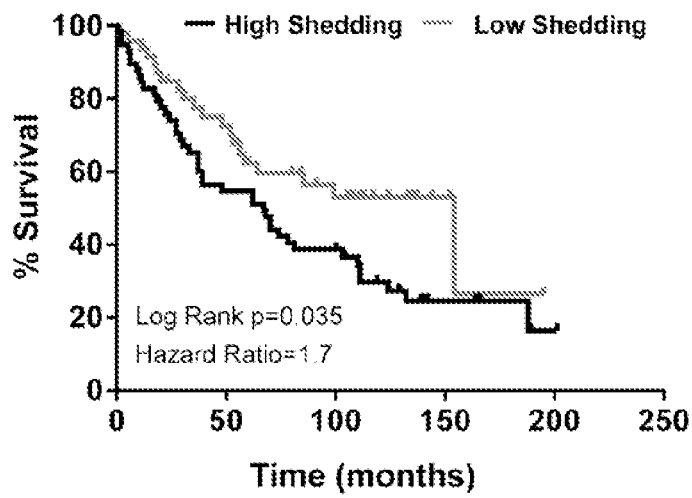
Figure 10E:
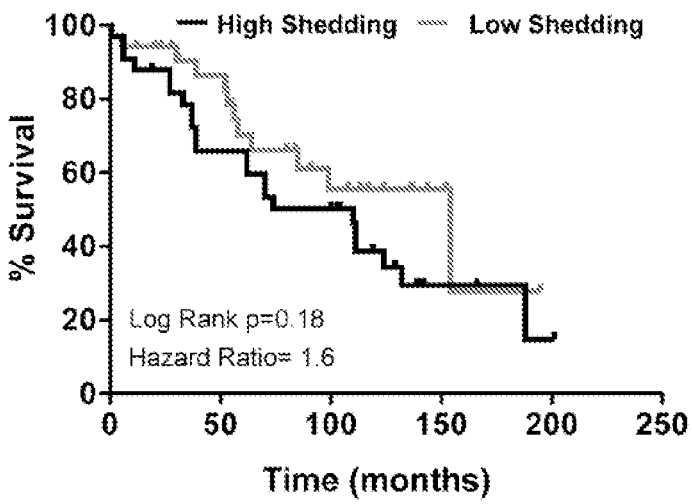
Figure 10F:
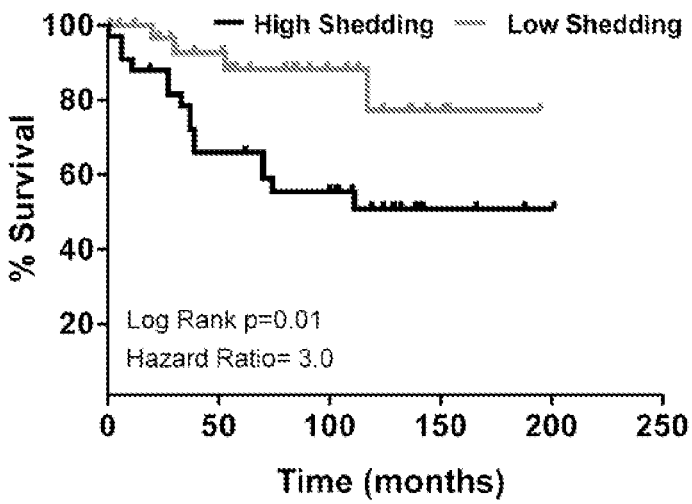

To evaluate the correlation between ALCAM shedding and patient outcome, survival analysis was performed by segregating CRC patients based on ALCAM expression (FIG. 10D) using a shed fraction of 0.75 to delineate "High" vs "Low" ALCAM shedding. When analyzing the full population of CRC patients, high ALCAM shedding correlated positively with worse overall survival (p=0.035, FIG. 10D). To determine if ALCAM shedding can be prognostic for early stage disease, a univariate survival analysis was performed specifically to stage II patients. While ALCAM shedding does not correlate with overall survival in stage II patients (FIG. 10E), it correlates strongly with disease-related death showing significant survival benefit in the Stage II patients with low ALCAM shedding (FIG. 10F, p=0.01 HR=3.0).

Multivariable analysis was restricted to stage II patients since they were the emphasis of the investigation and the cohort biased to this population. Multivariable analysis with logistic regression of stage II patients found that ALCAM shedding and age at time of diagnosis were both independent predictors of overall survival after adjusting for gender and race (ALCAM shedding; adjusted odds ratio (OR), 9.972; 95% confidence interval (CI) 1.17-84.9; p=0.035. Age; OR, 1.079; 95% CI, 1.027-1.133; p=0.003). An analysis of disease-specific survival found that only ALCAM shedding was an independent predictor of survival after adjusting for age at time of diagnosis, race and gender (ALCAM shedding OR, 29.02; 95% CI, 2.165-389.08; p=0.011). Bootstrapping was performed as an internal validation to confirm these results and found that ALCAM shedding continued to be an independent predictor of survival in stage II patients (overall survival p=0.002; disease-specific survival p=0.023).

Discussion

It appears that ALCAM shedding, rather than its expression, indicates disease progression. The dual stain reveals both intra- and extracellular epitopes of ALCAM and clarifies its prognostic value in CRC. ALCAM shedding in tissues was defined as the detection of the intracellular epitope in the absence of the extracellular domain. Using this novel assay, a correlation between elevated ALCAM shedding and poor patient outcome was demonstrated. Importantly, ALCAM shedding correlates with poor outcome in early stage disease (Stage II, FIG. 10). Thus, ALCAM is not merely a biomarker for disease progression but can also allow for outcome stratification among patients with early stage disease.

ALCAM shedding within the tumor tissue appears to correspond with disease progression. The detection of ALCAM shedding within the tumor tissue itself can increase the specificity of ALCAM as a prognostic factor. In this Example a method was devised to stratify at-risk patients using ALCAM shedding as an indicator of disease progression and poor patient outcome, and not as a diagnostic tool. Indeed, the correlation between ALCAM shedding and poor patient outcome in early stage disease suggests that molecular progression can occur in a cancer that appears histologically more benign.

Figure 11:
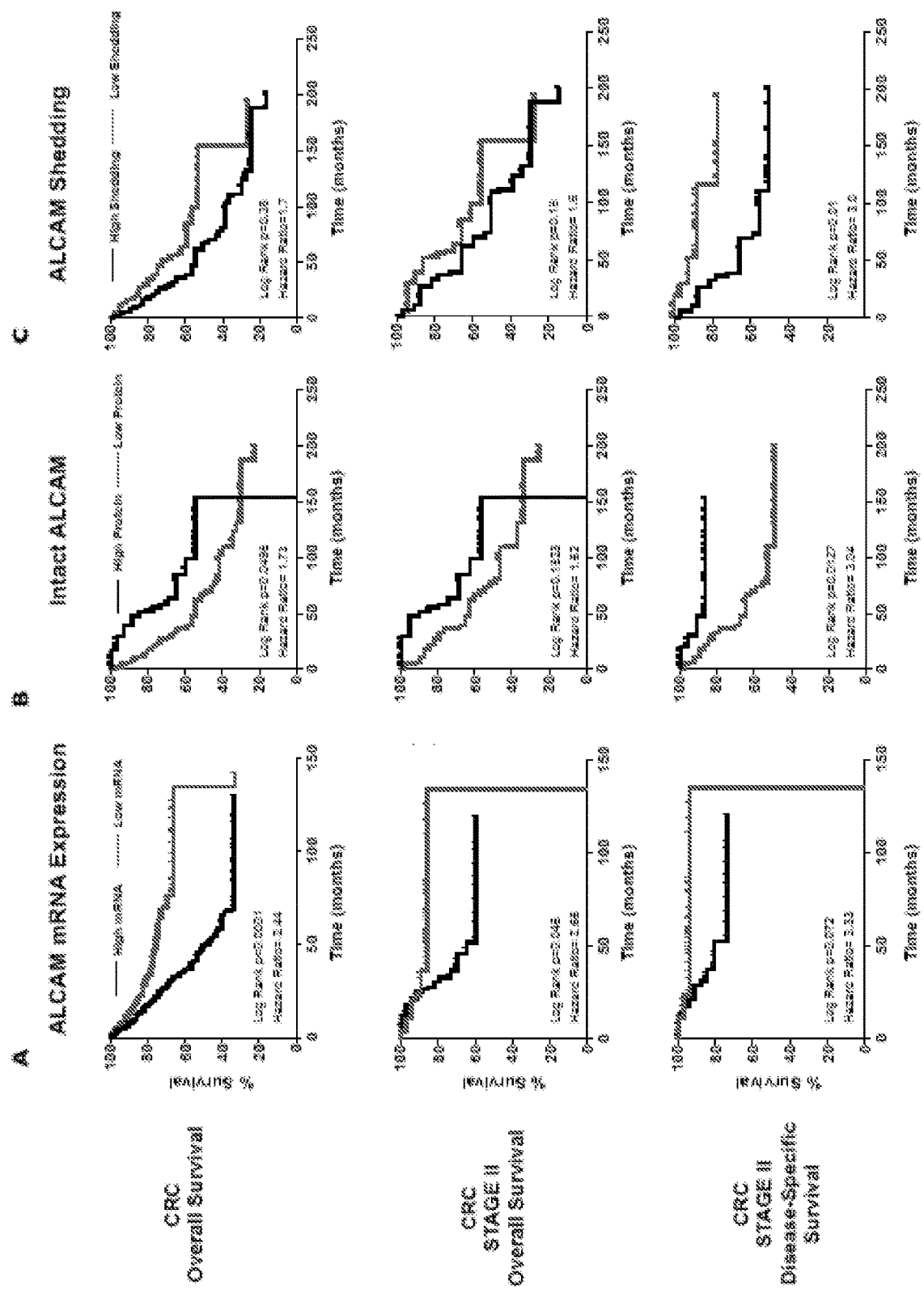
FIG. 11 shows ALCAM mRNA, protein and shedding in colorectal cancer. Kaplan-Meier survival analysis contrasts CRC patients overall survival, stage II patient overall survival and disease-specific stage II CRC survival with high versus low ALCAM mRNA expression (A) protein expression (B) or ALCAM shedding (C). Survival is presented as Kaplan-Meier plots with the log-rank test used to evaluate significance.

A disparity becomes apparent when clinical outcome (survival) are correlated with ALCAM gene transcription (mRNA), protein expression (based on detection of intact ALCAM) and ALCAM shedding. Elevated ALCAM transcription is associated with poor outcome yet elevated levels of intact ALCAM protein (through detection of co-localized extracellular domain and intracellular domain) is associated with improved outcome (FIG. 11A vs. 11B). This disparity could be rectified if it is considered that the extracellular domain of ALCAM is shed leaving the mistaken impression that ALCAM protein is lost during tumor progression. The analysis of ALCAM shedding (FIG. 11C) demonstrates that ALCAM shedding rather than loss of expression corresponds with patient outcome.

The results suggest that detection of molecular behavior correlates more specifically with the disease than gene expression itself. Given that the disruption of ALCAM-ALCAM interactions promotes tumor cell motility and metastasis, ALCAM shedding may predict malignant progression at a molecular level. The clinical correlation between ALCAM shedding and patient outcome (FIG. 10) suggests that detection of disease progression at a molecular level can predict long-term patient outcome. The presence of this correlation in early stage disease (stage II, FIG. 10) emphasizes that this molecular progression is present prior to pathological and clinical progression. Detection of this molecular progression allows for stratification of patients according to their risk for poor long-term outcome.

Example 2

Figure 12:
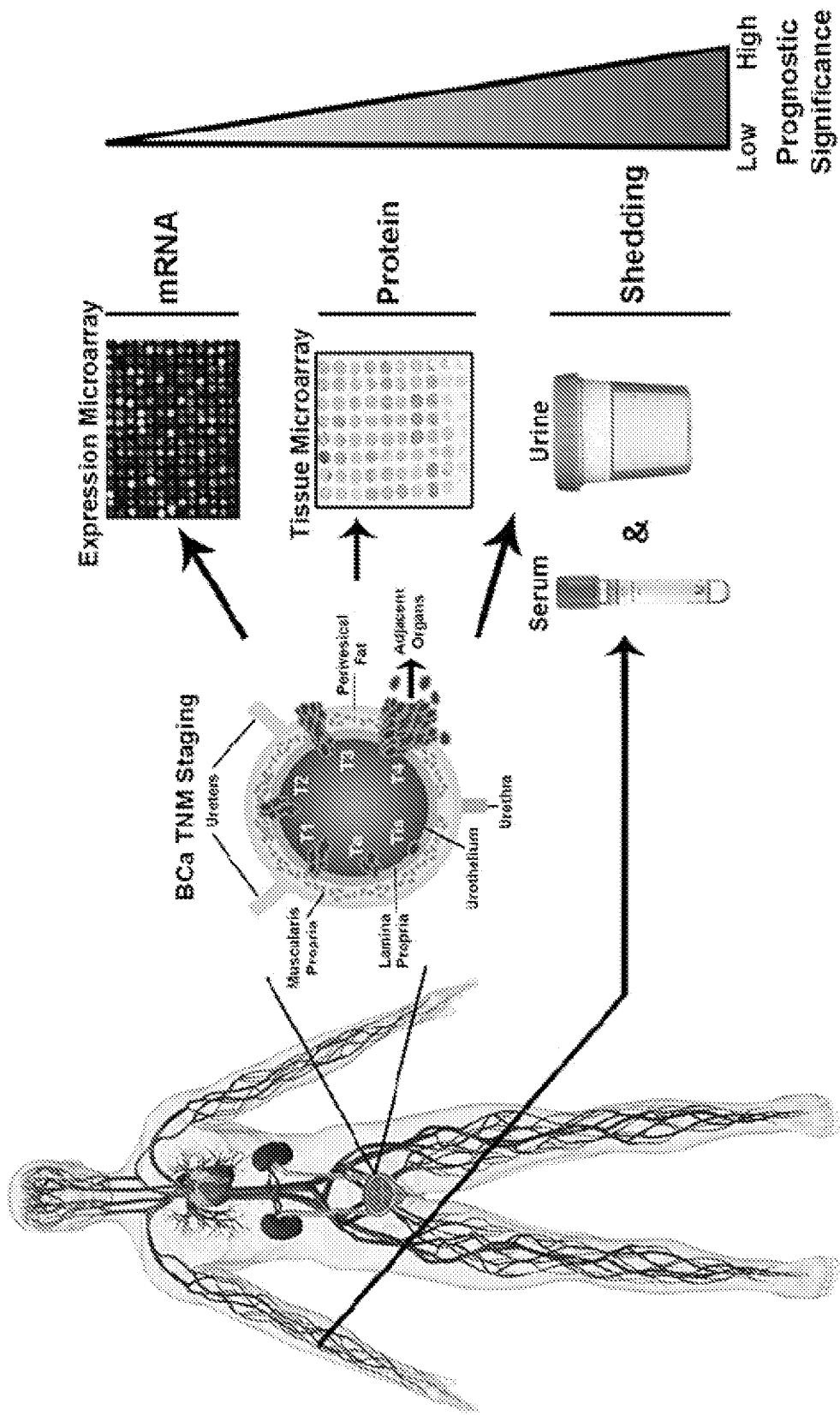
FIG. 12 shows a schematic of a multi-level approach for analysis of ALCAM in bladder cancer.

The current Example evaluates shed ALCAM as a prognostic biomarker in bladder cancer. In the bladder, ALCAM expression is restricted to the umbrella cells and several layers of the urothelium. Using retrospective cohort studies, the ability of ALCAM gene expression (mRNA), tissue expression (protein), and shedding (blood and urine) to predict overall survival in BCa were compared (FIG. 12). Since tumor cell motility is a central driver in tumor progression and metastasis, such molecular indicators that report on cell migration should act as surrogate markers of progression prior to overt clinical manifestation. This Example describes how Activated Leukocyte Cell Adhesion Molecule (ALCAM) promotes adhesion, while shedding of its extracellular domain is associated with migration.

Materials and Methods

Specimen Collection

All fluids were stored at −80° C. Tissues were processed as standard diagnostic blocks and stored in the Vanderbilt University Medical Center (VUMC, Nashville, Tenn.) tissue library.

ALCAM mRNA Cohort

NCBI Gene Expression Omnibus (GEO, GSE31684) was used to analyze ALCAM mRNA expression (probes 201951_at and 201952_at) in BCa and included 93 patients, representing stages pTa to pT4, who underwent radical cystectomy at Memorial Sloan-Kettering Cancer Center (New York, N.Y.) between 1993 and 2004. Median age of patients was 69.1 years, 73% were male, median follow-up was 32 months, and incidence of death was 70%.

ALCAM Expression Bladder Cancer TMA Cohort

Analysis of intra-tumoral ALCAM protein expression was performed on a retrospective cohort of patients with high-grade bladder cancer undergoing radical cystectomy at VUMC from 2000-2010. Tissue microarrays were constructed with matched adjacent normal, superficial (pTa and pTis/Cis) and invasive cores, when available. IHC and IF for ALCAM was performed on 651 total cores and analysis of overall survival was performed for those patients with a designated "invasive" core (n=198). Correlation of ALCAM expression with core pathology stage was performed on all unique cores (n=481) as described in statistical methods.

Shed ALCAM Bladder Cancer Cohort

The analysis of shed ALCAM in serum and urine was performed on a retrospective cohort of patients with high-grade bladder cancer undergoing radical cystectomy, which included pathological stages from pT0 to pT4 and excluded patients who had received chemotherapy prior to surgical resection (n=120).

Urine Control Cohorts

Age-matched, control clean-catch or catheter-derived urine specimens were collected at VUMC by the Cooperative Human Tissue Network. Three groups were collected: 1) Non-cancer control urines (Normal Controls) were collected from patients with no history or current diagnosis of cancer undergoing non-urologic surgeries including cardiac bypass, gastric bypass, thyroidectomy, esophagomyotomy, knee replacement, and hernia repair, 2) Inflammation control urines (Inflammation) were collected from patients with rectovaginal fistula, colorectal enteritis and ulceration, gallbladder polyploid cholesterolosis, endometriosis, atherosclerosis, ulcerative colitis, uterine fibroids, urethral stricture, and staghorn calculus, 3) Urine was collected from patients with cancers other than BCa (General Cancer), consisting of prostate, pancreatic, neuroendocrine, renal, and colorectal cancers.

Non-Cancer Serum Control Cohort

Serum from age-matched, non-cancer patients was collected from discarded clinical tests in the Vanderbilt Clinical Chemistry laboratory.

ALCAM Enzyme-Linked Immunosorbent Assay (ELISA)

Serum and urine were analyzed by human-specific ALCAM ELISA according to the manufacturer's protocol (R&D Systems, Minneapolis, Minn.). All samples were analyzed in duplicate at dilutions (Urine: 4-8 fold; Serum: 50-80 fold) that matched the dynamic range of the assay (0.05-4.00 ng/ml).

Immunohistochemistry (IHC) and Immunofluorescence (IF)

Immunohistochemistry (IHC) and immunofluorescence (IF) was performed on formalin-fixed paraffin-embedded cores (5 μm) on tissue microarrays. Sections were deparaffinized, hydrated, and peroxidase blocked (IHC only). Antigen retrieval was performed with citrate buffer (pH 6.0) for 15 minutes in a pressure cooker and sections were then blocked for 1 hour in 20% Aquablock (East Coast Biologics; North Berwick, Me.) plus 0.05% Tween-20. IHC was performed with mouse anti-ALCAM (MOG/07; Novocastra™, Leica Biosystems, Buffalo Grove, Ill.) followed by goat anti-mouse HRP (Jackson ImmunoResearch Laboratories Inc., West Grove, Pa.), counterstained with Hematoxylin, and mounted in Cytoseal™ XYL (Thermo Scientific, Richard-Allan Scientific, Waltham, Mass.). ALCAM IHC intensity was scored by a trained pathologist on a scale from 0-3 based on the signal observed in greater than 10% of tumor cells. IF was performed with mouse anti-ALCAM (MOG/07), rabbit anti-Ki67 (Clone SP6; Thermo Scientific, Rockford, Ill.), collagen binding CNA35, and Hoechst 33342. IF slides were mounted in ProLong Gold Antifade (Invitrogen, Carlsbad, Calif.). Fluorescence intensity, thresholded area, and colocalization were quantified in each TMA core by an Image J-based batch macro specifically written by our laboratory to quickly and efficiently set an intensity threshold for positive signal, identify the tissue area, define the region of interest, determine the percent thresholded area for each target within the region of interest, and determine percent colocalization of selected targets. Collagen staining was used to distinguish between the epithelial, stromal and muscular compartments in order to define the region of interest. Hoechst was used to define the nuclear compartment and to colocalize with Ki67. Percent thresholded area of ALCAM and percent nuclear area of Ki67 were subsequently used for analysis.

Statistical Analysis

Statistical analyses were performed at a two-tailed significance of 0.05. Kruskal-Wallis and Jonckheere-Terpstra test for trend analyses were used to assess the differences and overall trend between multiple independent groups followed by Mann-Whitney U post-tests if any significant differences were detected by Kruskal-Wallis. Generalized estimating equations (GEE) ordinal logistic regression and Kendall's rank correlation were used to assess correlations of non-independent samples. Kaplan-Meier curves and log-rank tests were utilized for univariable overall survival analysis. For multivariable analysis of censored survival, Cox proportional hazards regression was performed with all variables treated as continuous covariates. Time-dependent receiver operating characteristics (ROC) curves were used to assess the prognostic value of the Cox regression models. The area under the time-dependent ROC curves, as well as the concordance index was used to express the prognostic accuracy of the Cox regression models. In addition, the false positive rate and accuracy were determined at a fixed true positive rate of 75% at 12, 24, and 36 months of follow-up. Statistical analyses and graphing were performed with SPSS (IBM, Armonk, N.Y.), GraphPad Prism (GraphPad Software, Inc., La Jolla, Calif.) and R V2.14.1 for Windows (http://www.R-project.org). Bootstrap validation was performed via SPSS with a two-tailed significance, 1000 iterations and a Mersenne twister of 2,000,000. In addition, the concordance indices from the multivariable Cox regression models were validated in R with bootstrap method 0.632+.

Results

ALCAM Gene Expression does not Correlate with Progression and/or Patient Outcome in BCa.

ALCAM mRNA does not correlate with disease progression in BCa. Gene expression analyses performed on the Oncomine™ resource website (http://www.oncomine.org) of two independent bladder cancer cohorts comparing normal urothelium with superficial and invasive bladder cancer demonstrate that ALCAM expression is not significantly altered during BCa progression (Sanchez-Carbayo, n=157 and Lee, GSE13507, n=256).

Figure 13A:
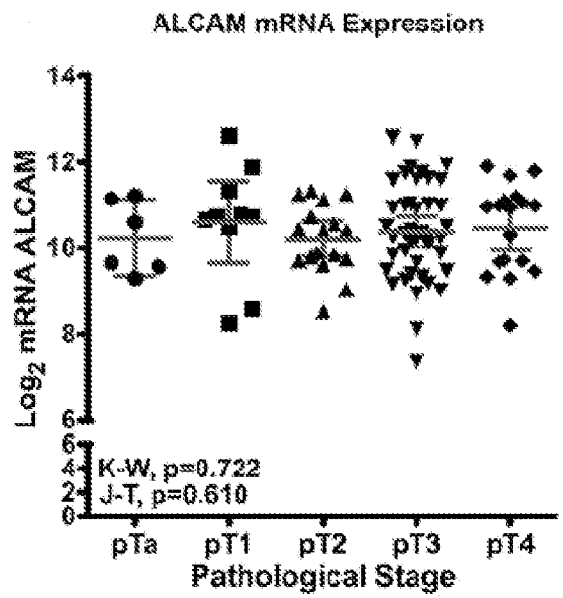
FIG. 13 shows the correlation of ALCAM mRNA with tumor stage and overall survival in bladder cancer. (A) ALCAM $Log_2$ mRNA levels are graphed according to tumor pathology stage. Mean and 95% confidence intervals displayed. K-W, Kruskal-Wallis test. J-T, Jonckheere-Terpstra test for trend. (B) Kaplan-Meier curves and Log-rank test for significance of ALCAM dichotomized high/low around the median $Log_2$ mRNA level (10.4). HR, Hazard Ratio. CI, Confidence Interval. All analyses were two-tailed with a 0.05 alpha level.
Figure 13B:
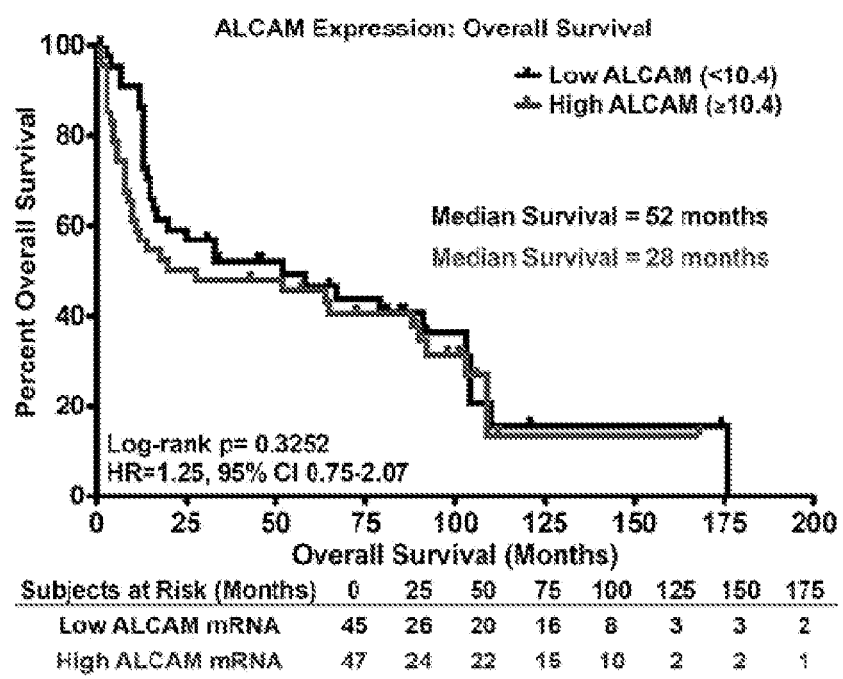

To further determine if ALCAM mRNA expression correlated with outcome in BCa, a detailed statistical analysis of a publicly available microarray dataset was performed (GSE31684). ALCAM mRNA expression did not correlate with tumor stage (FIG. 13A; Kruskal-Wallis (K-W), P=0.722; Jonckheere-Terpstra test for trend (J-T), P=0.610), nor did it significantly stratify patient outcome of overall survival (FIG. 13B; Log-rank, p=0.3252; Hazards Ratio (HR), 1.25; 95% Confidence Interval (CI), 0.75-2.07). Furthermore, multivariable Cox regression analysis reveals that ALCAM gene expression is not an independent predictor of 3-year overall survival after adjusting for available indicators including age, gender and tumor stage (Table 3; adjusted HR, 1.26; 95% CI, 0.943-1.682; p=0.118). Since ALCAM mRNA levels remain unaltered during tumor progression in three independent patient cohorts and fail to predict overall survival by univariable and multivariable analyses, it appears that ALCAM gene expression is not a viable biomarker for BCa prognosis.

TABLE 3

Assessment of ALCAM mRNA expression as a predictor in a multivariable Cox regression analysis of 3-year overall survival in bladder cancer.

| | Hazard Ratio | 95.0% CI | Significance | Bootstrap Significance |
|---|---|---|---|---|
| Age (Years) | 1.012 | 0.984-1.042 | 0.404 | 0.384 |
| Gender | 1.315 | 0.699-2.477 | 0.396 | 0.383 |
| Tumor Stage | 2.457 | 1.686-3.580 | <0.0001 | 0.001 |
| ALCAM Log2 mRNA | 1.260 | 0.943-1.682 | 0.118 | 0.107 |

Assessment of ALCAM mRNA expression as a predictor of 3-year overall survival by multivariable Cox regression analysis of the NCBI Gene Expression Omnibus (GEO) [GSE31684] dataset. Hazard Ratio is the adjusted hazards ratio, CI=confidence interval, bootstrap significance is two-tailed with 1000 iterations and a Mersenne twister of 2,000, 000.

ALCAM Protein Expression Inversely Correlates with BCa Progression but Fails to Predict Outcome Post-translational proteolytic processing of ALCAM can create a disparity between gene expression and the availability of ALCAM protein. Indeed, ALCAM levels can fail to correlate with gene transcription. To determine if protein expression of ALCAM in BCa correlates with tumor stage and/or patient outcome, immunohistochemistry (IHC) on tissue microarrays (TMAs) constructed of high-grade BCa specimens collected during cystectomy were performed (Table 4). ALCAM IHC intensity was scored (0-3).

TABLE 4

Bladder cancer TMA ALCAM expression cohort descriptors and frequencies.

|  | Minimum | Maximum | Mean | Median | 95% CI |
|---|---|---|---|---|---|
| Age (Years) | 17 | 94 | 66 | 67 | 66-70 |
| ALCAM Intensity Score (IHC) | 0.0 | 3.0 | 0.8 | 0.0 | 0.00-0.50 |
| ALCAM % Thresholded Area (IF) | 0.0 | 72.8 | 6.6 | 1.6 | 0.9-2.1 |
| Ki67 % Nuclear Area (IF) | 0.0 | 11.6 | 1.5 | 1.1 | 0.9-1.3 |
| Follow-up (Months) | 0.3 | 104.1 | 33.4 | 25.3 | 19.0-32.6 |
| Time to Death (Months) | 0.3 | 67.7 | 18.4 | 14.1 | 12.2-16.7 |

|  | Frequency | Percent |
|---|---|---|
| Gender |  |  |
| Female | 42 | 21.2% |
| Male | 156 | 78.8% |
| Race |  |  |
| White | 185 | 93.4% |
| Asian | 1 | 0.5% |
| Black | 9 | 4.5% |
| Other | 3 | 1.5% |
| Death | 130 | 65.7% |
| Pathological Tumor Stage |  |  |
| pTa | 1 | 0.5% |
| pTis | 1 | 0.5% |
| pT1 | 21 | 10.6% |
| pT2a | 34 | 17.2% |
| pT2b | 37 | 18.7% |
| pT3a | 42 | 21.2% |
| pT3b | 31 | 15.7% |
| pT4a | 30 | 15.2% |
| pT4b | 1 | 0.5% |
| N Stage |  |  |
| N0 | 141 | 71.2% |
| N1 | 21 | 10.6% |
| N2 | 36 | 18.2% |
| Total Patients Analyzed (Invasive Cores) | 198 | 35.4% |
| Core Stage |  |  |
| Normal | 141 | 29.3% |
| pTa | 27 | 5.6% |
| pTis | 117 | 24.3% |
| pT1 | 21 | 4.4% |
| pT2 | 71 | 14.8% |
| pT3 | 73 | 15.2% |
| pT4 | 31 | 6.4% |
| Total Unique Cores Analyzed | 481 | 100.0% |

Description of the bladder cancer TMA patient cohort (patients = 198, cores = 481) used for prognostic assessment of ALCAM expression by immunohistochemistry and immunofluorescence. Only patients with invasive cores (n = 198) were utilized for overall survival analysis while all unique cores (n = 481) were used in the correlation of ALCAM expression with core stage.

Figure 14A:
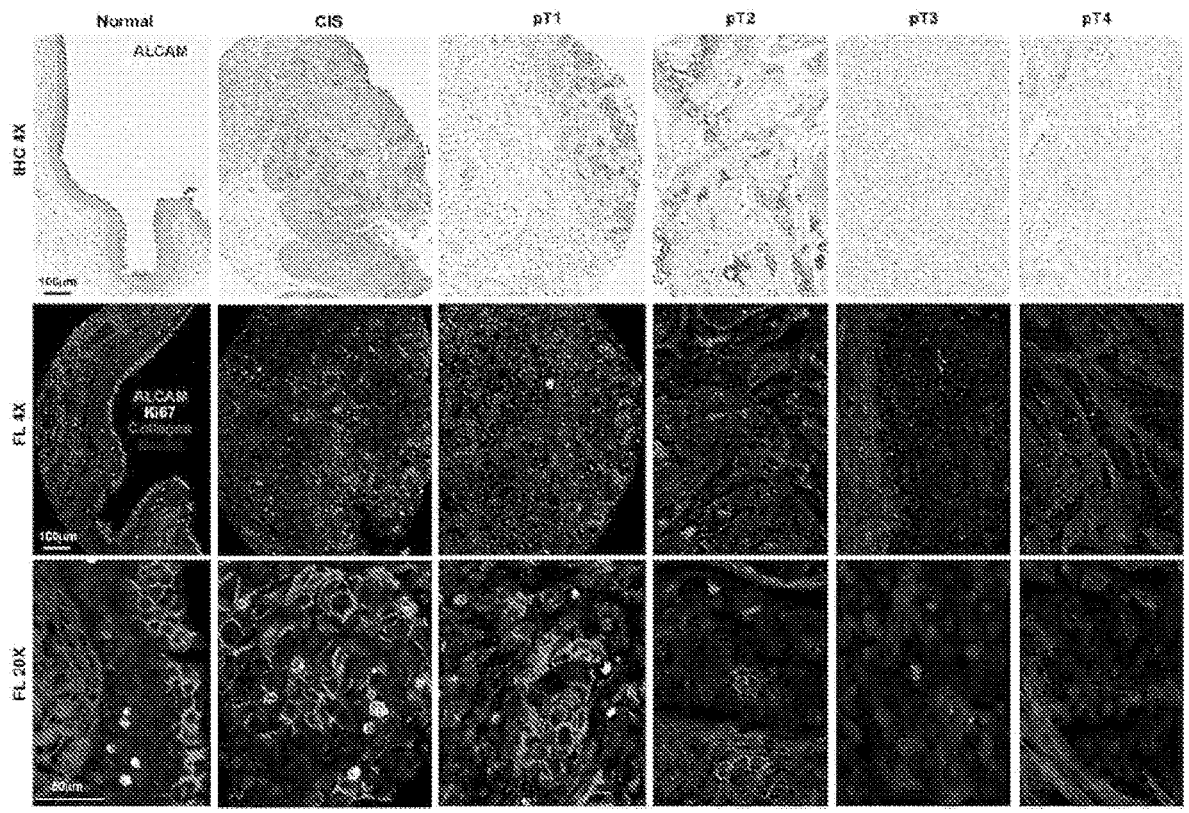
FIG. 14 shows the correlation of ALCAM protein expression with tumor stage and overall survival in bladder cancer. (A) IHC (top panel) for ALCAM (brown) and IF (bottom panels) for ALCAM (green), Ki67 (white), Collagen (red), and Nuclei (blue) in normal bladder and BCa (CIS, pT1, pT2, pT3, pT4). Scale bars=100 µm (low magnification) and 50 µm (high magnification). (B, D, F) Correlation of core stage (n=481) with ALCAM IHC intensity score (B), ALCAM IF percent thresholded area (D), and Ki67 IF percent nuclear area (F) with GEE ordinal logistic regression (OR, odds ratio; with 95% CI) and Kendall's (K) rank correlation (τ). Mean and 95% CI graphed. (C, E, G) Kaplan-Meier curves and Log-rank tests for overall survival (n=198) with ALCAM IHC expression dichotomized around an intensity score of 2 (C), ALCAM IF expression dichotomized around the mean percent thresholded area of 6.66% (E), and Ki67 IF dichotomized around the mean percent nuclear area of 1.58% (G). HR, Hazard Ratio. CI, Confidence Interval. All analyses were two-tailed with a 0.05 alpha level.
Figure 14B:
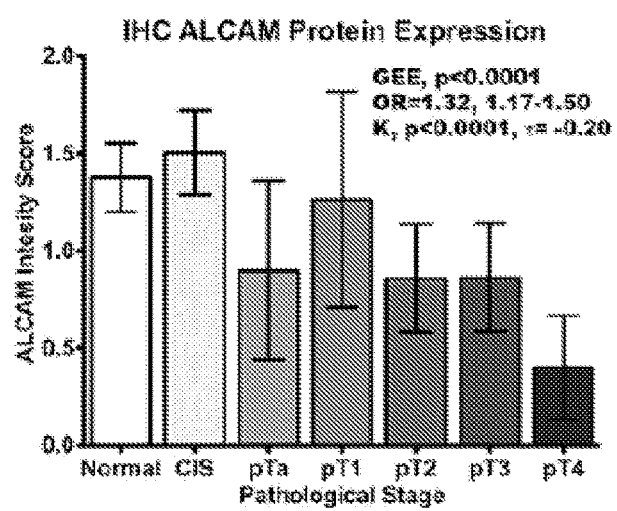
Figure 14C:
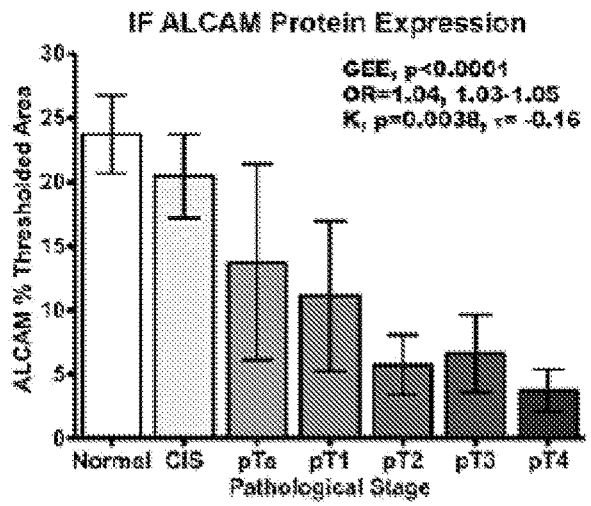
Figure 14D:
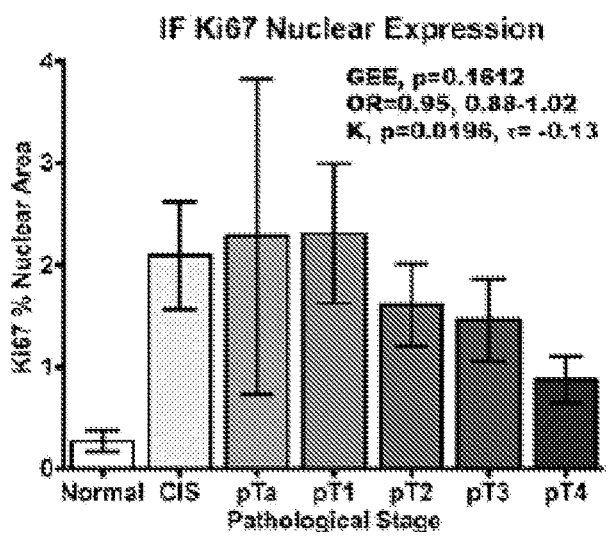
Figure 14E:
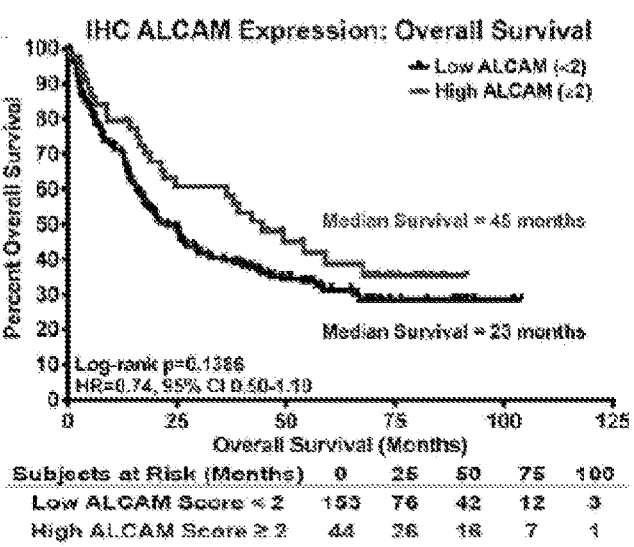

In normal bladder, ALCAM expression was confined to the urothelium (FIG. 3A, IHC). In non-invasive carcinoma in situ, the expansion of the urothelium led to an increase in ALCAM positive cells with no increase in signal intensity (FIG. 14A, IHC). However, concomitant with the appearance of an invasive phenotype, ALCAM expression diminished in the progression from pT1 to pT4 (FIG. 14A, IHC). Since each patient had multiple cores representing several pathological stages and, thus, had non-independent samples, the correlation of the mean ALCAM intensity score with pathological core stage was analyzed with generalized estimating equations (GEE) ordinal logistic regression and Kendall's rank correlation (K) (n=481). Based on these analyses, the mean ALCAM intensity score was significantly and inversely correlated with core stage, demonstrating a loss of ALCAM detection with advanced stage (FIG. 14B; K, τ=−0.20; p<0.0001; GEE Odds Ratio (OR), 1.32; 95% CI, 1.17-1.50; p<0.0001). Overall survival analysis was subsequently performed using only invasive core values to ensure samples were independent (n=198). Kaplan-Meier curves show separation when the mean ALCAM intensity score was dichotomized around 2, but a significant difference was not detected (FIG. 14C; Log-Rank, p=0.1386; HR, 0.74; 95% CI, 0.50-1.10). Furthermore, mean ALCAM intensity score was not a significant predictor of overall survival when adjusted for age, gender, tumor stage and lymph node status by multivariable cox regression analysis (Table 5; adjusted HR, 0.937; 95% CI, 0.780-1.125; p=0.483).

TABLE 5

Assessment of immunohistochemistry ALCAM expression as predictor in multivariable Cox regression analysis of 3-year overall survival in TMA bladder cancer cohort.

|  | Hazard Ratio | 95.0% CI | Significance | Bootstrap Significance |
|---|---|---|---|---|
| Age (Years) | 1.027 | 1.007-1.048 | 0.010 | 0.020 |
| Gender | 0.795 | 0.512-1.236 | 0.308 | 0.343 |
| Tumor Stage | 1.284 | 1.107-1.490 | 0.001 | 0.004 |
| N Stage | 1.414 | 1.103-1.813 | 0.006 | 0.016 |
| Mean ALCAM Intensity Score | 0.937 | 0.780-1.125 | 0.483 | 0.481 |

Assessment of ALCAM expression, measured by IHC intensity scoring (0-3), as a predictor of 3-year overall survival by multivariable Cox regression analysis.
Hazard Ratio is the adjusted hazards ratio,
CI = confidence interval,
bootstrap significance is two-tailed with 1000 iterations and a Mersenne twister of 2,000,000.

To verify that the inability of ALCAM expression to predict overall survival in BCa is not due to the narrow nature of an ordinal scoring method, immunofluorescence (IF) for ALCAM was used to generate a continuous measurement of ALCAM protein expression (FIG. 14, FL). The degree of ALCAM staining was quantified as described in the methods. Collagen staining was used to visualize the tissue architecture. The final readout for ALCAM was a continuous variable defined as the area within the region of interest that was above background (% thresholded area; range 0-72.8%). Similar to the IHC results, IF staining of ALCAM was significantly and inversely correlated with core stage (FIG. 14D; K, τ=−0.16; p=0.0038; GEE OR, 1.04; 95% CI, 1.03-1.05; p<0.0001) but failed to correlate with overall survival when percent thresholded area was dichotomized around the mean of 6.66% (FIG. 14E; Log-Rank, p=0.4125; HR, 1.18; 95% CI, 0.79-1.76). Most importantly, ALCAM IF was not a significant predictor of overall survival when adjusted for age, gender, tumor stage and lymph node status by multivariable Cox regression analysis (Table 6; top model; adjusted HR, 1.001; 95% CI, 0.987-1.016; p=0.843). These observations demonstrate that, in spite of a strong correlation between ALCAM protein detection and tumor stage, ALCAM expression fails to correlate with or predict patient outcome.

TABLE 6

Assessment of immunofluorescence ALCAM and Ki67 expression as predictor in multivariable Cox regression analysis of 3-year overall survival in TMA bladder cancer cohort.

|  | Hazard Ratio | 95.0% CI | Significance | Bootstrap Significance |
|---|---|---|---|---|
| Age (Years) | 1.027 | 1.006-1.048 | 0.010 | 0.024 |
| Gender | 0.779 | 0.503-1.208 | 0.265 | 0.304 |
| Tumor Stage | 1.295 | 1.116-1.501 | 0.001 | 0.001 |
| N Stage | 1.416 | 1.104-1.815 | 0.006 | 0.017 |
| ALCAM (% Thresholded Area) | 1.001 | 0.987-1.016 | 0.843 | 0.792 |
| Age (Years) | 1.027 | 1.006-1.048 | 0.010 | 0.026 |
| Gender | 0.783 | 0.505-1.216 | 0.277 | 0.307 |
| Tumor Stage | 1.364 | 1.170-1.589 | <0.0001 | 0.001 |
| N Stage | 1.433 | 1.114-1.842 | 0.005 | 0.014 |
| ALCAM (% Thresholded Area) | 1.001 | 0.986-1.016 | 0.928 | 0.913 |
| Ki67 (% Nuclear Area) | 1.202 | 1.077-1.341 | 0.001 | 0.001 |

Assessment of ALCAM expression, measured by IF percent thresholded area, and Ki67 percent nuclear area as predictors of 3-year overall survival by multivariable Cox regression analysis.
Hazard Ratio is the adjusted hazards ratio,
CI = confidence interval,
bootstrap significance is two-tailed with 1000 iterations and a Mersenne twister of 2,000,000.

Figure 14F:
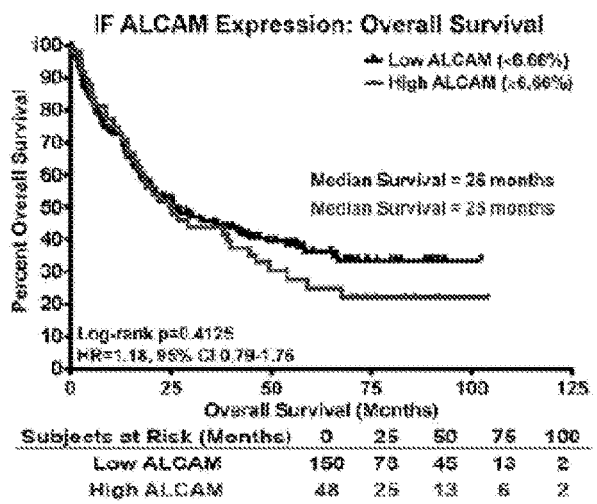
Figure 14G:
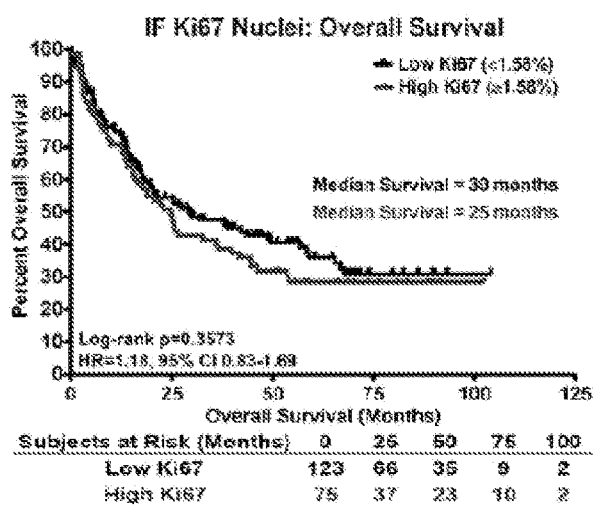

To confirm that the BCa TMA cohort was generalizable and that the model behaved according to published observations, Ki67 was assessed as a marker of cell proliferation and a known indicator of outcome in BCa. Ki67 was quantified by measuring the amount of nuclear area that was colocalized with Ki67 within the ROI (% nuclear area). Consistent with the importance of proliferation in tumor progression, Ki67 staining was elevated in tumor compared to adjacent normal tissue (FIG. 14F). Furthermore, Ki67 was a significant independent predictor of overall survival when adjusted for age, gender, tumor stage and lymph node status (Table 6; bottom model; adjusted HR, 1.20; 95% CI, 1.077-1.341; p=0.001) despite the fact that by univariable analysis it was unable to discern patient outcome when dichotomized above and below the mean (FIG. 14G; Log-Rank, p=0.3573; HR, 1.18; 95% CI, 0.83-1.69). This Ki67 data demonstrates that the current BCa TMA cohort is representative of the general population and that the analysis was consistent with accepted clinical practice and published studies, which validates that ALCAM protein expression does not appear to independently predict overall survival in BCa.

Figure 15A:
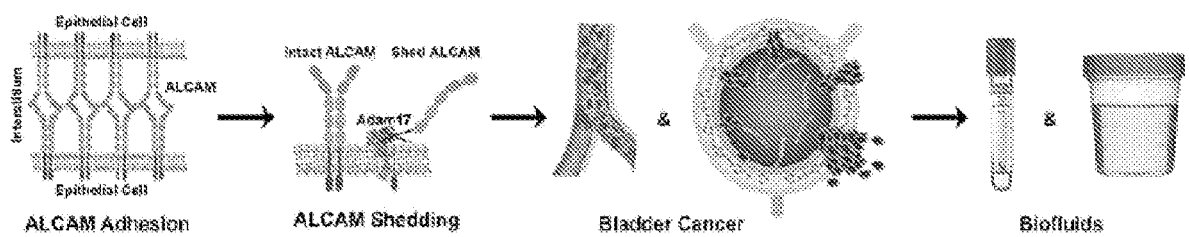
FIG. 15 shows the detection of shed ALCAM in fluids and its correlation with stage and overall survival in bladder cancer. (A) A schematic of ALCAM acting as a cell-cell adhesion molecule in normal epithelial cells, which, during tumor progression, cells can regulate motility and invasion through ADAM17-mediated ALCAM cleavage. (B) ALCAM levels (ng/ml) in serum of normal controls compared to patients with BCa. Mann-Whitney U, two-tailed, 0.05 alpha level. (C) ALCAM levels (ng/ml) in urine of normal controls compared to patients with inflammatory conditions, cancers other than BCa, and BCa. Mann-Whitney U, two-tailed, 0.05 alpha level. UC, ulcerative colitis. SC, staghorn calculi. (D,E) Correlation of shed ALCAM in the serum (D) and urine (E) with pathological tumor stage in the shed ALCAM BCa cohort (n=120). K-W, Kruskal-Wallis test. J-T, Jonckheere-Terpstra test for trend. Graphs display mean and 95% CI. Kaplan-Meier curves and Log-rank tests for analysis of overall survival with (F) tumor stage, (G) urine ALCAM, and (H) serum ALCAM. (I) Graph of the time-dependent receiver operating characteristic (ROC) curves based on the probabilities attained by the multivariable Cox regression analysis for age, tumor stage, and N-stage alone (red) compared to the addition of serum and urine ALCAM (blue). Concordance indices (C-Index) are shown.

ALCAM Shedding into Urine is Significantly and Specifically Elevated in BCa Patients Since ALCAM protein is reduced without a concomitant reduction in gene expression (FIG. 13A vs. FIGS. 14C and 14D), without being bound by theory or mechanism, the loss of ALCAM in BCa tissue may be due to proteolytic shedding of the ectodomain, which can be cleaved by ADAM17. Consequently, shed ALCAM should be detectable in tumor-adjacent fluids such as serum and urine (FIG. 15A).

Figure 15B:
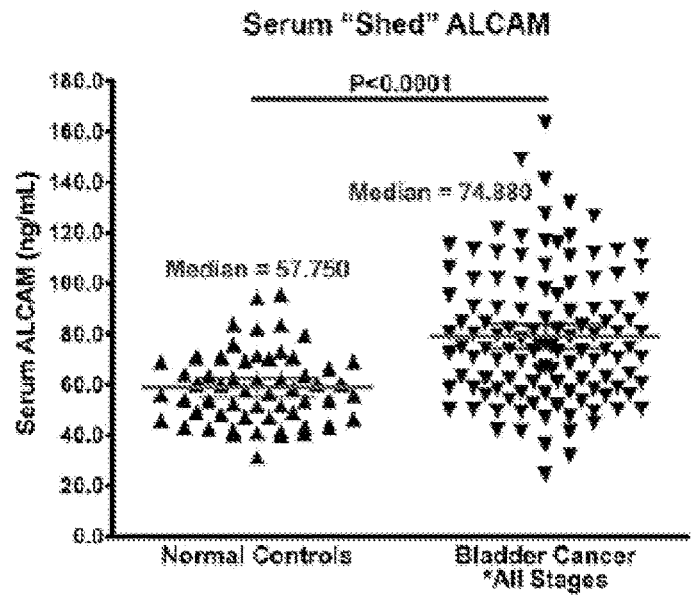
Figure 15C:
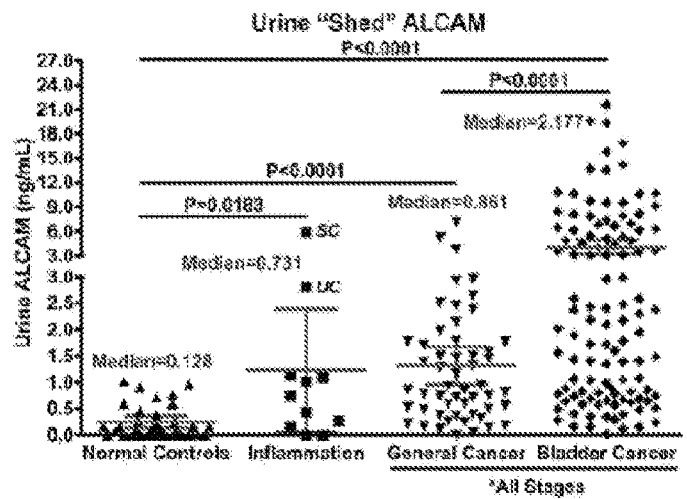

Serum and urine ALCAM levels were analyzed from patients in four distinct cohorts including: 1) patients undergoing surgery but with no cancer (Normal Controls), 2) patients with inflammatory diseases (Inflammation), 3) patients with non-bladder malignancies (General Cancer) and 4) patients with BCa (Bladder Cancer). Analysis of serum ALCAM revealed that it was significantly elevated (1.3-fold) in patients with BCa compared to Normal Controls (FIG. 15B; median 74.88 vs. 57.75 ng/ml; P<0.0001). Moreover, the detection of ALCAM in urine was dramatically elevated (17.0-fold) in BCa patients compared to normal controls (FIG. 15C; median 2.18 vs. 0.13 ng/ml; P<0.0001). Urinary ALCAM levels were also measured for patients with inflammatory diseases or other cancers to confirm that the significant elevation of urine ALCAM was specific to the presence of BCa. These non-BCa urines were found to be slightly elevated when compared to normal controls (median 0.73 and 0.86 vs. 0.13 ng/ml; P=0.0183 and P<0.0001) but contained significantly less ALCAM than urine from BCa patients (P<0.0001)(FIG. 15C).

Quality control assays were performed to ensure that a clinical test of ALCAM would be sufficiently robust and reproducible. Specifically, the stability of ALCAM in serum and urine specimens was assessed by measuring ALCAM levels by ELISA before and after two freeze-thaw cycles. Samples were thawed at 4-degrees Celsius for three days, re-froze, and then re-thawed on ice just prior to use. Pre- and post-freeze-thaw ALCAM levels were assessed by calculating fold-change. The influence of catheterization on urine ALCAM levels was assessed by analyzing urine ALCAM in patient-matched clean catch and foley specimens collected just prior to and during surgery, respectively. A paired t-test was performed to detect any differences in the matched samples. Reproducibility of the detection of urine ALCAM was assessed by repeating the ELISA on two separate aliquots over two runs separated by more than six months. A Spearman correlation was performed to determine the similarity between each run. Urinary ALCAM measurements were not significantly influenced by repeated freeze-thaw, collection method (foley-derived vs. clean catch urine), or repeated sampling (Spearman coefficient, 0.86; P<0.0001). In addition, correction for dehydration, proteinuria, and hematuria in the urine by normalizing urinary ALCAM to specific gravity, creatinine, and hemoglobin did not significantly altered the ranking of patients within the cohort in regard to urinary ALCAM levels (Spearman correlation coefficients: hemoglobin, 0.9962; specific gravity, 0.9996; creatinine, 0.7939; all P<0.0001). Consequently, the raw urine ALCAM levels were utilized in all subsequent analyses.

In this regard, Urine ALCAM levels were normalized to urinary total protein (Thermo Scientific, BCA, 23227), creatinine (Enzo Life Sciences, 937-001), specific gravity (Siemens Medical Solutions Diagnostics, Multistix® 8 SG, 2164) and hemoglobin (Sigma-Aldrich, Drabkin's Reagent, D5941) in an attempt to control for dehydration, proteinuria, and hematuria. BCA analysis for total protein in urine was unreliable due to the presence of urea. Spearman correlations were performed to compare un-corrected, raw urine ALCAM levels with hemoglobin, specific gravity, and creatinine-corrected urine ALCAM levels.

Urinary ALCAM is an Independent Predictor of Overall Survival in BCa

Since both serum and urine ALCAM were elevated in BCa, the next step was to determine if shed ALCAM correlated with tumor stage, and whether shed ALCAM could improve the prediction of patient outcome (overall survival) when combined with known clinical indicators and, thus, could serve as a novel and clinically meaningful prognostic biomarker.

Figure 15D:
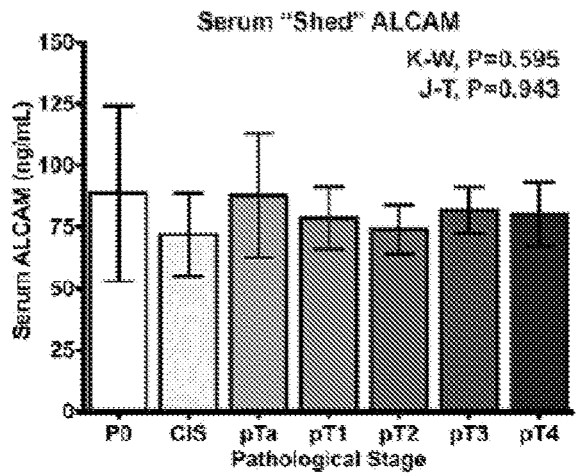
Figure 15E:
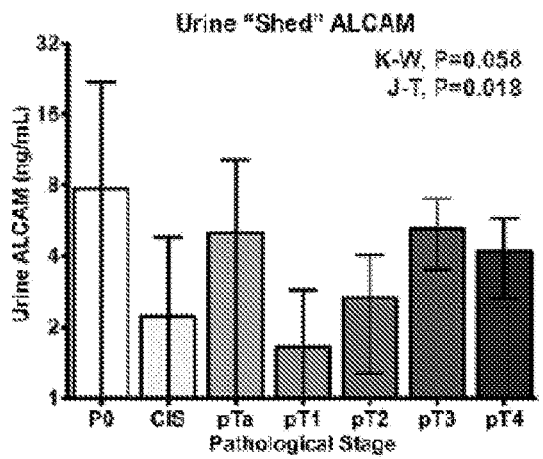
Figure 15F:
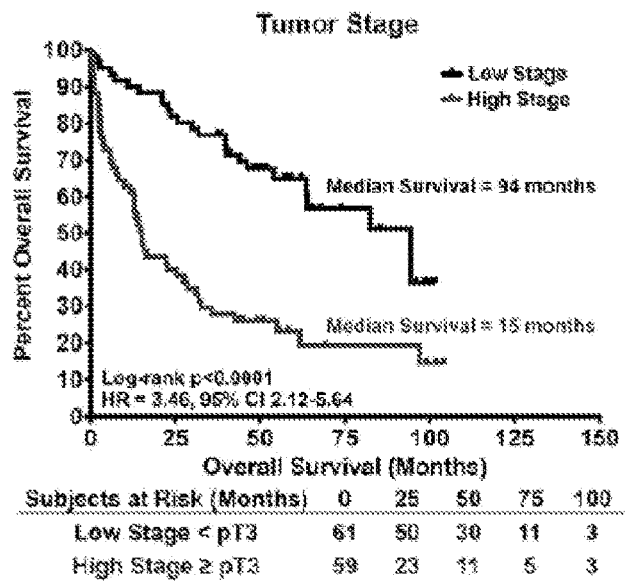
Figure 15G:
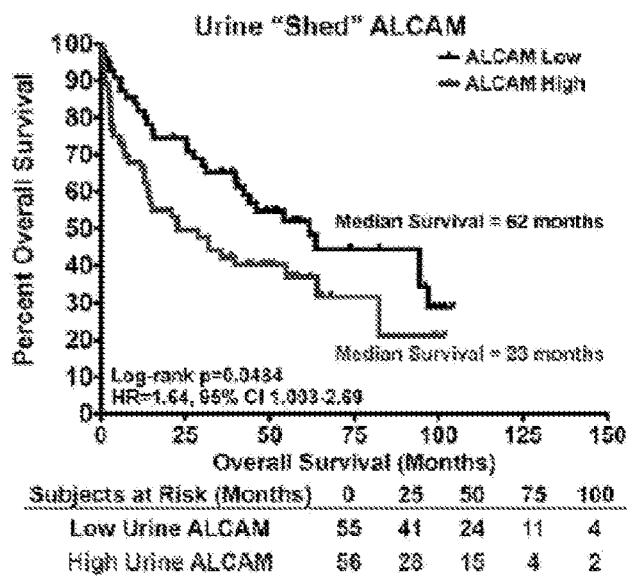
Figure 15H:
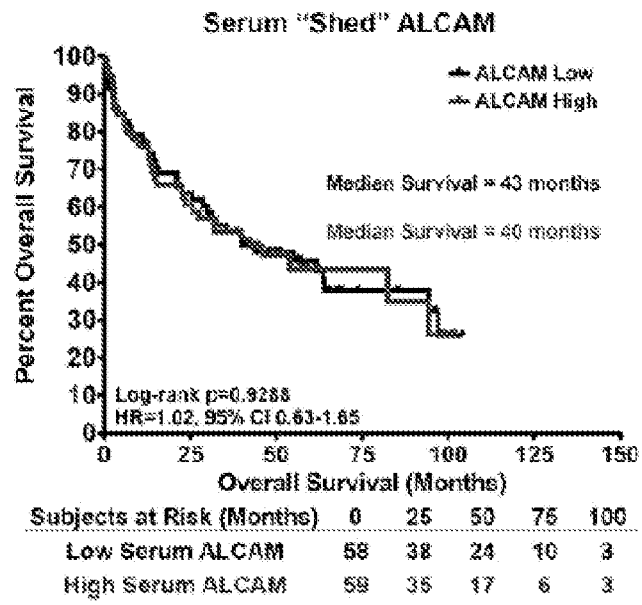

A retrospective analysis of shed ALCAM in serum and urine was performed to determine if shed ALCAM correlated with disease progression and could function as an independent predictor of survival. Pre-operation serum and urine from patients with high grade BCa were analyzed by ALCAM ELISA (Table 7, n=120). Serum ALCAM levels did not correlate with pathological tumor stage (FIG. 15D; Kruskal-Wallis (K-W), P=0.595; Jonckheere-Terpstra test for trend (J-T), P=0.943). Urine ALCAM levels were not significantly different between tumor stages but did show a significant positive trend (FIG. 15E; K-W P=0.058; J-T, P=0.018), suggesting that ALCAM levels in the urine increase as tumors become more invasive. Next, overall survival was plotted for tumor stage, urine ALCAM and serum ALCAM (FIG. 15F-H). As expected, advanced tumor stage (≥pT3, high stage) significantly correlated with decreased survival (FIG. 15F; median overall survival (OS), 94 vs. 15 months; Log-Rank, p<0.0001; HR, 3.46; 95% CI, 2.12-5.64). Urinary ALCAM dichotomized around the median of 2.18 ng/ml also significantly stratified patients into high and low risk of death (FIG. 15G; median OS, 62 vs. 23 months; Log-Rank, 0.0484; HR, 1.64; 95% CI, 1.003-2.69). However, serum ALCAM dichotomized around the median of 74.88 ng/ml did not correlate with overall survival (FIG. 15H; Log-Rank, 0.9288; HR, 1.02; 95% CI, 0.63-1.65).

TABLE 7

Bladder cancer "shed" ALCAM cohort descriptors and frequencies.

|  | Minimum | Maximum | Mean | Median | 95% CI |
|---|---|---|---|---|---|
| Age (Years) | 35 | 89 | 68 | 69 | 66-70 |
| Serum ALCAM (ng/ml)[A] | 24.6 | 163.5 | 79.2 | 74.9 | 70.6-81.0 |
| Urine ALCAM (ng/ml)[B] | 0.018 | 21.6 | 4.0 | 2.2 | 1.5-3.0 |
| Follow-up (Months) | 0.3 | 104.2 | 38.0 | 38.1 | 25.7-44.1 |
| Time to Death (Months) | 0.3 | 97.1 | 22.9 | 14.6 | 10.9-22.6 |

|  | Frequency | Percent |
|---|---|---|
| Gender |  |  |
| Female | 12 | 10.0% |
| Male | 108 | 90.0% |
| Race |  |  |
| White | 115 | 95.8% |
| Black | 3 | 2.5% |
| Unknown | 2 | 1.7% |
| Death | 71 | 59.2% |
| Pathological Tumor Stage |  |  |
| pT0 | 5 | 4.2% |
| pTa | 8 | 6.7% |
| pTis | 9 | 7.5% |
| pT1 | 8 | 6.7% |
| pT2a | 20 | 16.7% |
| pT2b | 11 | 9.2% |
| pT3a | 31 | 25.8% |
| pT3b | 9 | 7.5% |
| pT4a | 19 | 15.8% |
| N Stage |  |  |
| N0 | 90 | 75.0% |
| N1 | 6 | 5.0% |
| N2 | 24 | 20.0% |
| Group |  |  |
| NMIBC | 30 | 25.0% |
| OCMIBC | 29 | 24.2% |
| EVMIBC | 31 | 25.8% |
| LN+ | 30 | 25.0% |
| Total Patients Analyzed | 120 | 100.0% |

Description of the bladder cancer patient cohort (n = 120) used for prognostic assessment of shed ALCAM in serum and urine.
[A]3 specimens missing for analysis,
[B]9 specimens missing for analysis,
CI = confidence interval,
NMIBC = non-muscle invasive BCa,
OCMIBC = organ-confined muscle invasive BCa,
EVMIBC = extravesical muscle invasive BCa,
LN+ = lymph-node positive muscle invasive BCa.

Figure 15I:
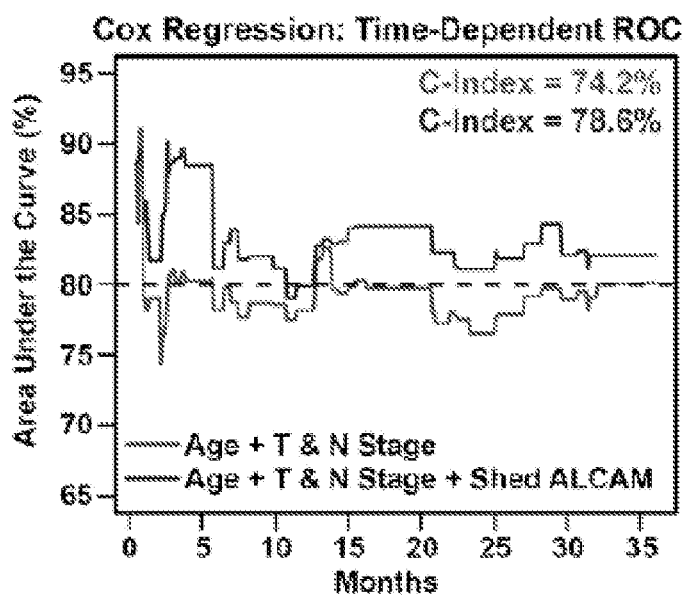

To determine if serum and/or urine ALCAM were independent predictors of overall survival, a multivariable Cox regression analyses was performed. This cohort, by nature, is 95.8% white and 90.0% male, leading to exclusion of race and gender from all multivariable analyses. After adjusting for age, tumor stage, and lymph node status, urine ALCAM, but not serum ALCAM, was a significant independent predictor of 3-year overall survival (Table 8; adjusted HR, 1.10; 95% CI 1.043-1.164, P=0.001). Age and tumor stage were also independent predictors of 3-year overall survival while lymph node status approached significance (Table 8; P<0.0001, P=0.001, P=0.064). The ability of serum and urine ALCAM to improve the prediction of 3-year overall survival when compared to age, tumor stage and lymph node status alone was assessed with a time-dependent receiver operating characteristics curve based on multivariable Cox regression analysis. Prediction measurements were substantially improved by including both serum and urine ALCAM in the model where the concordance index (C-Index) increased 4.4% from 74.2% with age, tumor stage and lymph node status alone to 78.6% with the inclusion of serum and urine ALCAM (FIG. 15I and Table 9). The addition of serum and urine ALCAM led to improvements in standard prediction measures such as area under the curve (AUC), true positive rate (TPR), false positive rate (FPR), and accuracy at 1-year intervals (Table 9). Of note, at 12 months of follow-up, when the TPR is set at 75.0%, the FPR is reduced by 10.2% and the accuracy is increased by 5.7% (Table 9).

TABLE 8

Assessment of "shed" ALCAM as a predictor in a multivariable Cox regression analysis of 3-year overall survival in bladder cancer.

|  | Hazard Ratio | 95.0% CI | Significance | Bootstrap Significance |
|---|---|---|---|---|
| Age (Years) | 1.068 | 1.034-1.103 | <0.0001 | 0.001 |
| Tumor Stage | 1.397 | 1.155-1.689 | 0.001 | 0.002 |
| N Stage | 1.432 | 0.979-2.095 | 0.064 | 0.076 |
| Serum ALCAM (ng/ml) | 0.995 | 0.984-1.006 | 0.374 | 0.340 |
| Urine ALCAM (ng/ml) | 1.102 | 1.043-1.164 | 0.001 | 0.001 |

Assessment of shed ALCAM, serum and urine, as a predictor of 3-year overall survival by multivariable Cox regression analysis.
Hazard Ratio is the adjusted hazards ratio,
CI = confidence interval,
bootstrap significance is two-tailed with 1000 iterations and a Mersenne twister of 2,000,000.

TABLE 9

Overall survival (3-year) multivariable model prediction performance with the addition of "shed" ALCAM.

|  | Age + Tumor and N Stage | Age + Tumor and N Stage + Serum ALCAM + Urine ALCAM | Difference |
|---|---|---|---|
| C-Index (%) | 74.2 | 78.6 | 4.4 |
| Bootstrap Significance [0.632 Method] (%) | 75.3 | 77.8 | 2.7 |
| 12 (Months) |  |  |  |
| AUC | 78.2 | 79.9 | 1.7 |
| 95.0% CI | 71.4-86.6 | 71.7-87.8 |  |
| TPR (%) | 74.8 | 75.2 | 0.4 |
| FPR (%) | 35.5 | 25.3 | -10.2 |
| Accuracy (%) | 69.3 | 75 | 5.7 |
| 24 (Months) |  |  |  |
| AUC | 76.6 | 81.1 | 4.5 |
| 95.0% CI | 72.8-87.4 | 75.6-89.3 |  |
| TPR (%) | 75.3 | 75.8 | 0.5 |

TABLE 9-continued

Overall survival (3-year) multivariable model prediction performance with the addition of "shed" ALCAM.

|  | Age + Tumor and N Stage | Age + Tumor and N Stage + Serum ALCAM + Urine ALCAM | Difference |
|---|---|---|---|
| FPR (%) | 36.2 | 28.6 | −7.6 |
| Accuracy (%) 36 (Months) | 69.2 | 73.4 | 4.2 |
| AUC | 80.1 | 82.1 | 2.0 |
| 95.0% CI | 76.4-90.1 | 77.0-91.0 |  |
| TPR (%) | 75.4 | 74.8 | −0.6 |
| FPR (%) | 28.9 | 26.5 | −2.4 |
| Accuracy (%) | 73.1 | 74.1 | 1.0 |

Prediction parameters for biomarker assessment of 3-year overall survival analysis based on multivariable cox regression;
Bootstrap validation was performed according to the .632+ method [27].
C-Index = concordance index,
AUC = area under the curve of a receiver operating characteristics curve;
TPR = true positive rate;
FPR = false positive rate ALCAM can dynamically regulate cell motility through homotypic intracellular adhesions, which can be disrupted by the protease ADAM17. Therefore, the shed ectodomain of ALCAM is a molecular marker of cell motility. The ectodomain of ALCAM appears to be lost from the BCa tissue during malignant progression (FIG. 14), while urinary ALCAM levels rise and correlate with poor outcome (FIG. 15). Further statistical interrogation demonstrates that urinary ALCAM is a significant independent predictor of overall survival after adjusting for age, tumor stage and lymph node status (Table 8) and improves accuracy of prediction by 4.4% (FIG. 15).

Example 3

This Example describes biochemical and genetic procedures conducted to identify a new partner of $CD151^{free}$, Activated Leukocyte Cell Adhesion Molecule (ALCAM). Functional studies demonstrated that CD151 and ALCAM control cell migration via PKCα-dependent activation of the small GTPase Rap1A. This mechanism was confirmed with both biochemical and genetic evaluation while the ability of Rap1 activation to control tumor cell motility was subsequently validated in vivo. It appears that integrin-free CD151 can bind ALCAM and control tumor cell motility via PKCα-dependent activation of the small GTPase Rap1A.

Materials and Methods

Cell Culture, Plasmids, Transfections, Inhibitors, and Antibodies

HEp3 cells were perpetually maintained on the chick chorioallantoic membrane (CAM) to retain metastatic and migratory potential. Cell lines were maintained in media supplemented with pen/strep, sodium pyruvate, non-essential amino acids and 10% fetal bovine serum and cultured at 37° C. in a 5% CO2 incubator. Plasmids used included untagged wildtype CD151 (Clontech Laboratories, Mountain View, Calif.). CD151-GFP (Osaka University, Osaka, Japan), ALCAM-GFP (University of Iowa, Des Moines, Iowa), and HA-Rap1 (Universitair Medisch Centrum Utrecht, The Netherlands) were obtained. Transfections of all cells were performed using Extreme Gene HD (Roche), excluding Cho cells which were transfected using polyethylenimine (PEI). Signaling pathways inhibitors included small molecule inhibitors of Rho kinase (Y 297632,), PI3kinase (LY294002), PI4kinase, (Wortmanin), MEK (UO126), PKA (KT5720), PKC (Calphostin) and Rap (GGTI-298) obtained from Calbiochem (EMD Millipore, Billerica, Mass.). Knockdown of gene expression was achieved with siRNAs to PKCα, and Rap1A and B and the control non-targeting siRNA purchased from Dharmacon (Fisher Scientific, Pittsburgh, Pa.). CD151 specific shRNA was obtained from Sigma Aldrich. ALCAM and GFP siRNA were purchased from Invitrogen (Grand Island, N.Y.). Anti-CD151 (1A5) was generated as previously described), ALCAM/CD166 (L50, Abcam and R&D systems). The control antibody 29-7 was generated in the same fashion as 1A5.

Mass Spectrometry

HEp3 and HT1080 cells were lysed in 1% Brij99 lysis buffer as described above. Lysates were incubated with control antibody 29-7 or anti-CD151 antibody 1A5 overnight at 4° C. and immunoprecipitated with protein-G sepharose beads. The immunoprecipitated complexes were then resolved by SDS-PAGEG. Each lane was excised and prepared for mass spectrometry analysis by the Vanderbilt University Mass Spectrometry Core (Nashville, Tenn.). Mass spectrometry analyses were performed with a LCQ-Deca or LTQ-Orbitrap mass spectrometer (Thermo Finnigan). Tandem mass spectra were extracted from raw files and used to search the database. Only proteins identified from two independent matrix preparations were considered as candidate components of the matrix.

Microarray and Gene Ontology Analysis

Gene Ontology analysis was performed with microarray data obtained from BLM melanoma cell lines were stably transfected with ΔN-ALCAM, sALCAM, or empty plasmid control. Samples were hybridized to Affymetrix U133Plus 2.0 (Santa Clara, Calif.) microarray chip. Intensities were normalized by $log_2$ transformation. Fold change was determined as compared to endogenous expression of wt ALCAM in BLM cells (empty vector control). P-value was determined using 2-tailed Student's t-test with unequal variances. Fold change and p-value calculations were done in Microsoft Excel (Microsoft Corporation, Redmond, Wash.). Genes with a fold change of at least 2 and p-value of 0.001 or less were considered differentially expressed. 260 gene probes were differentially expressed. Probe IDs of differentially expressed genes were up loaded to a WebGestalt analyzer. U133Plus 2.0 reference was selected. Gene ontology analysis was performed with default parameters. Enriched biological processes were highlighted in red and labeled with number of associated genes and adjusted p-value.

Cell Motility Assays

In Vitro Wound Healing Assay HEp3 and HT1080 cells were seeded to confluence in 6-well plates with complete medium. After 24 hrs the cells were switched to serum free/insulin free media for an additional 24 hrs. At 48 hrs after seeding the confluent monolayers were scratched with a pipet tip in order to create a uniform wound after which the cells were washed with PBS to remove any floating cells. Cultures were returned to full medium and the wound was documented at 0 hrs and 16 hrs post-scratch using a light microscope TMS-F (Nikon, Tokyo, Japan) equipped with a D90 SLR camera (Nikon). Wound closure (% surface area) was calculated using Tscratch image analysis software (Ashby et al., 2012; Gebäck et al., 2009).

In Vitro Transwell Migration: Tumor cells in a single cell suspension were plated into the top chamber of 8 μm transwell (Costar) inserts in the presence of serum free/insulin free media. Cell culture media containing 10% fetal bovine serum was placed in the bottom chamber to serve as a chemoattractant. Migration assays were carried out for 12 hrs in a 37° C. cell culture incubator containing 5% CO. The top surface of the inserts was cleaned with a cotton swab soaked with PBS to remove the non-migrated cells. The transwell inserts were subsequently fixed in methanol and stained with 0.2% crystal violet. The number of migrated cells was counted in 3 independent fields under 20× magnification with a light microscope.

Two-Dimensional Migration: Tumor cell migration on soluble ALCAM-Fc was performed by adhering it to tissue culture plates with protein-G. Briefly, protein-G (2 μg/ml) was adhered to the culture plastic followed by rat tail collagen type 1 (100 μg/ml). Unbound surface was blocked with BSA (0.5% in PBS) after which the surface was washed and incubated with ALCAM-Fc in 0.5% BSA. Control migration was performed on identical surfaces not inclubated with ALCAM-Fc. Tumor cells were seeded at low density and tracked by live cell imaging every 10 minutes over a 6 hr period with a fully automated microscope (BX61, Olympus, Tokyo, Japan) equipped with a digital camera (Orca ER, Hammatsu Photonics, Hamamatsu, Japan). Data acquisition and analysis was performed using Volocity image acquisition software (Perkin Elmer, Waltham, Mass.).

In Vivo Cell Motility: Briefly, cells to be injected were washed 2 times with PBS and detached with 2 mM EDTA. The cells were resuspended in PBS and injected intravenously into Day 12 chick embryos. Four days post-injection the disseminated colonies were photographed using a Lumar V12 stereomicroscope (Zeiss) equipped with a Retiga Exi camera and controlled with Volocity image acquisition software (PerkinElmer). Antibody treatments were introduced by intravenous injection one day after tumor cell injection. "Non-motile" colonies were defined as colonies comprised of 5 or more cells where individual cells remained in direct contact. Such non-motile colonies are compact while "motile" colonies contained a migratory cell populations dispersed in the CAM. Assays were performed with 5 animals/treatment and ≥5 fields/animal analyzed for colony formation. Data is represented as the percentage of colonies within a single animal that demonstrated a motile phenotype.

Flow Cytometry

Cells to be used in flow cytometry experiments were trypsinized with 0.25% Trypsin-EDTA and resuspended in cold Milytenyl FACs buffer (2 mM EDTA, 0.5% BSA, PBS). For the analysis of cell surface expression of specific antigens the cells were washed 2 times with FACs buffer and then stained with the specific primary antibodies for 1 hr on ice. Following incubation with the primary antibody the cells were washed 2 times with cold FACs buffer and then incubated with species-specific, fluorophore-conjugated secondary antibody for 30 minutes on ice. After washing two times the cells were suspended in cold FACs buffer and subjected to flow cytometry.

Immunoblot and Immunoprecipitation Analysis

Immunoblotting: For immunoblot analysis HEp3, HT1080 or CHO cells were lysed in either 1% (vol/vol) Triton X-100 lysis buffer or 1% (vol/vol) Brij-99 lysis buffer and incubated on ice for 30 minutes. The samples were then cleared by centrifugation at 14,000 rpm for 15 minutes and the cleared lysates were then transferred to fresh tubes. Protein concentrations were determined by BCA assay (Pierce). Equal amounts of protein were loaded in to SDS-Page gels and subsequently transferred to polyvinylidene fluoride membranes (PVDF, Millipore). The membranes were blocked for 1 hr in 5% non-fat dry milk in phosphate buffered saline with 0.05% Tween-20 (PBSt). The membranes were incubated overnight at 4° C. with specific antibodies prepared in blocking buffer after which the membranes were washed 3 times with PBSt and incubated with the appropriate species-specific horse radish peroxidase-conjugated secondary antibodies for 1 hr at room temperature. After washing, antibody binding was visualized by chemiluminescence.

Immunoprecipitation: 1 mg total cell lysate was incubated with 2 μg of the immunoprecipitation antibody and the antibody lysate solution was incubated over-night at 4° C. with end to end rotation. In order to capture the protein/antibody complexes the lysates were coupled to protein G sepharose beads (GE Healthcare) for 4 hr at 4° C. with end to end rotation. The lysates were cleared by centrifugation at 8000 rpm for 30 secs and the unbound material saved for further analysis. The beads were washed 3 times with either Triton X-100 or Brij-99 lysis buffer accordingly and the immune complexes were then eluted in 100 μl lamelli sample buffer and boiled for 5 minutes. The samples were then prepared for SDS-Page analysis. For GBP immunoprecipitations the lysates were incubated overnight with GBP conjugated beads with end to end rotation overnight at 4° C. After clearing the lysates were subjected to SDS-PAGE as described above.

Cell Surface Biotinylation: For cell surface labeling confluent HEp3 cells were treated with 1A5 or control antibody for 1 hr on ice and then washed with cold PBS. Cultures were subsequently biotinylated with sulfoccinimidyl-6-[biotin-amido]hexanoate using the EZ-Link Sulfo-NHS-Biotinylation Kit (Thermo Scientific) according to manufacturer's instructions. Cells were lysed in 1% Brij 99 followed by extraction of the insoluble in 1% Triton X-100. Immunoprecipitation was performed as described above. Biotinylated proteins were detected with peroxidase conjugated streptavidin.

Metabolic Labeling

HEp3 cells were labeled overnight in methionine/cysteine free DMEM containing 35S-label. Cells were washed throughly with PBS and lysed in 1% Brij 99 lysis buffer. The lysates were incubated with control antibody or monoclonal antibody 1A5 and immunoprecipitated as described above. The gels were dried and then exposed to film at −80° C.

Rap1 Activation Assays

Rap1 activation was analyzed using the Rap1 activation kit (Chemicon). All treatments were performed in the presence of serum free/insulin free media. Cells to be assayed were washed with ice cold PBS and lysed in RIPA like Rap1 buffer (10% glycerol, 50 mM Tris/HCl, 150 mM NaCl, 5 mM phenylmethylsulfonyl fluoride, 1 mM sodium orthovanadate). The lysates were pushed through a 25 gauge syringe and cleared by centrifugation at max speed at 4 degrees for 10 min. Equal amounts of lysates were immunoprecipitated with Ra1GDS RBD conjugated agarose beads for 45 minutes at 4° C. After washing the beads where resuspended with sample buffer and boiled for 5 minutes. The immunoprecipitates were separated by SDS-Page as mentioned above, transferred to PVDF membranes, probed with the anti-Rap1 antibody and horse radish peroxidase-conjugated secondary antibody. After washing the membranes were developed by autoradiography.

Immunfluorescence

HEp3 cells grown to confluency on collagen coated coverslips were incubated with 1A5 and then fixed in 4% formalin in PBS. The coverslips were blocked with 5% BSA in PBS for 30 minutes at room temperature and then stained with 1A5 and ALCAM primary antibodies overnight at 4° C. The coverslips were washed with PBS and then incubated with species specific fluorophore-conjugated secondary antibodies for 1 hr at room temperature). After staining the cells were washed with PBS and then counterstained with DAPI. The coverslips were then mounted onto glass slides with Fluorosave mounting media (Calbiochem). Pictures were taken with a BX 61 fluorescent microscope (Olympus) and analyzed using Volocity Image Acquisition Software (Perkin Elmer).

Statistical Analysis

All statistical analysis was performed using Graph Pad Prism Analysis Software (La. Jolla Calif.). For statistical analysis of migration experimental groups were compared to the control groups using non-parametric Mann-Whitney test.

Results

Identification of CD151 Associated Proteins

Figure 16A:
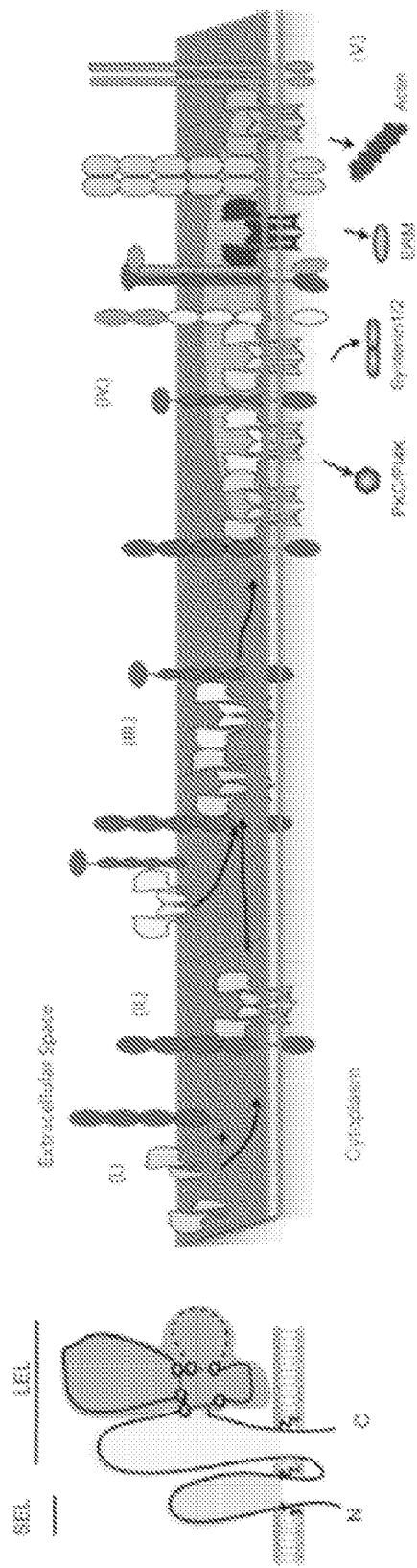
FIG. 16 shows the mass spectrometry analysis and discovery of ALCAM as a CD151 associated protein. (A) (left panel) General tetraspanin schematic with the small extracellular loop (SEL) and the large extracellular loop (LEL) highlighted. (right panel) Schematic representation of tetraspanin-partner interaction (I-II), TERM assembly (III-IV) and interaction with intracellular signaling molecules (V). (B) Detection of CD151 and associated proteins by metabolic labeling (S35), cell-surface biotin labeling (biotin), or CD151-specific immunoblot after immunoprecipitation from a HEp3 cell lysate. (C-D) Mass Spec analysis (LC-MS-MS) of CD151-associated proteins after immunoprecipitation by antibody 1A5. (C) SDS-PAGE used for LC-MS-MS and pie-chart representing distribution of identified targets. D). Table of known CD151-associated proteins and putative partners that can potentially control migration. E). Gene Ontology analysis performed with WebGestalt on genes differentially expressed after the introduction of a dominant-negative ALCAM.
Figure 16E:
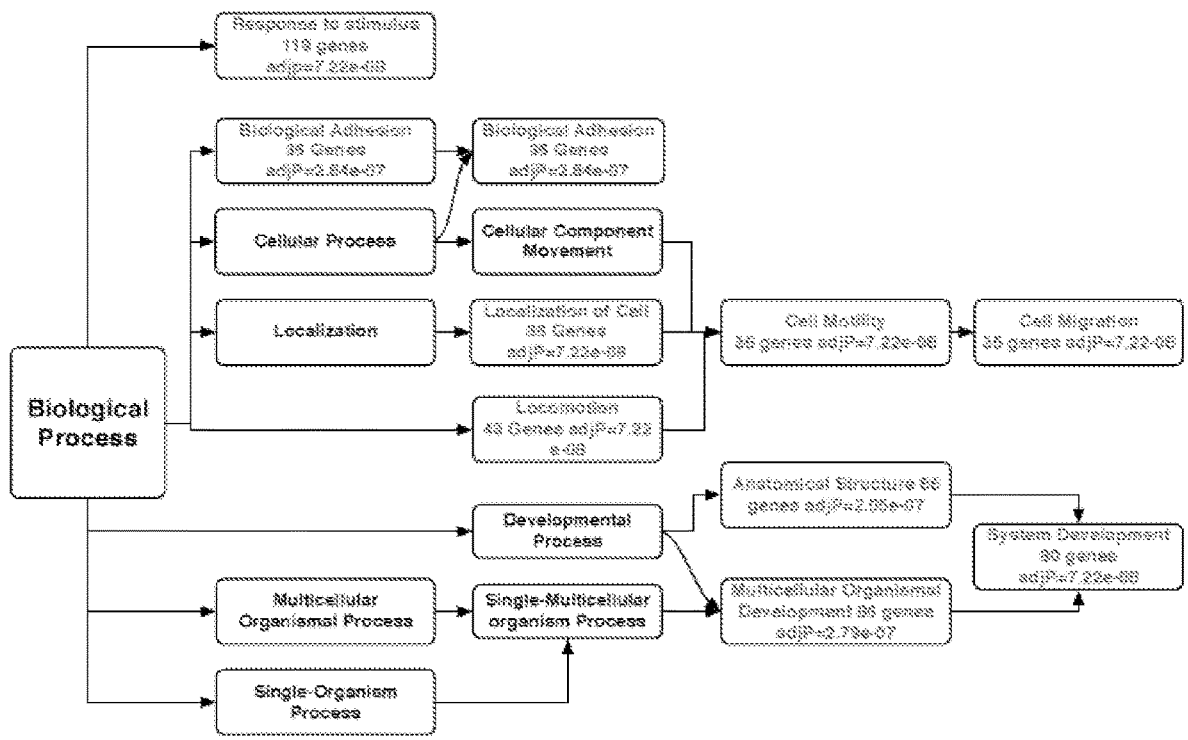

The ability of tetraspanins to organize higher-order structures in the membrane leads to complex interactions of variable affinity with a variety of transmembrane and membrane proximal proteins (FIG. 16A). Immunoprecipitation of CD151 with the motility-inhibiting antibody 1A5 from lysates extracted with mild detergents (Brij) or stringent detergent (TX-100) co-precipitates several proteins (FIG. 16B) visible after metabolic labeling (S35), and cell-surface biotinylation (Biotin). In order to elucidate the components of the CD151-TERM complex responsible for regulating tumor cell motility and metastasis, tandem Mass Spectrometry (LC-MS-MS) was used to identify CD151 partners that co-IP with 1A5 (FIG. 16C). Specifically, the HNSCC cell line HEp3 was lysed with Brij-based lysis buffer to maximize possible protein-protein interactions. Immunoprecipitations were preformed with the CD151$^{free}$-binding antibody 1A5. Control samples included immunoprecipitations with an isotype-matched control IgG or protein-G only. The precipitated complexes were separated by SDS-PAGE, gel pieces were excised and subsequently analyzed by LC-MS-MS using a LCQ-Deca or LTQ-Orbitrap mass spectrometer (ThermoFinnigan). CD151-specific candidates were identified by eliminating targets precipitated with an isotype control and protein-G respectively. Candidates identified by two or more peptides in two or more independent analyses were selected as viable targets. A total of 228 proteins were identified of which 51 candidates distributed across five phenotypic subgroups were detected repeatedly (FIG. 16C, pie chart and Table 11).

Anti-CD151 antibody 1A5 clusters the tetraspanin and promotes its accumulation at areas of cell-cell contact. Based on validated interactions and the observed cell-cell accumulation, a short list of potential candidates was developed (FIG. 16D). Nearest neighbor analysis was performed on each putative candidate using the Broad Institute Cancer Cell Line Encyclopedia (http://www.broadinstitute.org/ccle/home). ALCAM was identified as the nearest neighbor of α3, one of the primary partners of CD151. To evaluate ALCAM's role as a regulator of migration we evaluated changes in gene expression initiated upon expression of a dominant-negative ALCAM lacking the ligand-binding domain. Differentially expressed genes were grouped by gene ontology (GO) association using WebGestalt (http://bioinfo.vanderbilt.edu/webgestalt/) and enriched biological processes were displayed. The primary processes identified were cell adhesion and migration. In addition to its association with cancer metastasis and migration, ALCAM has also been suggested to interact with PKCα, a key regulator of CD151 activity, supporting its potential as a bonafide partner in the regulation of tumor cell motility by CD151. ALCAM has broad expression in epithelial tissues and their corresponding tumors. Continuous cell lines derived from these tumors continue to express ALCAM both at the level of gene transcription and protein translation.

The IgG Superfamily Member ALCAM is a Novel CD151 Partner

Figure 17A:
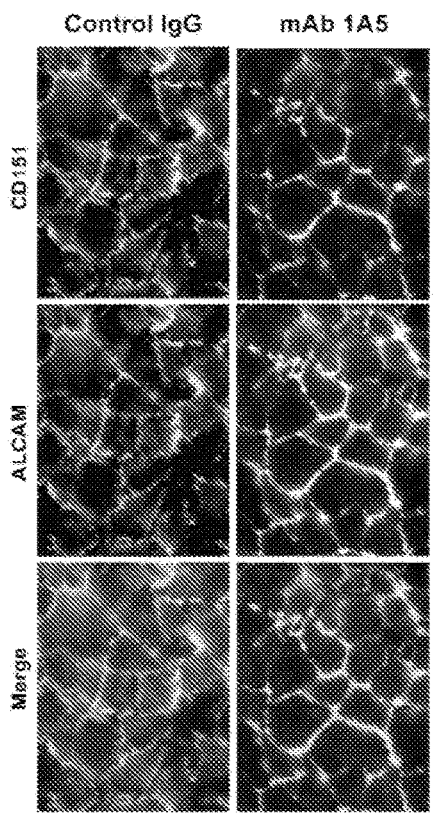
FIG. 17 shows the physical association of CD151 with ALCAM. (A) Immunofluorescent staining of CD151 and ALCAM in HEp3 cells treated with control IgG or 1A5. (B) Co-immunoprecipitation of ALCAM by anti-CD151 antibody 1A5. (C) Co-immunoprecipitation of CD151 by anti-ALCAM antibody. (D-E) Co-precipitation of ALCAM and CD151 after pull-down of GFP-tagged partner. (CD151*=untagged CD151 that co-precipitates with CD151-GFP).
Figure 17B:
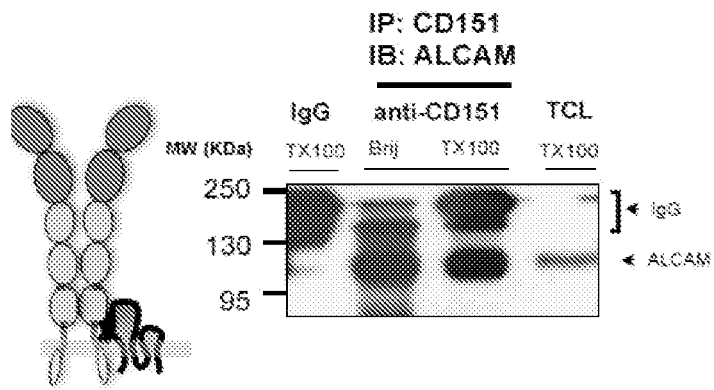
Figure 17C:
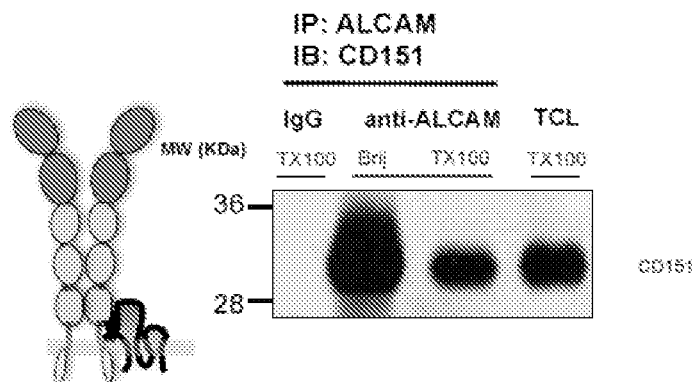
Figure 17D:
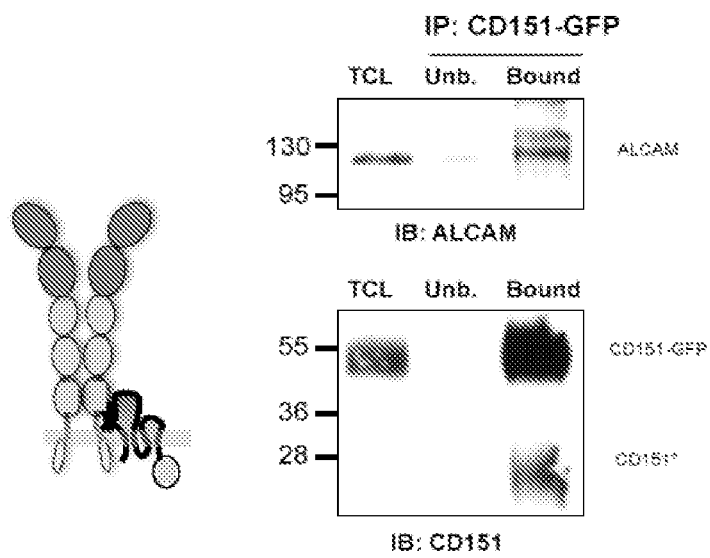
Figure 17E:
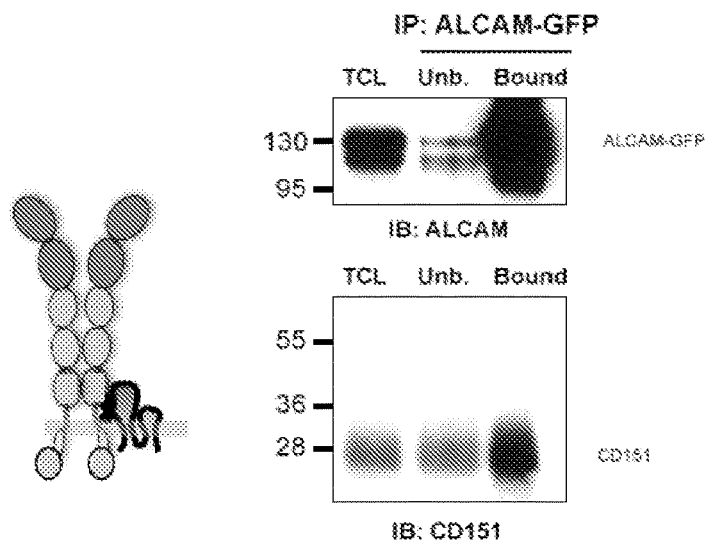

Clustering of CD151 with 1A5 promotes the localization of the tetraspanin to the areas of cell-cell contact leading to the inhibition of tumor cell migration and metastasis. ALCAM and CD151 occupy the same areas of cell-cell contact and clustering of the tetraspanin causes ALCAM to co-localize extensively with CD151 (FIG. 17A). To determine if CD151 and ALCAM were physically interacting, the proteins were immunoprecipitated from mild (Brij) and stringent (TX-100) detergent lysates obtained from the HNSCC HEp3 using the antibodies 1A5 and AZL50 respectively and the resulting precipitations were immunoblotted for its possible partner (FIGS. 17B and 17C, respectively). CD151 and ALCAM did indeed co-immunoprecipitate in their reciprocal precipitations. Since 1A5 drives CD151 clustering and promotes an interaction between CD151 and ALCAM, an independent validation of the interaction between CD151 and ALCAM was performed using affinity purification of GFP-tagged proteins. ALCAM-GFP and CD151-GFP were co-transfected with untagged CD151 or ALCAM respectively into CHO cells. GFP-tagged protein was precipitated from TX-100 lystates using a GFP-binding protein (FIGS. 17D and 17E). ALCAM co-precipitated with CD151-GFP and CD151 co-precipitated with ALCAM-GFP.

These four independent precipitations demonstrate that CD151 forms a complex with ALCAM and that ALCAM is a component of the CD151-TERM. This complex is stable under stringent detergent conditions (TX-100) suggesting that the stability of the CD151-ALCAM interaction is similar to those observed previously for CD151-α3.

ALCAM and CD151 Cooperate in their Ability to Regulate Migration

Figure 18A:
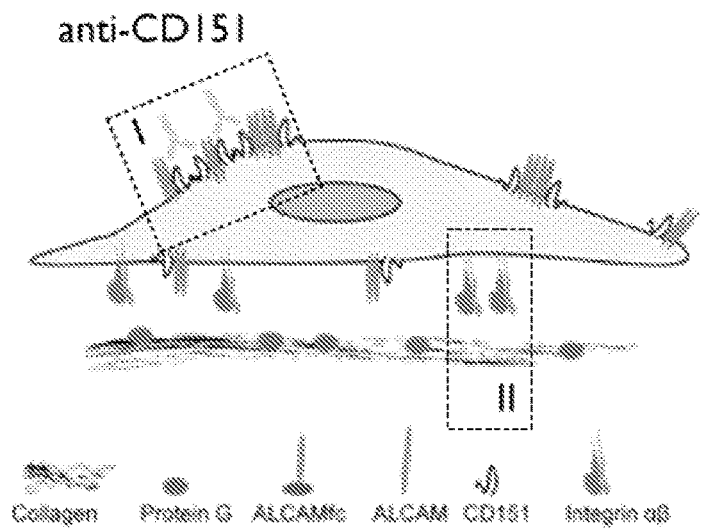
FIG. 18 shows that CD151 and ALCAM cooperate in the regulation of tumor cell migration. (A) Schematic representation of migration in response to clustering of CD151 by antibody 1A5 (I) which results in enhanced adhesion (II) and subsequent inhibition of migration. (B) Transwell migration of HT1080 cells in the presence or absence of 1A5 after transfection with control siRNA (white bars) or ALCAM siRNA (black bars). (C) Immunoblotting and immunofluorescent staining of cultured cells. (D) Schematic representation of migration in response to ALCAM-ALCAM interactions. (E) Analysis of cell migration on ALCAM-Fc by single-cell tracking. Migration velocity is determined after transfection with control shRNA (white bars) or CD151 shRNA (black bars). (F) Immunoblotting and immunofluorescent staining of cultured cells.
Figure 18B:
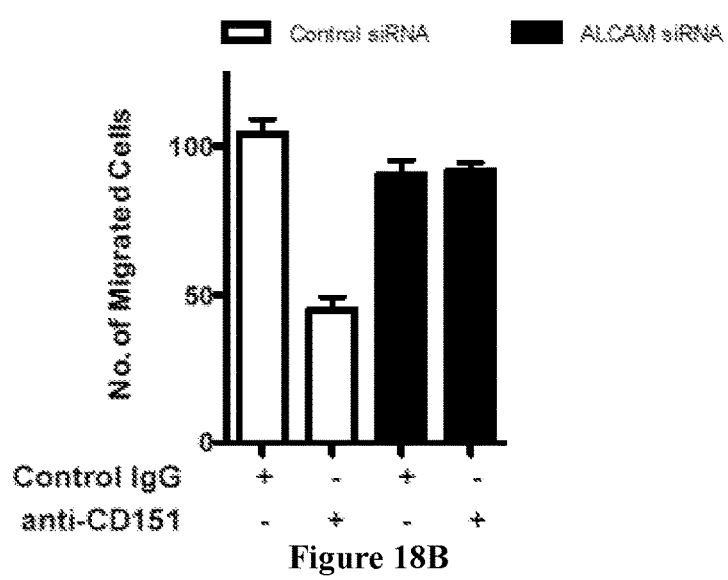
Figure 18C:
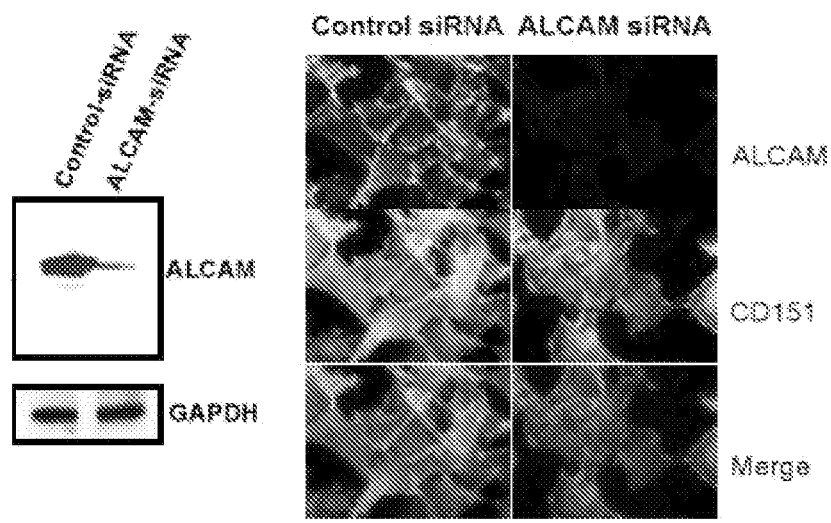
Figure 18D:
Figure 18D:
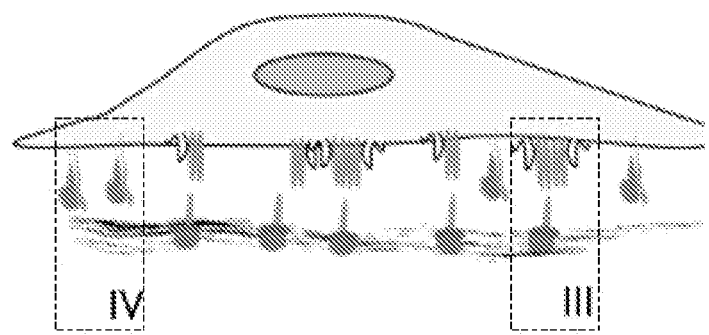
Figure 18E:
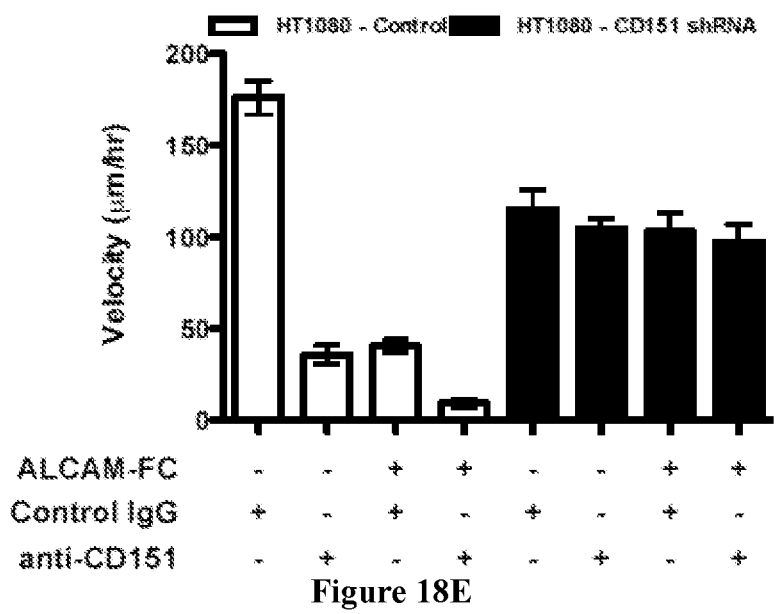
Figure 18F:
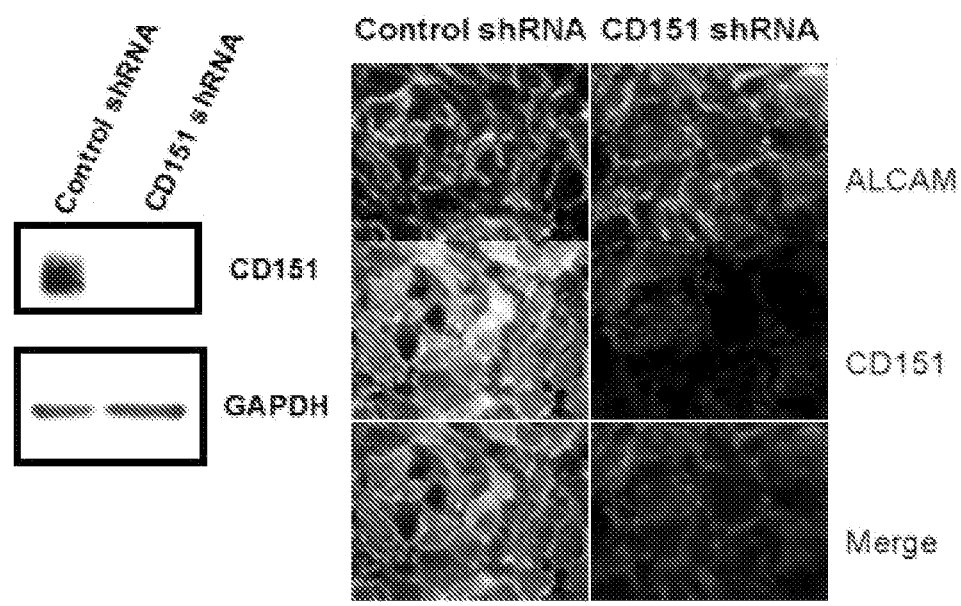

The physical association of CD151 and ALCAM demonstrates that ALCAM is a component of the TERM complex. To determine the relevance of this interaction in cell motility, the ability of CD151 and ALCAM to regulate migration was evaluated after RNAi-mediated depletion in HT1080 and HEp3 cells (FIG. 18). CD151 clustering induced by the antibody 1A5 inhibited HT1080 tumor cell migration (FIG. 18A). After RNAi-mediated depletion of ALCAM, tumor cells were no longer sensitive to the immobilization by CD151 (FIGS. 18B and 18C). Engaging HT1080 cells in ALCAM-ALCAM interactions can be accomplished by seeding cells on ALCAM-Fc coated surfaces (FIG. 18D). Similar to anti-CD151 treatment, engaging ALCAM-ALCAM interactions can inhibit tumor cell motility in a wound-healing assay. The inhibition of cell motility upon ALCAM-ALCAM binding was enhanced by 1A5-induced clustering of CD151 (FIG. 18E, white bars). Conversely, shRNA mediated knockdown of CD151 in HT1080 cells not only eliminated sensitivity to the anti-CD51 antibody 1A5 but also prevented the inhibition of motility by ALCAM-ALCAM ligation (FIG. 18E, black bars). Similar observations were made for the HNSCC HEp3. These data demonstrate that CD151 and ALCAM cooperate to control tumor cell motility.

Figure 19A:
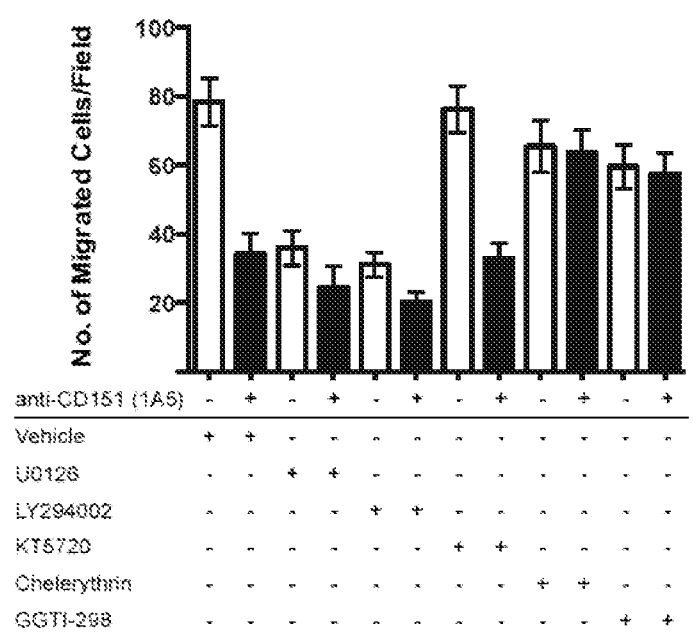
FIG. 19 shows that the CD151/ALCAM signaling mechanism involves PKC and the small GTPase Rap1. (A) Transwell migration of HEp3 cells in the absence (white bars) or presence of 1A5 Anti-CD151 (black bars) analyzed in the presence of different pathway inhibitors. (B) Wound healing migration of HEp3 cells expressing siRNAs specific for ALCAM, PKCα, and Rap1. (C) Rap1 activation HEp3 cells serum starved overnight and treated with 1A5 in culture for the indicated time points. (D) Plating HEp3 cells on ALCAM-Fc activates Rap1 in a time dependent manner but has not impact on the activation of state of the small GTPase Rac1. (E) 1A5 treatment activates Rap1 in a PKCα-dependent manner.
Figure 19B:
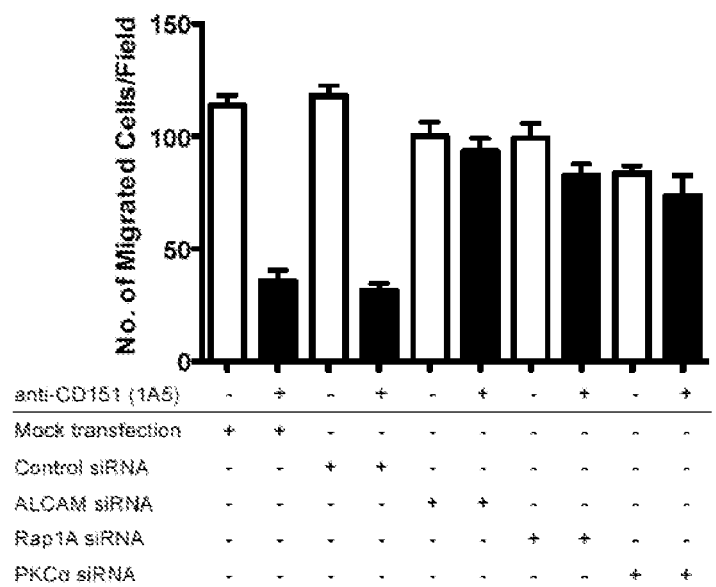
Figure 19C:
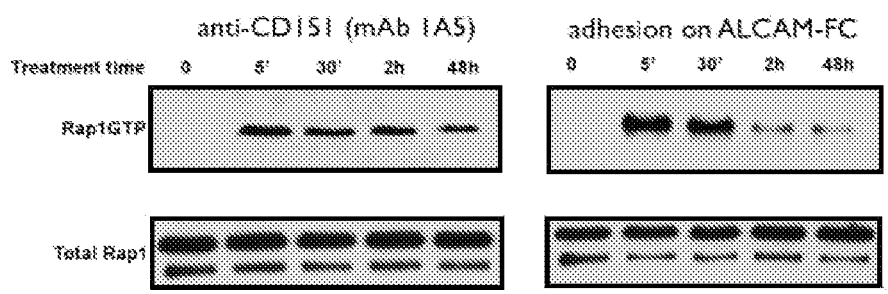
Figure 19D:
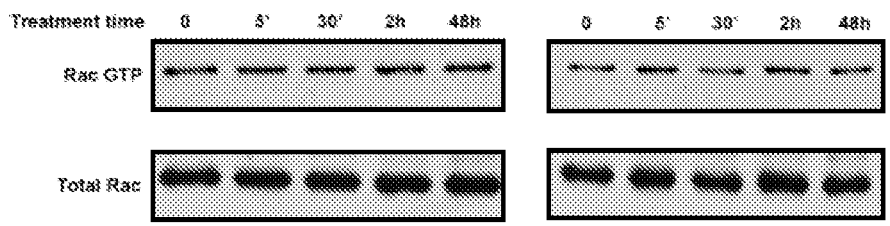

CD151 and ALCAM Control Tumor Cell Migration Through PKCα-dependent Activation of Rap1A A targeted pharmacological screen was performed in an attempt to identify molecular mechanisms that might contribute to the inhibition of motility mediated by CD151 and ALCAM (FIG. 19A). Tetraspanins regulate intracellular signaling events by interacting directly or indirectly with signaling molecules including protein kinase Cα (PKCα)

and phosphatidylinositol 4 kinase type IIa (PI4kinase Type IIa). Rho and PI3 kinase have also been associated with CD151-mediated regulation of tumor cell motility. MEK, Erk, and Rap1 were targeted as established mediators of cell motility. Transwell migration assays were performed in the presence or absence of each inhibitor together with or without the anti-CD151 antibody 1A5. The MEK inhibitor (U0126) and PI3 kinase inhibitor (LY294002) inhibited migration independent of anti-CD151 antibody treatment (1A5) while the PI3 kinase inhibitor (Wortmannin) did neither influence the migration of untreated cells nor did it prevent the inhibition of migration by 1A5. Conversely, the PKC inhibitor (Chelerythrin) and the RAp1 inhibitor (GGTI-298) allowed for migration of untreated cells but prevented 1A5 from inhibiting migration. RNAi-mediated ablation (siRNA) of PKCα and Rap1A confirm that these proteins are required for CD151 to inhibit motility (FIG. 19B). Rap1A is a GTPase that can promote adhesion upon activation. To evaluate whether Rap1A was activated in response to CD151 clustering as well as ALCAM-ALCAM ligation, HEp3 cells were treated with 1A5 or seeded on ALCAM-FC for up to 48 hrs. Active Rap1A in the cells was evaluated by immunblotting of GTP-bound Rap1A affinity purified from lysates with Ral-GDS beads. Both CD151 clustering and ALCAM-ALCAM binding resulted in rapid and persistent activation of Rap1A (FIG. 19C). Activation of the GTPase Rac was evaluated as a control to confirm the specificity of Rap1A activation (FIG. 19D).

Figure 19E:
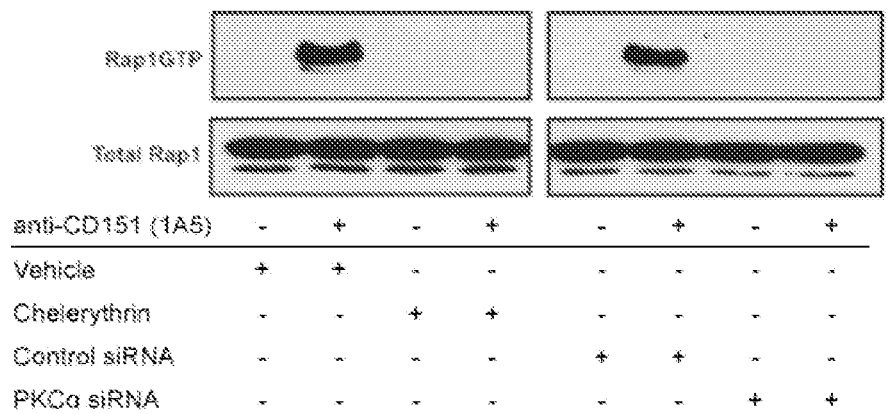

PKCα can associate with CD151 and ALCAM and has also been demonstrated to mediate activation of Rap1. Together with the observed contribution of PKCα to the regulation of migration (FIGS. 19A and 19B), this suggests that PKCα may mediate activation of Rap1A by CD151 and ALCAM. To determine if PKCα signaling is required for Rap1A activation by CD151, GTPase activity assays were performed in HEp3 cells after PKCα was disrupted with Chelethyrine or PKCα-specific siRNA (FIG. 19E). In control transfected or untreated cells 1A5 promotes activation of Rap1A, however, when PKCα is knocked down by genetic manipulation or inhibited by pharmacological means, 1A5 was unable to promote Rap1A activation. This demonstrates that downstream of CD151 clustering, Rap1A is activated in a PKCα-dependent manner.

Rap1 Activation is Sufficient to Immobilize Tumor Cells In Vitro and In Vivo

Figure 20A:
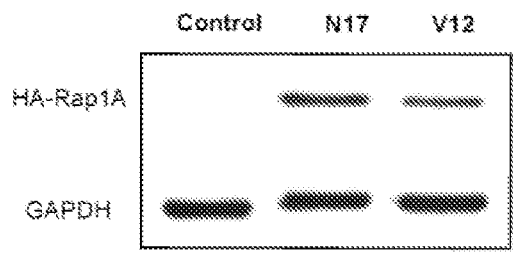
FIG. 20 shows that Rap1 activation can inhibit tumor cell motility in vitro and in vivo. HEp3 cells were transiently transfected with empty vector (Control) dominant negative Rap1 (N17) or dominant active Rap1 (V12). (A) Transgene expression was verified by immunoblotting for the HA-tagged protein. (B) In Vitro cell migration was performed with transiently transfected cells in a wound-healing assay. (C) and (D) HEp3 cells were injected into 12 day old chicks and the migratory phenotype of metastatic colonies was evaluated (see methods for details). The number of motile colonies was quantified (C) from images taken of the chorioallantoic membrane containing metastatic colonies (D). Data is representative of three experiments with n≥5 for each experiment.
Figure 20B:
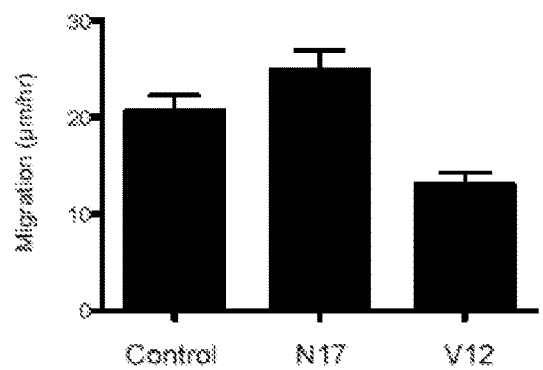
Figure 20C:
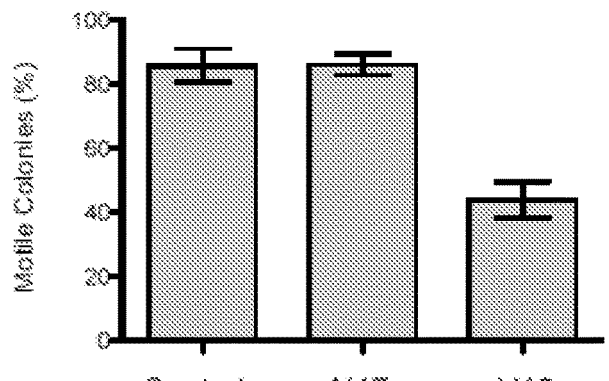
Figure 20D:
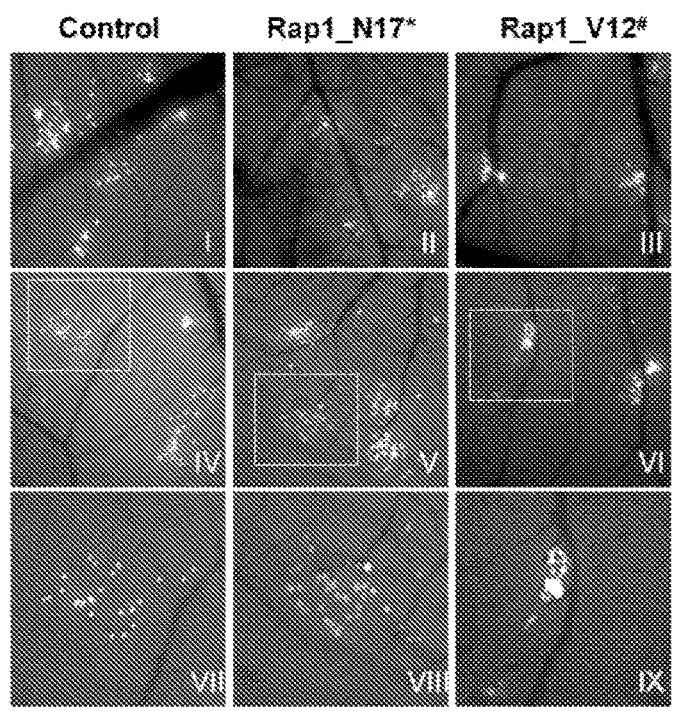

Rap1A serves as a molecular switch capable of regulating cell motility by controlling adhesion. The inhibition of tumor cell motility in response to CD151 and its partner ALCAM involves the activation of Rap1A. It appears that Rap1 activation was sufficient to inhibit tumor cell motility, and to address this issue GFP-expressing HEp3 cells was transfected with dominant negative Rap1A (Rap1N17) or the dominant active Rap1A (Rap1V12). The expression of the constructs was verified by western blot analysis (FIG. 20A). Migration assays were subsequently performed in order to determine if Rap1A activity was sufficient to impact on tumor cell migration in vitro. Dominant negative Rap1A (Rap1N17) had no significant impact while the dominant active Rap1A (Rap1V12) reduced migration. This observation extended to in vivo migration. HEp3-GFP cells transfected with dominant negative Rap1A (Rap1N17) or dominant active Rap1A (Rap1V12) were injected intravenously into D12 avian embryos and metastatic colony formation was analyzed at 4 days post injection. Colony size can reflect tumor cell growth while the local dispersion of metastatic tumor cells reflects on their motility. All of the transfected cells demonstrated efficient colony formation. However, HEp3 cells expressing dominant active Rap1A (Rap1V12) formed compact colony indicative of reduced motility while mock and Rap1N17 transfected cells exhibited a dispersed, motile colony appearance.

Discussion

CD151 and ALCAM as Partners in the Regulation of Tumor Cell Migration

ALCAM was identified a novel CD151 partner that can associate with integrin-free CD151. ALCAM is expressed broadly in human tissues and cells with predominant expression in neuronal cells, immune cells, epithelial cells, and stem cells of hematopoietic and mesenchymal origin, it is functionally associated with many cell adhesion events including T-cell activation, endothelial adherence junction, neuronal guidance, and epithelial integrity. ALCAM's expression alters during cancer progression. Since ALCAM-ALCAM interactions are responsible for mediating the activation of Rap1A and inhibiting motility, it appears that ALCAM shedding offers a mechanism by which tumor cells can control Rap1A-mediated adhesion and migration.

Molecular Integration of CD151, ALCAM, PKCα and Rap1A

PKCα binding to the C-terminal tail of CD151 allows the tetraspanin to serve as a linker between PKCα and the integrins α3β1 and α6β4 thereby regulating integrin signaling. It appears that CD151 performs the same function for ALCAM but that the ultimate target of this signaling is Rap1A. PKCα has been previously identified as an inhibitor of cell migration during an in vitro screening assay of normal epithelial migration. Since PKCα has many substrates, these results suggest that divergent signaling mechanisms may be initiated depending on what partner CD151 interacts with. The elevation of integrin-free CD151 in cancer is likely to divert signaling from integrins to other tetraspanin partners.

Both CD151 clustering and homotypic ALCAM-ALCAM interactions mediated promote tumor cell adhesion and control motility by activating the small GTPase Rap1A. Since then many lines of evidence demonstrate that Rap1 can influence cancer progression, including the identification of SIPA1, a Rap1 GTPase activators (Rap1GAP) as the mediator of differential metastatic ability associated with Polyoma Middle T antigen initiated breast cancer, and metastatic virulence in breast cancer appears to be associate with specific Single Nucleotide Polymorphisms (SNPs) in SIPA1. Thus, active (GTP-bound Rap1) may limit metastatic dissemination. This Example demonstrates that the activation of Rap1A (generating the GTP-bound state of Rap1A) promotes adhesion and thereby limits dissemination.

The activity of Rap1 is regulated by a number of regulators including Guanidine Exchange Factors (GEF), GTPase activators (GAP) and effectors that mediate the activity of the GTPase. This Example demonstrates that in the absence of PKCα, neither 1A5 treatment nor ALCAM adhesion is able to activate Rap1, which suggests that the signaling mechanisms associated with immobility require PKCα to activate Rap1A. PKCα can activate Rap1 in platelets and subsequently promote adhesion through integrin activation. CD151 was initially identified as a platelet cell surface antigen and its clustering can induce platelet activation suggesting that this mechanism may apply broadly outside the regulation of tumor cell motility.

Example 4

This Example describes procedures conducted to show that ectodomain shedding of ALCAM is induced by cytokines present in the tumor microenvironment and that its detection can be a marker of tumor progression. ALCAM expression and shedding by ADAM17 is examined in response to cytokine stimulation through biochemical analyses while its contribution to skeletal metastasis is determined in a series of orthotopic, and experimental metastasis models. Specifically, this Example characterizes how elevated ALCAM expression in aggressive prostate cancer together with its putative role in cell adhesion/migration make ALCAM a molecular participant in prostate cancer metastasis.

Materials and Methods

Reagents, Cell Culture

Full-length purified recombinant porcine TGFβ was obtained from. Antibodies against ALCAM were obtained from R&D Systems (Clone 105902). The following tumor cell lines were obtained from American Type Culture Collection (Manassas, Va.) and maintained according to the American Type Culture Collection's recommendations: DU145, LNCaP, PC3 (prostate metastasis). PC3-luciferase (PC3-luc) cells (Simon Hayward, Vanderbilt) were cultured in RPMI/10% FBS.

SDS-PAGE and immunoblotting. Cells ($2.5 \times 10^5$) were plated in 6-well dishes. After 24 h, cells were serum starved in Opti-MEM for 16 h and then treated in the presence or absence of indicated growth factors or inhibitors, for 48 h. After that, the cells were lysed in TNE Lysis Buffer (20 mM Tris-Cl [pH 7.4], 0.5 mM EDTA, 1% Triton X-100, 150 mM NaCl, protease inhibitor cocktail (sigma), 1 mM phenylmethylsulfonyl fluoride). Total protein in the lysates was quantified using BCA assay (BioRad). Conditioned media samples were concentrated with microcon centrifugal filters (Millipore) following manufacturers protocol, which were eluted directly in 5× sample buffer for Western blot analysis. Protein loading for conditioned-medium samples for Western blot analysis was adjusted according to the total protein in cell lysates. Conditioned media and total protein was subjected to SDS-PAGE and electrophoretic transfer to polyvinylidene difluoride membranes (Immobilon P, Millipore, Inc., Bedford, Mass.). Immunodetection was done by conventional chemiluminescence Quantitative PCR The mRNA samples were prepared from tumor cells lysed in TRI Reagent (Ambion) and purified using phenol extraction, followed by real-time polymerase chain reaction (RT-PCR). The following qPCR primers were used ALCAM, TCAAGGTGTTCAAGCAACCA (forward) and CTGAAATGCAGTCACCCAAC (reverse); ADAM17, ATGTTTCACGTTTGCAGTCTCCA (forward) and CATG-TATCTGTAGAAGCGATGATCTG (reverse); and glyceraldehyde-3-phosphate dehydrogenase, ATCTTCTTTT-GCGTCGCCAG (forward) and TTCCCCATGGTGTCTGAGC (reverse).

ShRNA Knockdown

To establish cell lines in which ALCAM expression is stably knocked down cells were transduced with ALCAM-specific Mission shRNA (Sigma) lentivirus. Following transduction, cells were selected in 10 μg/ml of puromycin. Transduced cells were flow sorted for ALCAM expression and ALCAM knock-down cells were cultured and maintained on 5 μg/ml of puromycin.

Migration Assay

Two-dimensional gap closure assays (formerly known as scratch assays) were conducted using magnetically attachable stencils attached to culture plates. 250,000 cells were seeded in 6-well plates and allowed to recover overnight to form a confluent monolayer. Stencils were removed with tweezers, after which cells were rinsed with PBS to remove detached cells. Culture medium was re-added and closure of the gap was measured at 8 and 16 hours. Gap closure was quantified using TScratch (National Institutes of Health, Bethesda, Md., USA).

Histological Analysis of Mouse Tissue

Tumor-bearing tissue and bones were fixed in 10% formalin. Bone specimens were decalcified in 20% EDTA pH 7.4 for 3-4 days at room temperature. Decalcified bone and tissue were dehydrated and embedded in paraffin. Tumor burden was confirmed in 5 μm serial sections stained with H&E. Osteoclast were visualized using a standard Tartrate Resistant Acid Phosphatase (TRAP) protocol. All immunohistochemistry and immunofluorescence on tumor sections involved antigen retrieval using a standard pH 6.0 citrate buffer followed by blocking via incubation with 20% Aquablock (East Coast Bio, North Berwick, Me.). Immunofluorescence data was obtained using primary antibodies for ALCAM (1:1000; Leica Biosystems; Clone, MOG/07), Ki67 (1:500; Fisher, Clone SP6), Cleaved caspase-3 (1:200; CellSignaling, D175), and collagen I (1:1000; Sigma C2206) by incubation overnight at 4° C. Corresponding Alexa Fluor® secondary antibodies were used (1:1000; Invitrogen). Fluorescent imaging was completed on a Olympus BX61WI upright fluorescent microscope using Volocity Imaging Software.

ELISA of Mouse Serum and Plasma

Blood was obtained via the saphenous vein; samples were collected in either the presence of EDTA as an anticoagulant or a serum separator tube and were centrifuged at 1,500 rpm, 4° C. to remove cells. Plasma and serum samples were stored at −80° C. until analyzed. Samples were analyzed for soluble mouse and human ALCAM using the R&D Systems DuoSet following manufacturer's instructions. Briefly, ELISA plates coated with capture antibody were incubated overnight with 100 μL of sera diluted 1:50. Capture ALCAM was detected with biotinylated antibody and peroxidase-conjugated avidin followed by colorimetric detection at 450 nm.

Mouse Models of Prostate Cancer and In Vivo Quantitation of Tumor Growth

Briefly, $5 \times 10^4$ PC3-luc cells were suspended in 30 μl of neutralized type I collagen and allowed to polymerize for 16 hrs at 37° C. before implantation into the prostate of 10 week old C.B-17/IcrHsd-Prkdc scid male mice (Harlan, Indianapolis, Ind.). Tumor growth was monitored weekly by bioluminescent detection of luciferase expressing cells. For the xenograft model, subconfluent PC3-luc cells were trypsinized, washed twice in PBS to remove serum, and then resuspended in HBSS at a concentration of $1 \times 10^7$ cells/mL. One hundred μl containing $1 \times 10^6$ PC3 cells in a 50/50 mix of PBS and growth factor-reduced Matrigel (BD Biosciences, San Jose, Calif.) were injected subcutaneously into the right flank of 7-week-old nude male mice (Harlan Laboratories; athymic Foxn1 nu/nu). Tumor growth was monitored weekly by caliper measurements, and tumor volume was calculated based on the following formula: (length×length×width)/6. PC3-luciferase shControl (Vector) or PC3-luciferase shALCAM (KD2 or KD3) tumor cells ($1 \times 10^5$) in a 10 μl volume of sterile phosphate buffered saline (PBS) were injected into the tibia of anesthetized 6-week-old nude male mice (Harlan Laboratories) Skeletal metastasis was performed. Briefly, $1 \times 10^5$ PC-3-luc cells were injected into the left heart ventricle of male nude mice (Harlan Laboratories). Skeletal metastases were monitored by bioluminescent detection of luciferase expressing cells and formation of bone lesion by X-ray. Whole animal luminescent imaging was performed with the IVIS™ system (Caliper Life Sciences, Hopkinton, Mass.). Luciferin (150 mg/kg in sterile PBS, Biosynth International, Itasca, Ill.) was delivered via intra-peritoneal injection 10 minutes prior imaging. Living Image™ software (Caliper Life Sciences, Hopkinton, Mass.) was used to quantify the luminescence intensity. Blood was obtained via the saphenous vein and collected in either the presence of EDTA as an anticoagulant or a serum separator tube (Fisher Scientific). Plasma and serum samples were stored at −80° C. until analyzed.

Micro Computed Tomography (μCT) Analysis

For gross analysis of trabecular bone volume, formalin fixed tibiae were scanned at an isotropic voxel size of 12 μm using a microCT40 (SCANCO Medical, Bruttisellen, Switzerland). The tissue volume (TV) was derived from generating a contour around the metaphyseal trabecular bone that excluded the cortices. The area of measurement began at least 0.2 mm below the growth plate and was extended by 0.12 mm. The bone volume (BV) included all bone tissue that had a material density greater than 438.7 mgHA/cm$^3$.

Radiographic Analysis

Beginning 1 week after tumor cell inoculation, tumor-bearing animals were subjected to radiographic imaging. Radiographic images (Faxitron X-ray Corp, Lincolnshire, Ill., USA) were obtained using an energy of 35 kV and an exposure time of 8 seconds. Osteolytic lesions were quantified bilaterally in the tibia, fibula, femora, humeri, and pelvis at the endpoint using x-ray images. Lesion area and lesion numbers were evaluated using image analysis software (Metamorph, Molecular Devices, Inc.). Data presented are the average of lesion area and lesion numbers per mouse in each group.

Statistical Analyses

Expression analysis was performed on datasets GDS1439 and GSE10645 available through the Gene Expression Omnibus (references (21) and (22) respectively). Expression data for selected genes from GDS1439 was clustered in software Cluster 3.0 and visualized with software TreeView. For survival analysis the patient population of GSE10645 (n=596) was dichotomized across upper and lower quartile of ALCAM expression. Statistics were completed using either R, SPSS or GraphPad Prism. For all standard bar and box plots the results were reported as mean and SEM unless stated otherwise in the legend. Comparisons were performed using unpaired two-sided Student's t test, nonparametric Mann-Whitney test, or one-way ANOVA. $R^2$ and P values were reported from linear regression analysis of mouse data. All statistical tests were considered significant when $p<0.05$ where * denotes $p<0.05$,  denotes $p<0.01$ and * denotes $p<0.001$.

Mouse Models of Acute Inflammation

C57BL/6(SJL)-Tg(SMAD binding element [SBE]/Tk-luc)7Twc/J mice, obtained from the laboratory of Harold Moses, MD (Vanderbilt University), were used at 16 weeks of age. These transgenic mice, referred to as SBE-Luc mice, express luciferase in response to activation of the Smad2/3-dependent signaling pathway. Mice were administered 2 mg/kg of LPS to induce an acute inflammatory response and bled via saphenous vein at 0, 6, 24 hours and 1 week post-administration.

Mouse Models of Wound-healing

Mice were anesthetized by intraperitoneal injection. The back the C57/B16 male and female mice were shaved and two circular excisional full-thickness wounds of 6-mm diameter generated using a standard biopsy punch. Mice were bled via saphenous vein at 0 hours (establish basal levels), 24 hours, one week and two weeks after wound initiation.

In Vivo ALCAM Serum Half-life

Serum was harvested from ALCAM wild-type, mixed background, mice and pooled. Combined serum collected from WT mice was injected retrorbitally in ALCAM KO mice (100 μl/mouse). ALCAM KO mice were pre-bled via saphenous vein bleed, and then bled at 10 mins, 2 hours, 4 hours, 24 hours and 48 hours (n=2/time point; total n=10). WT pooled serum was used as ELISA control to quantitatively determine ALCAM serum half-life.

Results

ALCAM Gene Expression is Elevated in Advanced Prostate Cancer and Correlates with Poor Patient Outcome Several publicly available microarray datasets were evaluated to determine the relationship between ALCAM mRNA levels, patient diagnosis and outcome (FIG. 21). A comparison of benign, localized and metastatic disease revealed increased levels of ALCAM mRNA in metastatic prostate cancer (FIG. 21A). Elevated levels of ALCAM coincided with molecular evidence of a pro-migratory phenotype based on the decreased expression of E-cadherin and p120 concurrent with elevated expression of N-cadherin (FIG. 21B). These observations were supported by survival analysis for a cohort of 600 prostate cancer patients which revealed that high levels of ALCAM mRNA corresponded with poor patient outcome. (FIG. 21C). Immunohistological staining of prostate cancer tissue microarrays available through the Human Protein Atlas revealed that ALCAM staining is evident in both normal, benign and malignant disease but is frequently absent from the tumor cell surface in advanced disease (proteinatlas.org, FIG. 21D).

TGFβ Induces ALCAM Expression and Shedding

Figure 23A:
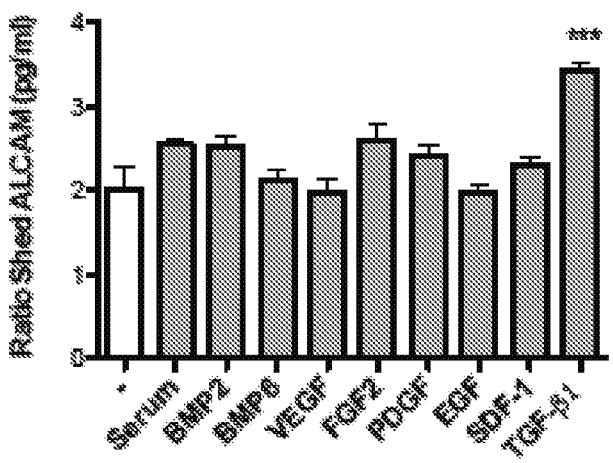
FIG. 23 shows that the expression and shedding of ALCAM is increased in response to TGFβ. (A) ELISA analysis of ALCAM shedding in concentrated conditioned media of PC3 cells treated with indicated exogenous cytokines. TGFβ, $p<0.001$ (B) Expression of ALCAM by RT-PCR fold change relative to GAPDH, glyceraldehyde 3-phosphate dehydrogenase in PC3 or LNCaP cells treated with or without 10 ng/ml of TGFβ for 48 hrs (C) Western blot analysis of shed ALCAM in the conditioned media and intact ALCAM in the cell lysate in LNCaP and PC3 cells. D) Western blot detection of ALCAM and Phospho-smad2 expression in PC3 cells treated with 10 ng/ml TGFβ for 48 hrs in the presence or absence of 10 μM SB431542. (E) RT-PCR and F) Western blot analysis of ALCAM expression in LNCaP cells transfected with vector control or T204D, dominant active TGFβ type I receptor; *$p<0.05$, **$p<0.01$.
Figure 23B:
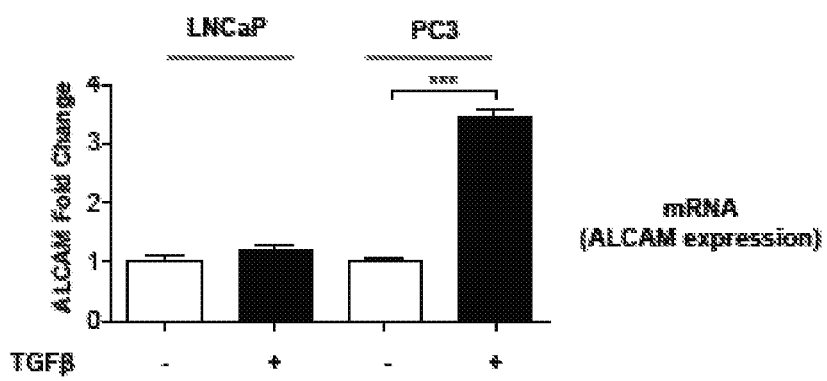
Figure 23C:
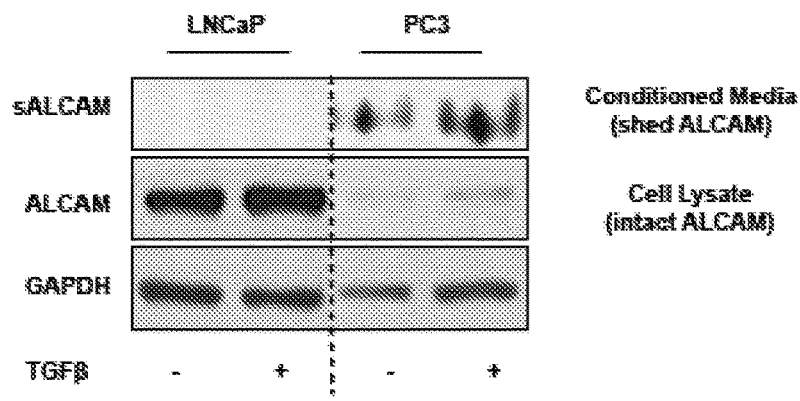
Figure 23D:
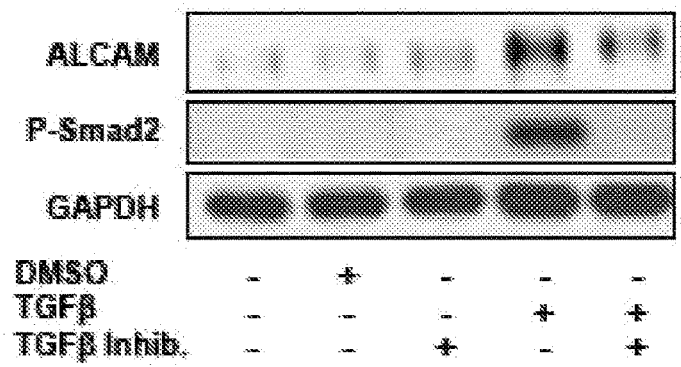
Figure 23E:
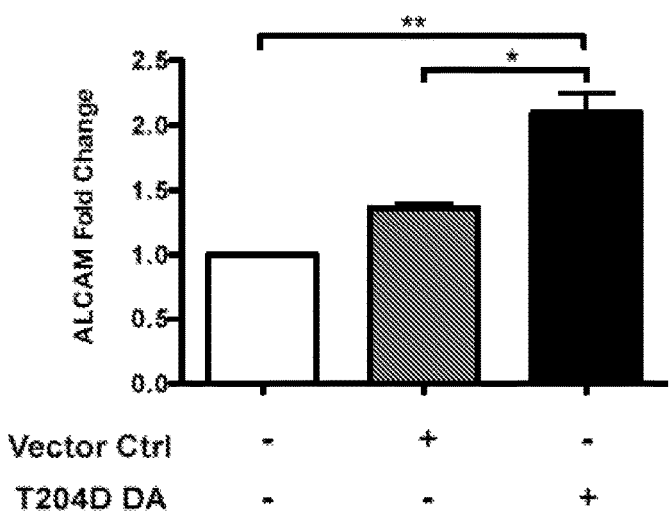
Figure 23F:
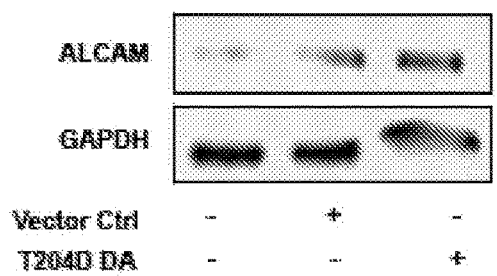

ALCAM is proteolytically shed from PC3 cells (FIG. 21). Absence of the cytoplasmic tail confirms that the ectodomain is shed (FIG. 21A). Moreover, ALCAM is absent from PC3-derived exosomes ensuring that the ectodomain is shed and not released with cell-derived microparticles (FIG. 21B). Since prostate cancer disseminates predominantly to bone we selected cytokines thought to be involved in this process, including TGFβ. Of the 8 agents tested, TGFβ promoted ALCAM shedding relative to overall total protein increase (FIG. 23A). To further explore the response to exogenous stimulation with TGFβ, ALCAM expression in PC3 cells was compared to ALCAM expression in LNCaP cells which are unable to respond to the cytokine because they lack TGFβ receptor type I (FIGS. 23B and 23C). Quantitative RT-PCR analysis for ALCAM demonstrates that TGFβ was also able to induce ALCAM gene transcription in PC3 but not LNCaP cells (FIG. 23B). The cytokine also increased levels of ALCAM protein expression and ectodomain shedding (FIG. 23C). Conversely, LNCaP did not respond to TGFβ even though these cells express abundant ALCAM (FIG. 23C). TGFβ-induced expression in PC3 cells could be abrogated with the small molecule inhibitor SB431542 (FIG. 23D, 10 μm; Sigma) while TGFβ-induced ALCAM mRNA and protein expression could be restored in LNCaP cells when the cells were transfected with dominant-active TGFβ receptor type I (FIGS. 23E and 23F).

ALCAM Shedding In Vivo Correlates with Tumor Progression

To determine if tumor-derived ALCAM is the source of elevated circulating ALCAM, species-specific antibodies were used to monitor circulating levels of both host (mouse) ALCAM and tumor (human) ALCAM longitudinally during orthotopic and subcutaneous growth of PC3 cells (FIG. 24).

Figure 25:
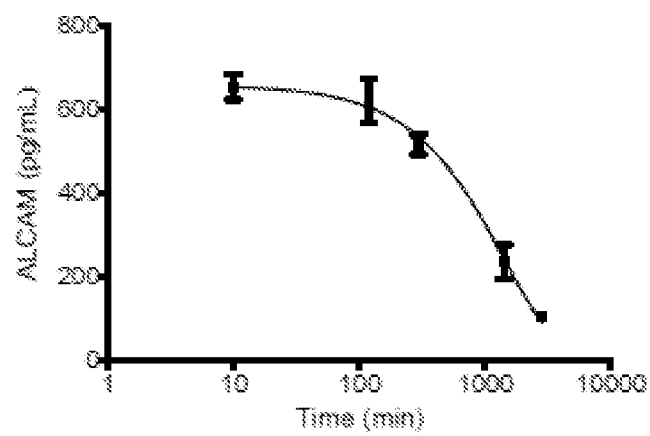
FIG. 25 shows a graph of ALCAM serum half-life in mice.

The half-life of human ALCAM in the circulation of its mouse host was determined to confirm that tumor-derived ALCAM could act as a stable biomarker in vivo (FIG. 25). Circulating ALCAM exhibits a 17 hr half-life which is sufficient for monitoring its release from an endogenous tumor burden.

Figure 26A:
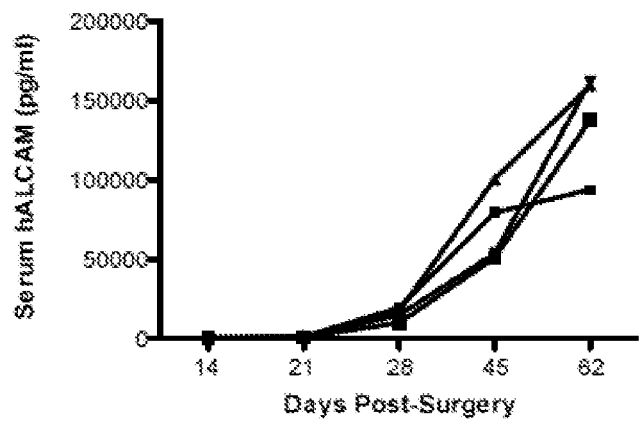
FIG. 26 shows that the immune response modulation does not effect serum ALCAM. A) Tumor-derived (human) ALCAM serum levels in individual mice plotted longitudinally B) Serum levels of mouse ALCAM pre- and post-treatment with Lipopolysaccharide (LPS). Data are mean±SEM (n=5); *$p<0.05$ (One-way ANOVA; Mann-Whitney test). C) Serum levels of mouse ALCAM in pre- and post full thickness skin punch. Data are mean±SEM (n=6); *$p<0.05$ (One-way ANOVA; Mann-Whitney test).
Figure 26B:
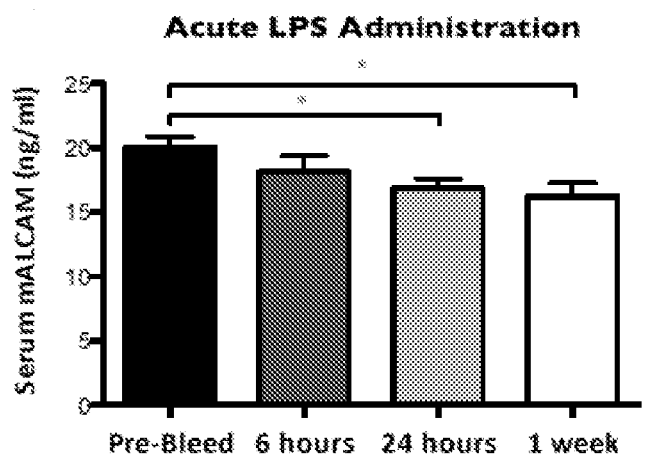
Figure 26C:
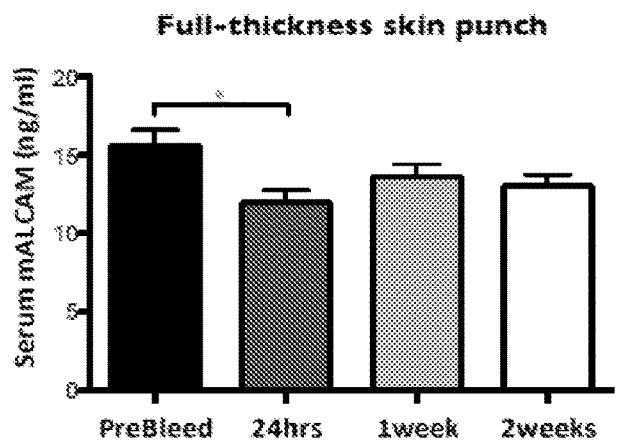

Circulating levels of ALCAM were subsequently monitored on a weekly basis (FIG. 24A) in SCID mice bearing subcutanous (FIG. 24B, n=5) or orthotopic xenografts of PC3 (FIG. 24C, n=8). Animals were bled on a pre-determined schedule via saphenous vein puncture. Circulating ALCAM levels were detected by ELISA and a comparison to pre-grafting baseline levels allowed for the detection of any increase in host (mouse) ALCAM and the appearance of tumor (human) ALCAM in response to an increasing tumor burden. Tumor-derived ALCAM levels showed significant weekly increases in the serum of tumor-bearing mice (FIGS. 24B, 24C, and 26; $P<0.0001$). Regression analysis showed a direct linear relationship between circulating levels of tumor-derived ALCAM and tumor burden for subcutaneous xenografts (FIG. 24B; tumor-derived $R^2=0.707$, $p<0.0001$, n=4) and orthotopic xenografts (FIG. 24C; tumor-derived $R^2=0.7066$, $p<0.0001$, n=4). In contrast to tumor-derived ALCAM, changes in host-derived ALCAM did not correspond to tumor burden (FIG. 24B; host-derived $R^2=0.03671$, n=4 animals; FIG. 24C; host-derived $R^2=0.01358$, n=4 animals).

ALCAM Shedding is Mediated by ADAM17 In Vitro and In Vivo

Figure 27A:
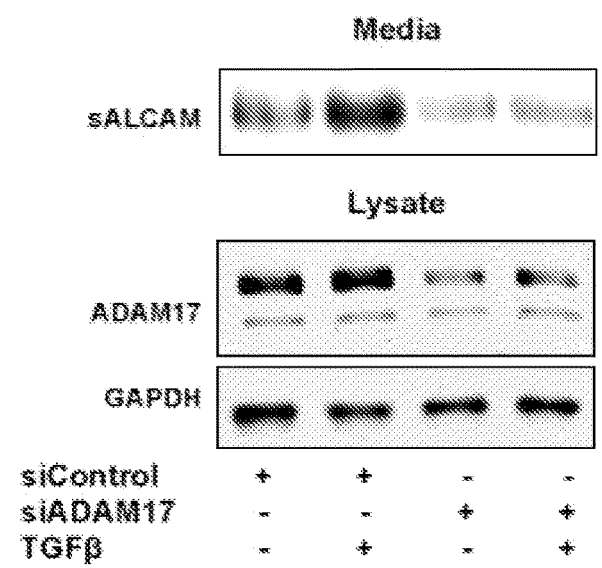
FIG. 27 shows (A) a Western blot analysis of shed ALCAM in the conditioned media and ADAM17 in the total cell lysate of PC3 transiently transfected with either scrambled siRNA or siRNA targeting ADAM17, (B) a Western blot analysis of shed ALCAM in PC3 cells treated with an ADAM17-specific inhibitor (Compound-32, BMS), broad-spectrum MMP inhibitor (GM6001), or diluent control, and (C) a graph of serum levels of tumor-derived ALCAM in 10 wk old SCID mice bearing PC3-luc tumors and treated with DMSO diluent or Compound-32 for three days, $p=0.0005$
Figure 27B:
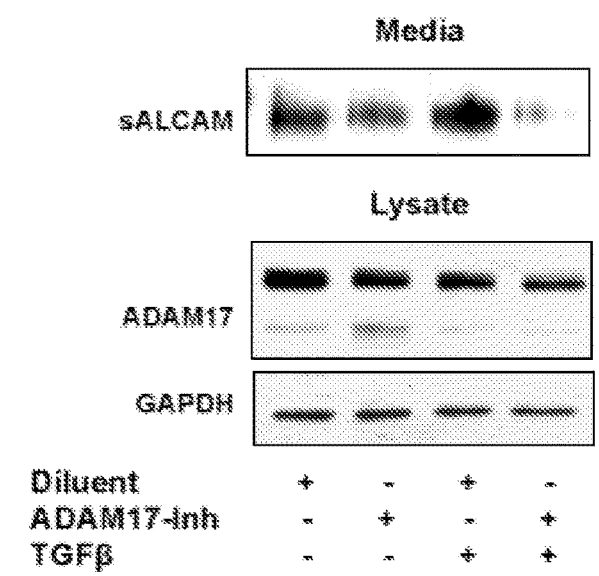
Figure 27C:
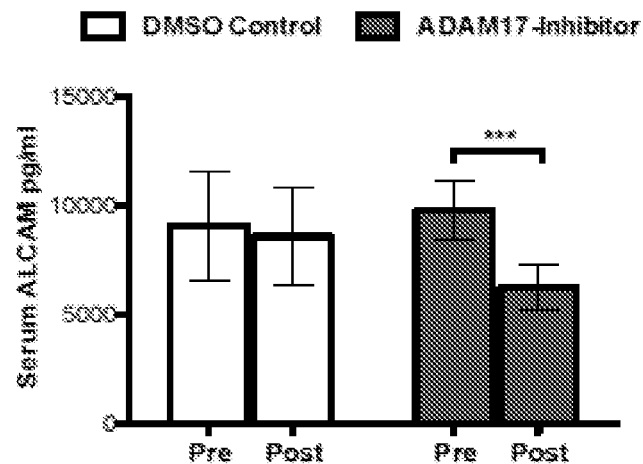
Figure 28:
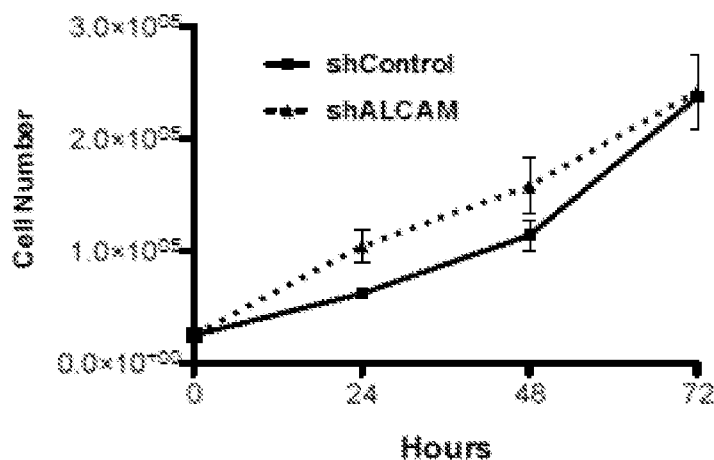
FIG. 28 shows a plot of compound-32/ADAM17 inhibitor dosing in vivo.

Knockdown of ADAM17 using small interfering RNA (siRNA) transfection resulted in a loss of TGFβ-induced ALCAM shedding (FIG. 27A). Similar results were obtained using an ADAM17-specific inhibitor (FIG. 27B, Compound-32, BMS). These studies were extended to orthotopic models to confirm that ADAM17 was also the primary protease responsible for ALCAM shedding in vivo (FIG. 27C). In vivo inhibitor dosing and efficacy was confirmed using serum TNF-alpha (FIG. 28, n=6) which demonstrated that 50% inhibition of ADAM17 could be achieved for the duration of the ALCAM serum half-life (FIG. 25; 17 hr) without signs of distress or toxicity. Mice were treated twice-daily for 3 days with 20 mg/kg of the ADAM17 inhibitor (Compound-32 or vehicle DMSO control). Pre-surgery, weekly, pre- and post-treatment saphenous vein bleeds were collected. Inhibition of ADAM17 resulted in a significant decrease in serum levels of shed ALCAM approximating the 50% inhibition we achieved with our dosing studies (FIG. 28). Taken together these data suggest that ALCAM cell surface shedding is mediated by ADAM17 and promoted by TGFβ.

Figure 29A:
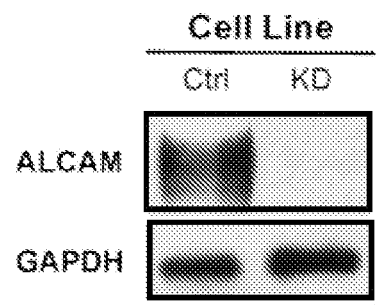
FIG. 29 shows (A) Western blot analysis of lysates from parental PC3-luc and PC3-luc shRNA ALCAM (KD1) knockdown cells, (B) quantitative analysis of tumor cell migration in parental PC3 cells and PC3 cells with shRNA-mediated knockdown of ALCAM treated with or without 10 ng/ml TGFβ, C) whole animal luciferase imaging of mice bearing orthotopic PC3-luc parental tumors or PC3-luc ALCAM knockdown tumors 6-weeks post surgery, (D) primary tumor weights of orthotopic PC3-luc parental tumors (n=8) and PC3-luc ALCAM knockdown tumors (n=8), (E) representative whole-animal luciferase imaging and matching x-rays 8 weeks post-intracardiac injection of PC3-luc parental (shControl) or PC3-luc ALCAM knockdown (shALCAM, KD1), and (F) a plot of average number of bone lesions in mice from PC3-luc (1.42±0.26; n=31) or PC3-luc shRNA ALCAM (KD1) knockdown cells (0.16±0.07; n=25). **$p<0.0001$.
Figure 29B:
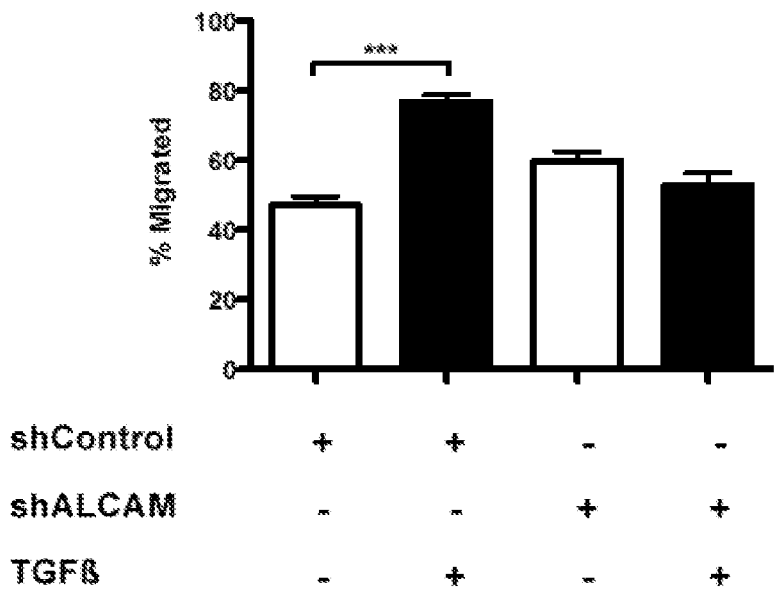

Knockdown of ALCAM in PC3 Cells Inhibits TGFβ-induced Migration and In Vivo Dissemination to Bone To test whether ALCAM is functionally involved in tumor cell migration and metastasis, expression in PC3-Luc cells was knocked down using viral delivery of short hairpin RNA (shRNA). Three separate stable ALCAM knockdowns were produced (ALCAM KD1, 2 and 3). Transduced cells were selected with puromycin and subsequently subjected to flow-sorting to isolate the highest knockdown population (FIG. 29A). PC3-luc-ALCAM$^{KD1}$ cells and PC3-luc-ALCAM shControl cells were pretreated with 10 µg/ml TGFβ1 for 16 hrs in serum-free conditions, followed by initiation of MAtS assay (FIG. 29B) or scratch assay (data not shown). TGFβ1 pre-treatment and treatment were compared at the time of scratch and exhibited similar results. The analysis revealed a loss TGFβ-induced migration in PC3-luc-ALCAM$^{KD1}$ cells (FIG. 29B) similar observations were made in ALCAM$^{KD2}$ and ALCAM$^{KD3}$ cells. The reduction in ALCAM expression led to a slight increase in migration, possibly due to a loss of ALCAM-ALCAM homotypic interaction on adjacent cells.

Figure 29C:
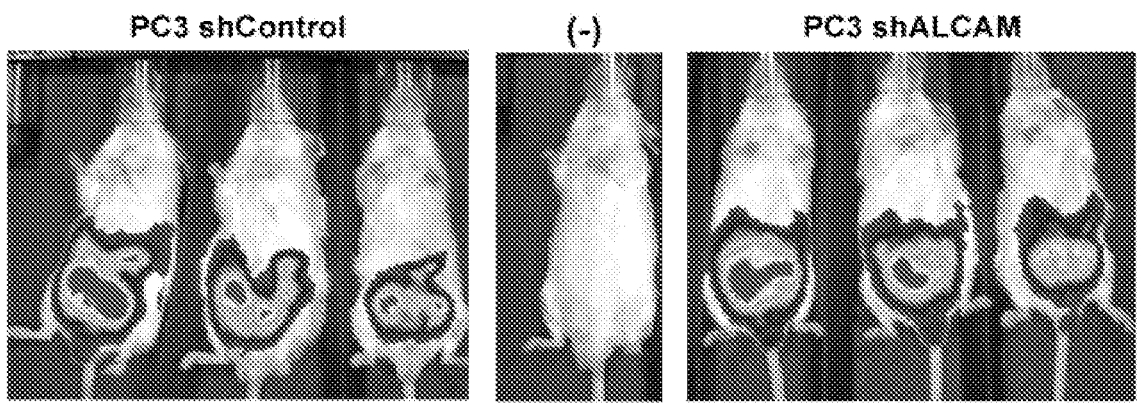
Figure 29D:
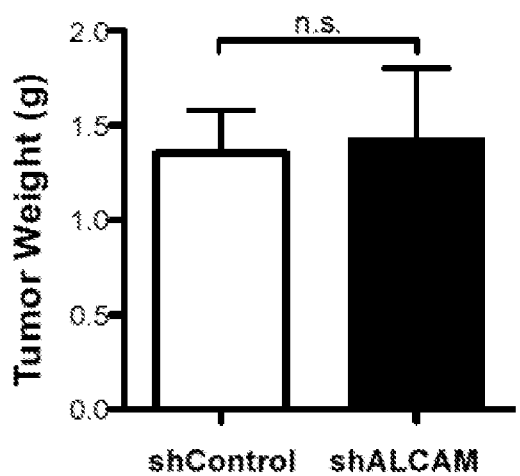

Given the critical importance of cancer cell migration in malignant tumor expansion and metastasis, the contribution of ALCAM to primary tumor growth and bone metastasis was evaluated. Primary tumor growth was accomplished using an orthotopic model based on implantation of tumor cells into the anterior prostate of SCID mice (FIG. 29C, n=8 for PC3-luc-Control and PC3-luc-ALCAM$^{KD1}$). Skeletal metastasis was accomplished by intracardiac injection of tumor cells in nude mice (FIG. 5D, n=31 for PC3-luc-Control and n=25 for PC3-luc-ALCAM$^{KD1}$). Bioluminescent imaging was used to monitor tumor burden for both models at weekly intervals. Reduced ALCAM expression did not limit tumor growth within the prostate (FIG. 29C). Whole body and ex vivo bioluminescent imaging of the orthotopic model upon experiment completion confirmed that both the PC3-luc-Control and PC3-luc-ALCAM$^{KD1}$ exhibited similar tumor burden based on luciferase activity (FIG. 29C), and comparable tumor size based on weight (FIG. 29D). Local invasion and mesenteric dissemination is common in this model and was not altered by reduced ALCAM expression.

Figure 29E:
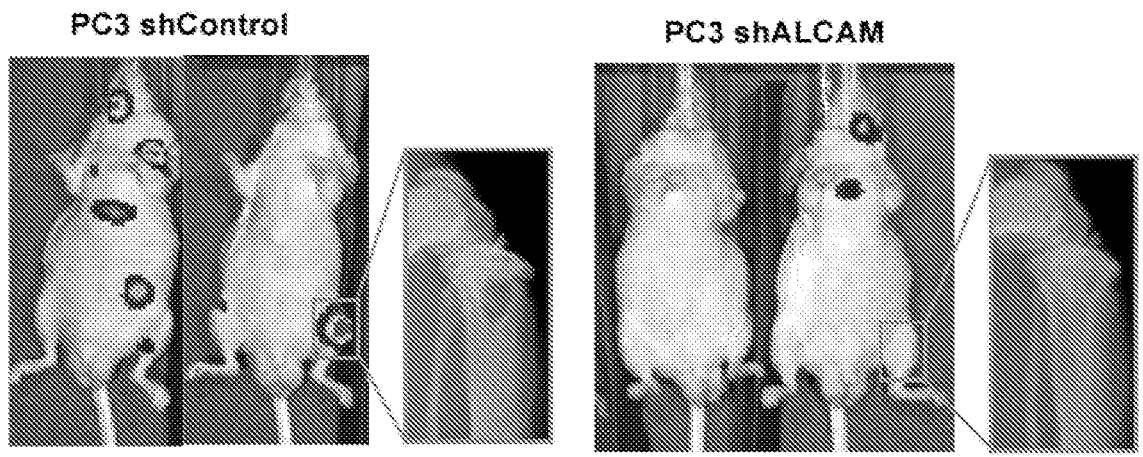
Figure 29F:
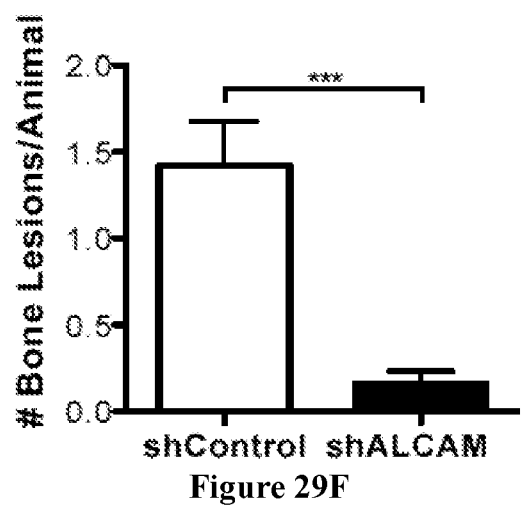

In contrast to the orthotopic model, a reduction in ALCAM resulted in a significant decrease in skeletal metastasis (FIG. 29E). Both incidence and metastatic burden were reduced. Approximately 75% of mice injected with PC3-luc-Control tumor cells developed bone metastasis while only 17% of the mice injected with PC3-luc-ALCAM$^{KD1}$ cells developed bone lesion. In addition, mice that did develop skeletal metastases formed by PC3-luc-ALCAM$^{KD1}$, the number of lesions per mouse was greatly reduced (0.2 events versus 1.4 events FIG. 29F). The orthotopic and intracardiac experiments were repeated with PC3-luc-ALCAM$^{KD3}$ and similar results obtained.

Figure 30A:
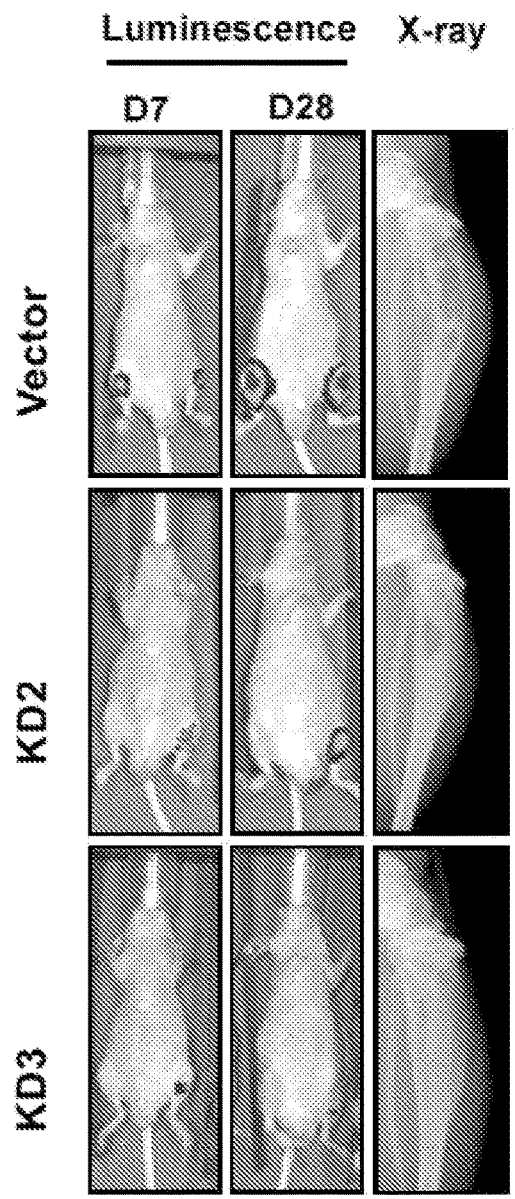
FIG. 30 shows (A) a representative whole animal luciferase and x-ray imaging of mice post-intratibial injection of PC3-luc parental tumors (vector, n=8), and PC3-luc ALCAM knockdown tumor cells (KD2, n=8 & KD3, n=8), (B) Collagen I and ALCAM immunoflurescence of tumor cells within the tibias of mice bearing PC3-luc vector or PC3-luc KD2 or KD3 tumors, (C) bioluminescent curve of intratibial tumor development in mice bearing PC3-luc vector, PC3-luc KD2 and KD3 tumors. (Two-way ANOVA with Bonferroni post-test), and (D) tumor incidence and average lesion area in the tibias of mice bearing PC3-luc vector, PC3-luc KD2 and KD3 tumors. Data represent the mean±SEM (n=8/group); $p<0.01$; *$p<0.0001$
Figure 30B:
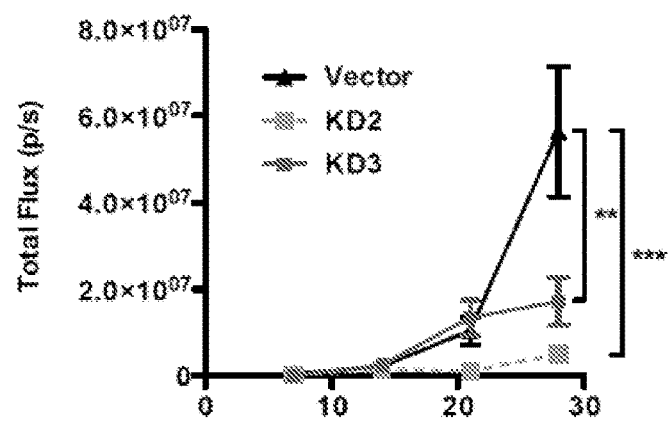
Figure 30C:
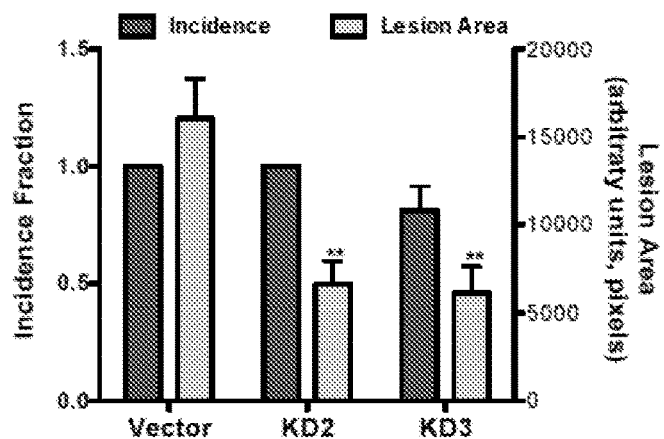
Figure 30D:
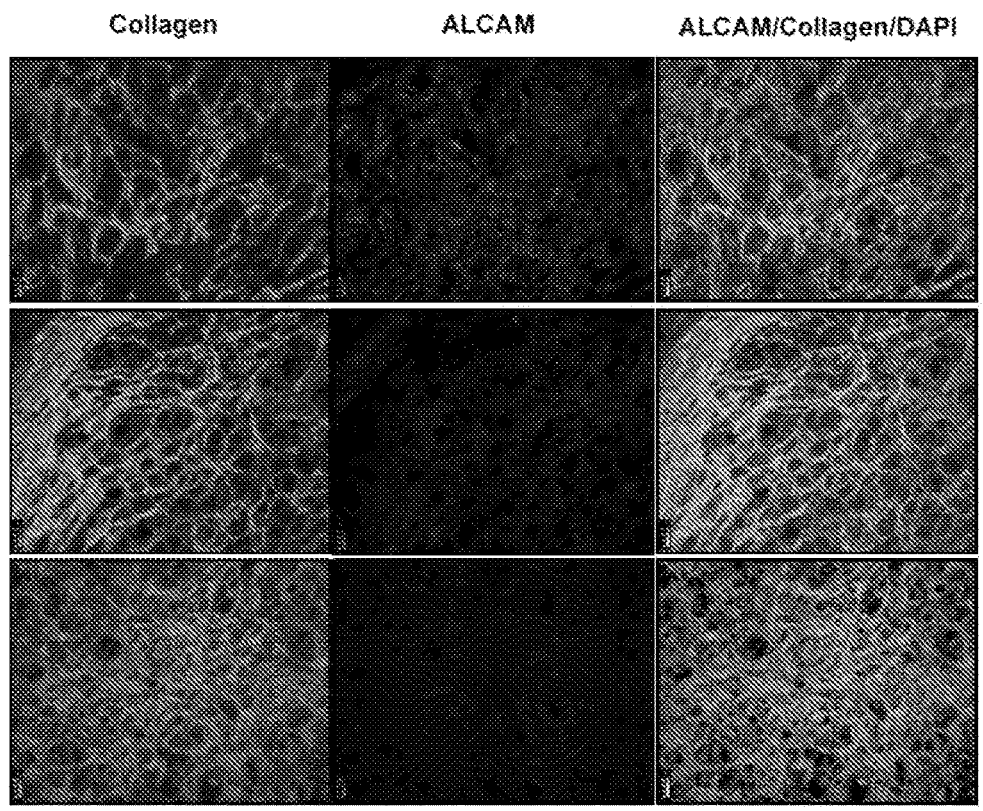
Figure 31A:
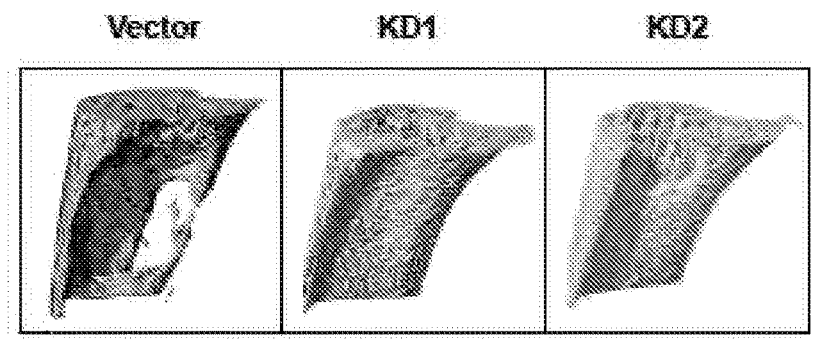
FIG. 31 shows that tumor-derived ALCAM impacts tumor survival in the bone microenvironment of intratibial bone tumor model. A) Representative three dimensional reconstitutions of microCT images from mice injected with PC3-luc-vector, PC3-luc-KD1 and PC3-luc-KD2 tumor cells. B) Boxplots of average BV/TV (bone volume/total volume) by group for the PC3-luc-vector, PC3-luc-KD2 and PC3-luc-KD3 tumor bearing mice. Data represents quartiles with dots indicating outliers (1.5x upper or lower quartile; n=16 tibias/group) *$p<0.05$, **$p<0.01$. C) A boxplot representing the lesion area calculated from end-point x-ray images from the same experiment. D) Representative H&E stains of osteolytic bone lesions in the hind leg of mice. Outlines indicate the osteolytic tumor lesion within the bone. E) Representative immunofluorescent staining of cleaved caspase-3 positive cells (red) in tibias of PC3-luc-vector, PC3-luc-KD2 and PC3-luc-KD3 tumor-bearing mice. F) Representative immunofluorescent staining of Ki67 proliferating cells (red) in tibias of PC3-luc-vector, PC3-luc-KD2 and PC3-luc-KD3 tumor-bearing mice. Data are mean±SEM (n=8/group); *$p<0.05$, $p<0.01$, *$p<0.005$. G) A plot of apoptosis in the tumor-bone microenvironment as a function of total cell number assessed by staining for cleaved caspase-3 in PC3-luc-vector, PC3-luc-KD2 and PC3-luc-KD3 tumor bearing tibias of mice 4 weeks post-injection. H) A plot of proliferation in the tumor-bone microenvironment as a function of total cell number assessed by staining for Ki67 in PC3-luc-vector, PC3-luc-KD2 and PC3-luc-KD3 tumor bearing tibias of mice 4 weeks post-injection.
Figure 31B:
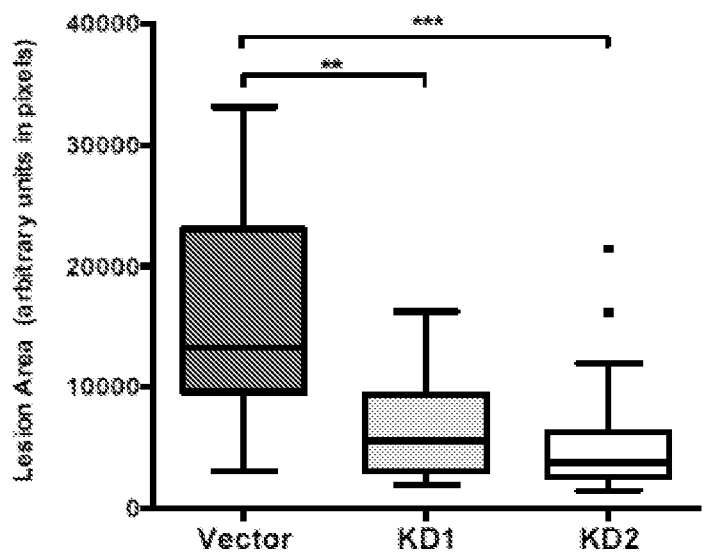
Figure 31C:
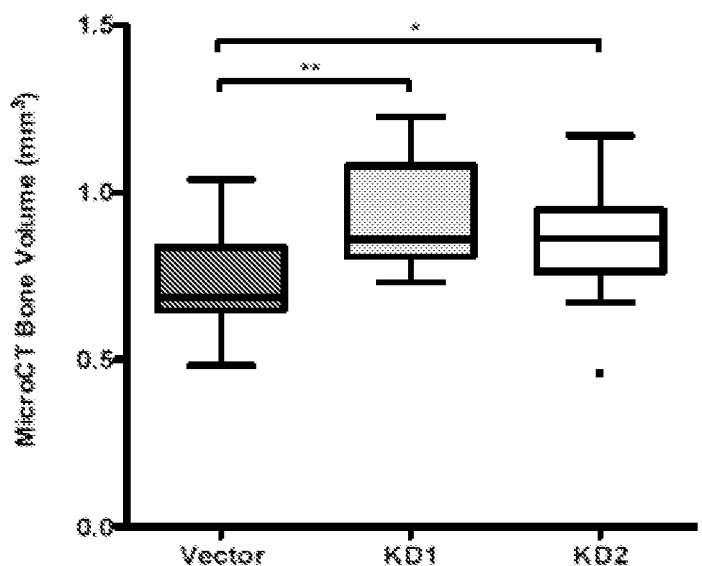
Figure 31D:
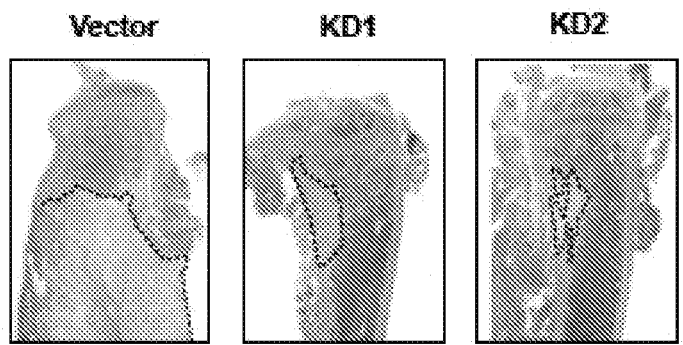
Figure 32:
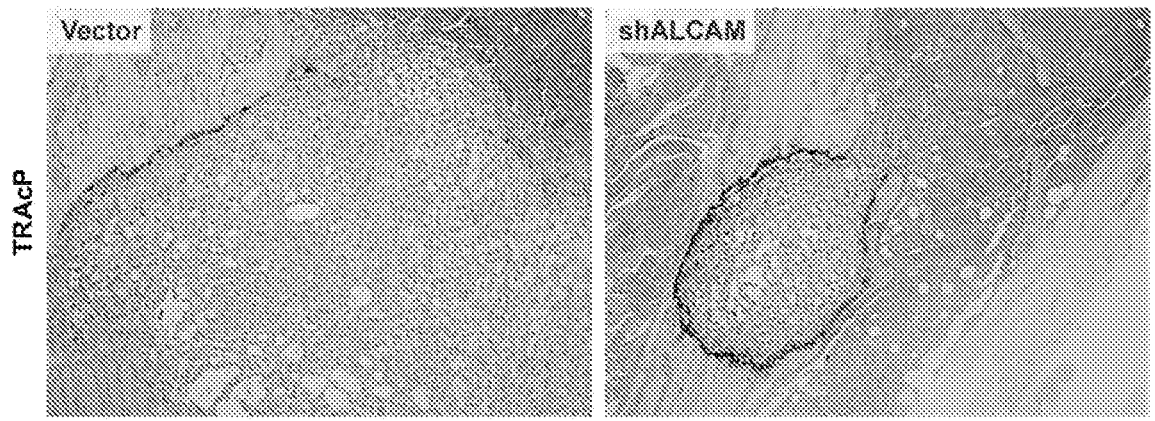
FIG. 32 shows a graph of tumor cell proliferation over time assessed by total cell counts over 72 hours.

ALCAM Expression Contributes to Tumor Cell Survival in the Bone Microenvironment To determine the biologic importance of tumor-derived ALCAM in prostate tumor growth in the bone, PC3-luc-Control (n=8), PC3-luc-ALCAM$^{KD2}$ (n=8) and PC3-luc-ALCAM$^{KD3}$ (n=8) were injected into the tibia of nude mice. Following intratibial injection, luminescent and X-ray imaging was used to monitor tumor burden over time (FIG. 30A). Quantitation of the bioluminescent signal showed a lower growth rate for the ALCAM KD cells (FIG. 30B). At completion of the experiment 100% of control mice exhibited lesion compared to an 80% incidence in limbs bearing PC3-luc-ALCAM$^{KD3}$ tumor cells (FIG. 30C). ALCAM$^{KD}$ intratibial tumors continued to exhibit reduced ALCAM expression (FIG. 30D). Detailed imaging of the osteolytic lesions by microCT (FIG. 31A) further confirmed decreased lesion area and increased bone volume in the bones containing ALCAM KD cells (FIGS. 31B and 31C). Finally, the histological visualization of bone tumors generated by control and ALCAM KD cells resulted in reduced bone tumor size upon ALCAM knockdown (FIG. 31D). Tibias in the PC3-luc-vector, PC3-luc-ALCAM$^{KD2}$ and PC3-luc-ALCAM$^{KD3}$ were stained for the osteoclast marker, tartrate-resistant alkaline phosphatase (FIG. 32). Both the ALCAM KD tumors induced osteolytic lesions as evidenced by osteoclast presence adjacent to tumor lesions suggesting that the ability to induce bone-remodeling was not deficient in these cells.

Figure 31E:
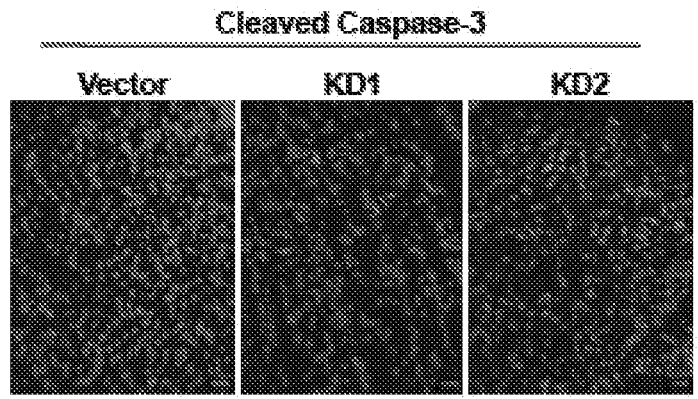
Figure 31F:
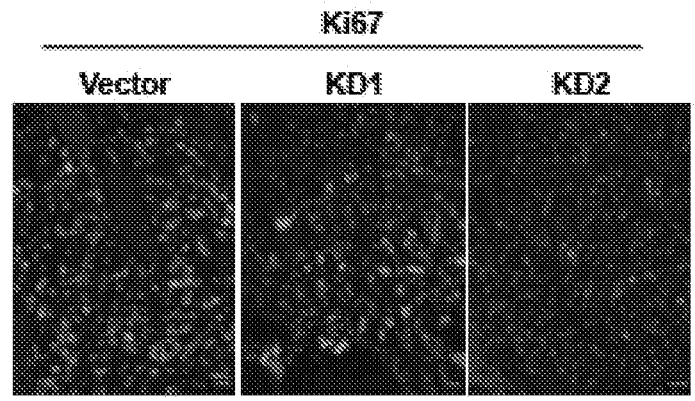
Figure 31G:
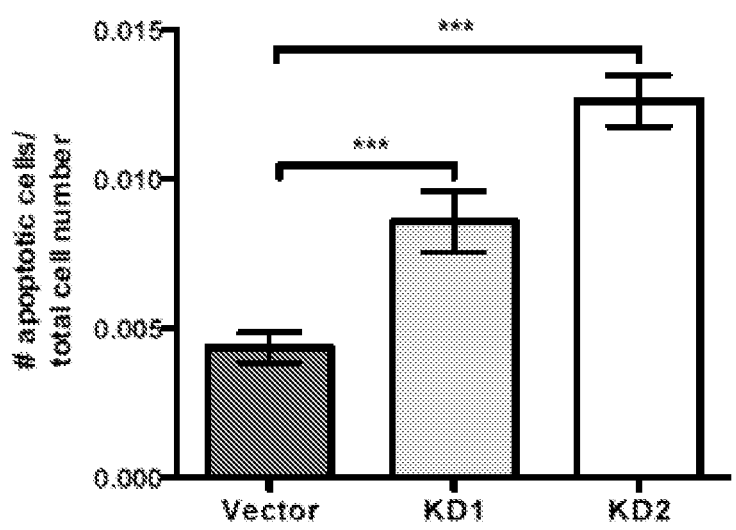
Figure 31H:
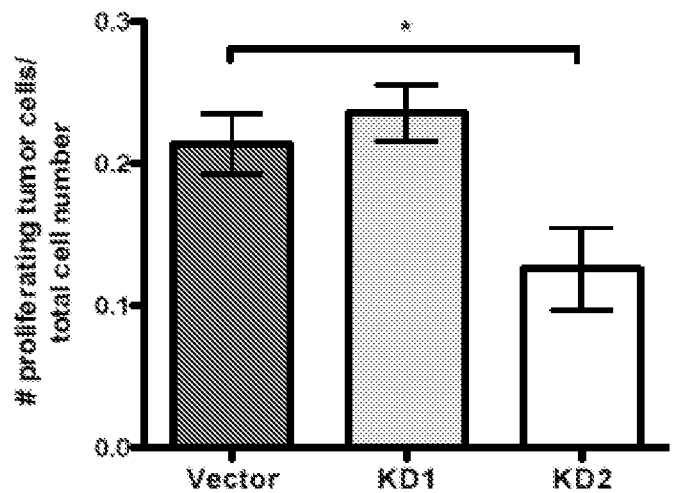

Immunofluorescent staining was performed for cleaved caspase-3 (FIG. 31E, apoptosis) and Ki67 (FIG. 31F, proliferation) on intratibial bone tumors harvested at 28 days post injection Compared to the control tumors, the bone tumors created by both ALCAM KD cells exhibited elevated levels of cleaved caspase-3 suggesting that these cells are experiencing a reduced ability to survive (FIG. 31G). In addition, bone tumors from PC3-luc-ALCAM$^{KD3}$ had significantly lower Ki67 staining suggesting that ALCAM contributes to both proliferation and survival (FIG. 31H).

Discussion

Figure 21A:
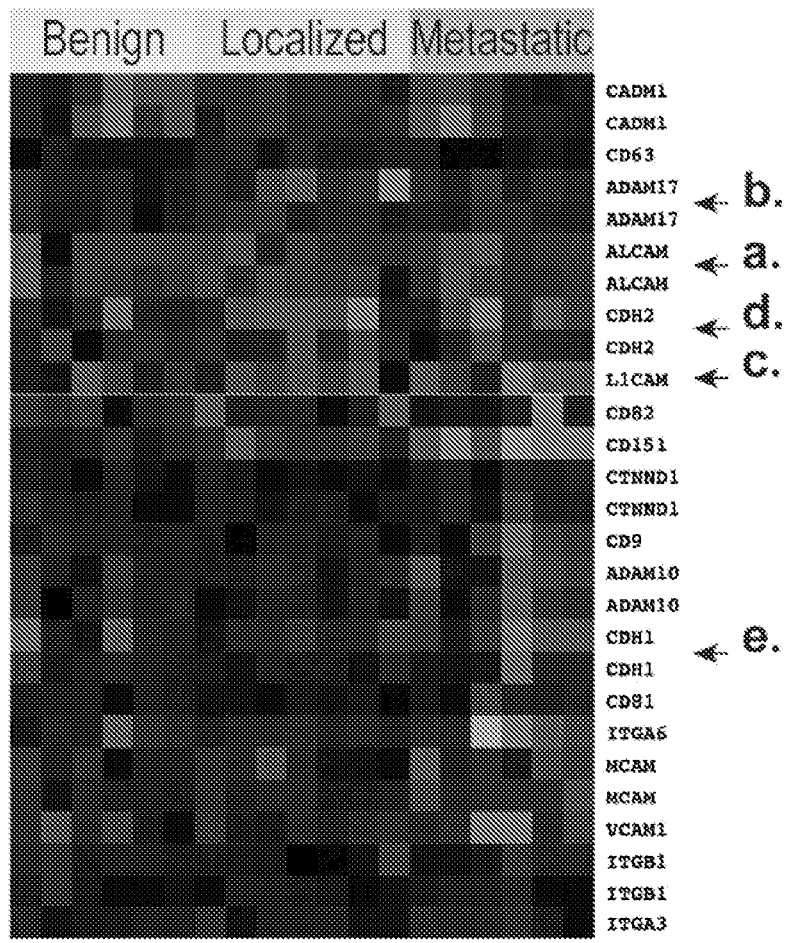
FIG. 21 shows that ALCAM is overexpressed metastatic prostate cancer and correlates with patient survival. (A) Heat map and corresponding relative expression of ADAM17 (i) ALCAM (ii) N-cadherin (iii), p120 (iv) and E-cadherin (v) indicated by arrows. (B) Representative images from immunohistochemical staining of ALCAM membranous and cytoplasmic expression in benign to metastatic prostate cancer. (C) Correlation of ALCAM expression to overall survival in a publicly available dataset (code) composed of 600 prostate cancer patients. Kaplan-Meier survival curves represent the upper and lower quartile ALCAM expression.
Figure 21B:
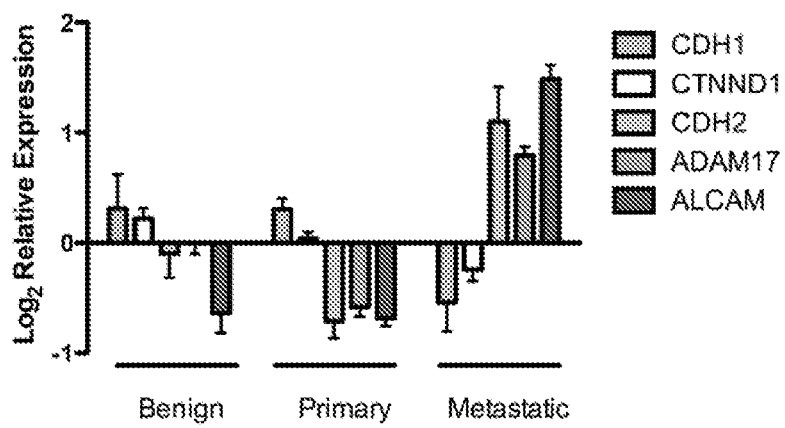
Figure 21C:
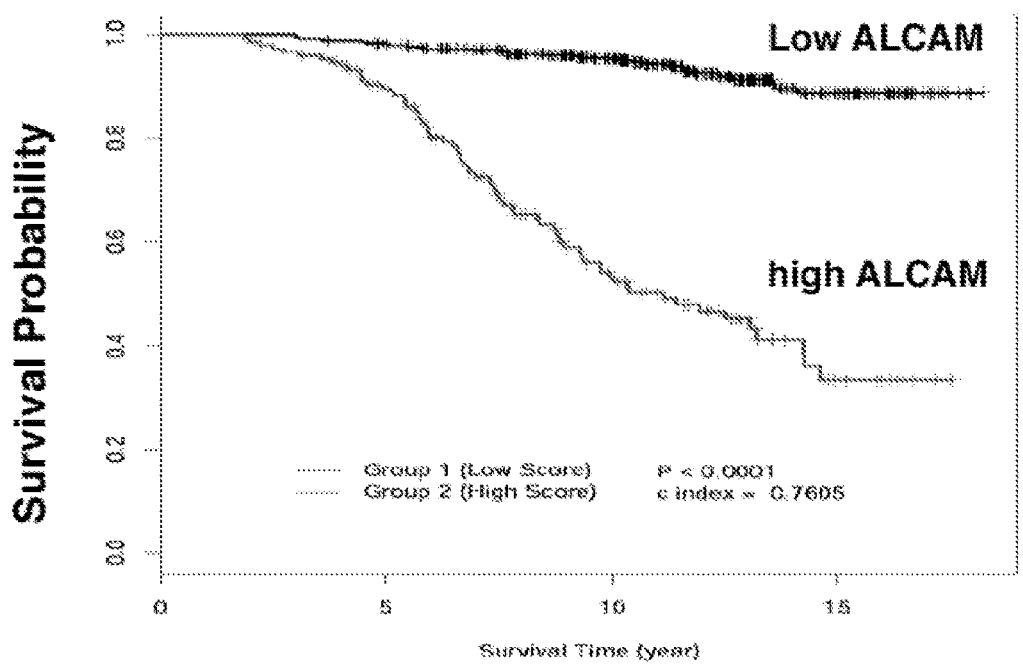
Figure 21D:
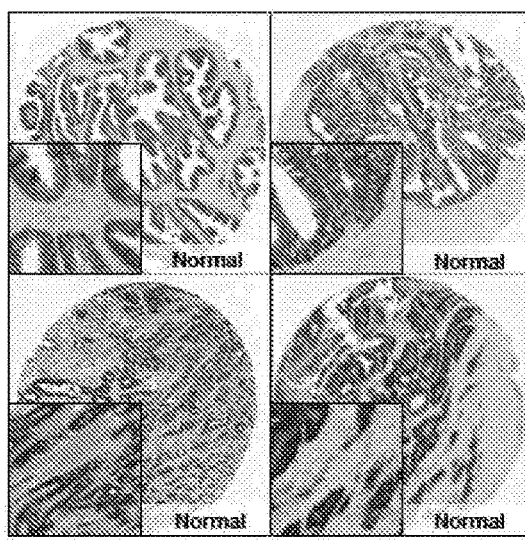
Figure 22A:
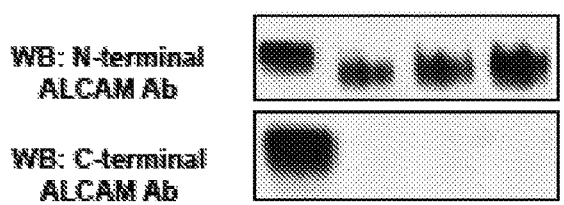
FIG. 22 shows A) Western blot analysis of ALCAM shedding in conditioned media of LNCaP and PC3 cells treated with or without 10 ng/ml of TGFβ using antibodies specifically recognizing the extracellular and intracellular domains, and B) ALCAM shedding in response to 10 ng/ml TGFβ after 48 hours as measured by Western blotting of ALCAM and CD151 (exosome marker) in PC3 tumor cell conditioned media. "Total CM"=total conditioned media, "CM Supernatant"=conditioned media supernatant without exosome pellet, "Exosome pellet"=exosome pellet resuspended in phosphate buffered saline.
Figure 22B:
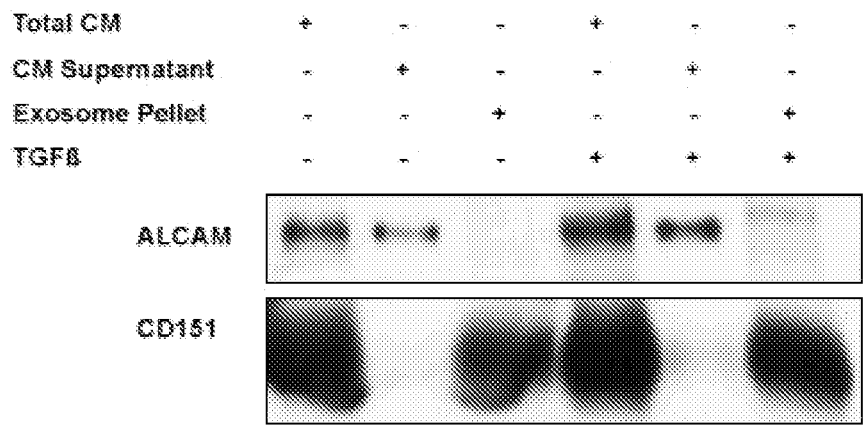

The data reveals that ALCAM plays a role in prostate cancer establishment in the bone microenvironment. ALCAM mRNA is elevated in malignant disease yet by immunohistochemistry it is frequently absent from the tumor cell surface in advanced disease (FIG. 24D). In colorectal cancer, ectodomain shedding is responsible for the apparent loss of ALCAM detection. This shedding is likely the cause for conflicting results reported for several malignancies. Indeed the protease responsible for shedding of ALCAM ectodomain (ADAM17), is elevated in advanced prostate cancer (FIG. 21B). This data implies that, while ALCAM gene transcription is elevated in prostate cancer, ectodomain shedding depletes the cell surface of intact protein in advanced disease. Regression analysis showed a direct linear relationship between circulating levels of (human) tumor-derived ALCAM and tumor burden in animals with subcutaneous xenografts (FIG. 24B) and orthotopic xenografts (FIG. 24C). In contrast, the host-derived ALCAM did not correspond to tumor burden (FIGS. 24B and 24C), demonstrating that elevations in circulating ALCAM are tumor-specific. Consistent with this observation, host-derived ALCAM does not increase, but rather decreases slightly, in immunocompetent mice challenged LPS (a model of acute inflammation) or full-thickness skin punch (a model for wound-healing, FIGS. 24B and 24C, respectively). These data suggest that tumor-derived ALCAM is a marker specific of tumor burden and that host ALCAM is not significantly shed in response to the tumor burden.

Suppression of ALCAM expression using gene-specific shRNAs prevented TGFβ induced migration in vitro (FIG. 29B) and inhibited metastasis as well as tumor growth in bone in vivo (FIGS. 29-31). These observations demonstrate that ALCAM is not only a marker of cancer progression but also a significant regulator of tumor cell migration and metastasis to bone. Within the metastatic cascade there are many sequential steps that can contribute to the overall success of any single metastatic lesion. Evaluation of the primary tumor within the prostate did not reveal any deficiency in growth or local invasion. Conversely, experimental metastasis by intracardiac injection resulted in nearly 10-fold reduction of skeletal metastasis (FIG. 29). This reduced metastatic incidence suggests that ALCAM is required for dissemination to the bone. Further examination tumor growth after intratibial injection (FIG. 30) revealed a significant inhibition in tumor growth without affecting the tumor incidence. The reduced metastatic incidence from circulating tumor cells (intracardiac injection) together with the reduced growth of the metastatic burden in the bone (intratibial injection) without further impact on incidence indicates that ALCAM contributes to metastatic dissemination as well as growth in the metastatic sites.

Although the role of ALCAM in extravasation was not be tested directly, it is possible that the requirement for transendothelial migration extends to metastatic tumor cells. The reduced metastatic incidence after intracardiac injections indeed supports that hypothesis (FIG. 29). The lesions that did arise from circulating PC3-luc-ALCAM$^{KD}$ cells were smaller than those generated from PC3-luc-Control cells suggesting an additional contribution from ALCAM to metastatic growth. Indeed, metastatic lesions generated after intratibial injection did not significantly impact tumor incidence (FIG. 30C) but did dramatically reduce expansion of the metastatic tumor burden (FIG. 31F).

Figure 33:
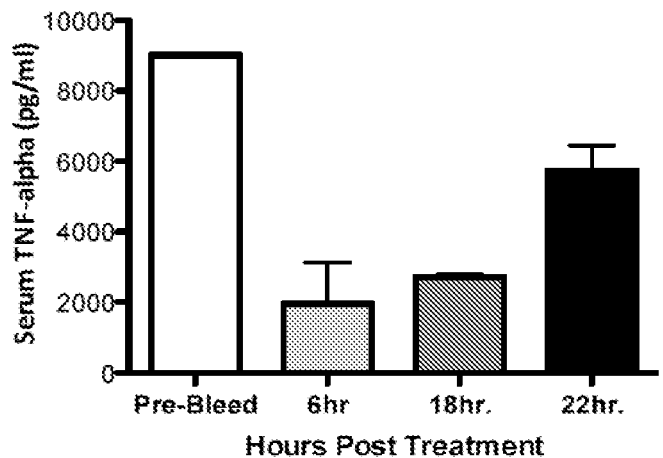
FIG. 33 shows representative TRAcP stained photomicrographs of PC3 shControl and shALCAM injected animals at day 28.
Figure 34A:
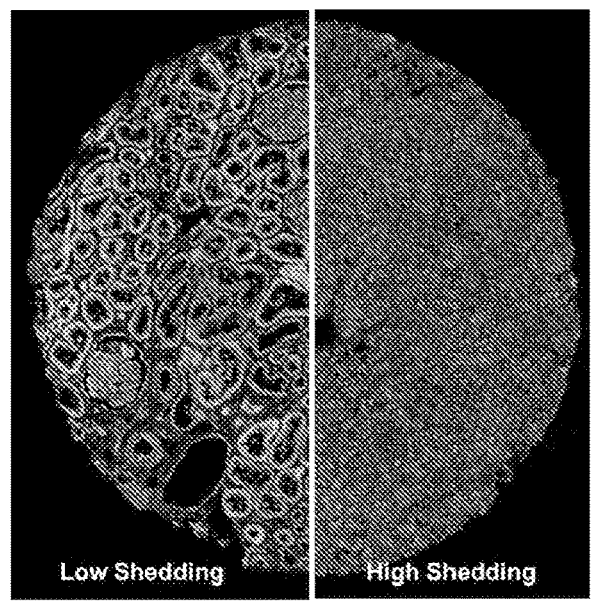
FIG. 34 shows the analysis of intra-tumoral ALCAM protein expression and shedding on a retrospective cohort of patients with clear cell renal cell carcinoma undergoing nephrectomy. A) Immunohistochemical staining for ALCAM with antibodies against the extracellular and intracellular domain. B) A plot showing ALCAM staining intensity, on a scale from 0-3, based on the signal observed in greater than 10% of tumor cells. C) A plot showing "shed" ALCAM as total ALCAM minus intact ALCAM. Overall survival was defined as time from date of nephrectomy to date of death or last follow-up. Recurrence was defined as time from date of nephrectomy to date of metastatic recurrence validated by imaging.
Figure 34B:
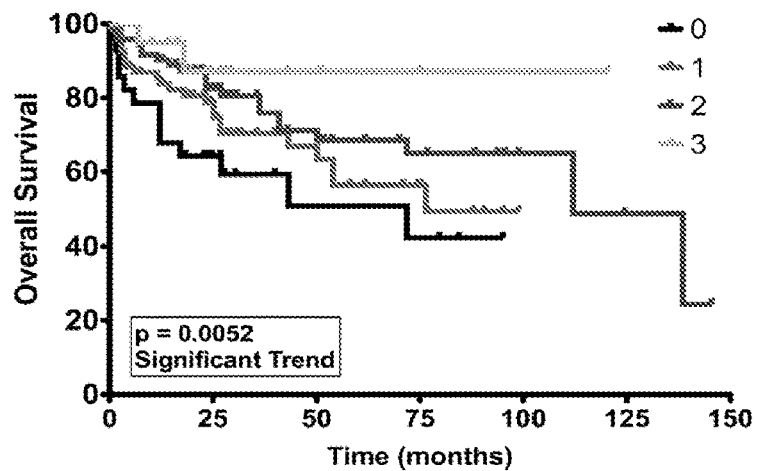
Figure 34C:
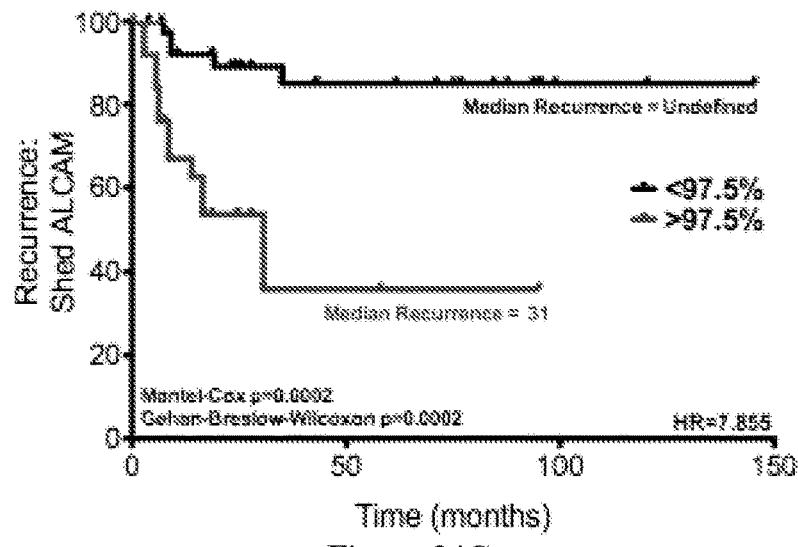

Intratibial tumors generated by PC3-luc-ALCAM$^{KD}$ did not re-express ALCAM (FIG. 29D) allowing further investigation of any molecular disparities between metastatic lesions that expressed ALCAM and those that did not. The abundant presence of osteoclast activity by TRAP staining (FIG. 32) in metastatic lesions of PC3-luc-ALCAM$^{KD}$ suggests that there is no deficiency in osteolysis. Nevertheless, these lesions remain significantly smaller than those created by PC3-luc-Control suggesting that there was not a lag in tumor growth but rather a persistent reduced ability to proliferate or, conversely, a decreased ability to survive. Although reduced proliferation in vitro was not observed (FIG. 33), in vivo metastatic lesions created by PC3-luc-ALCAM$^{KD}$ did exhibit reduced proliferation and increased apoptosis. Intriguingly, PC3-luc-ALCAM$^{KD2}$, which retains more ALCAM expression than PC3-luc-ALCAM$^{KD3}$ (FIG. 30A), did not exhibit reduced proliferation suggesting that the threshold of ALCAM expression that influences cell survival is different from the threshold influencing cell proliferation.

Together these observations suggest a dual adhesive and signaling function of ALCAM whereby the intracellular signaling function of ALCAM functions to serve a protective role in apoptosis, and the extracellular adhesive function is required for extravasation and subsequent colonization at a secondary site.

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "an antibody" includes a plurality of such antibodies, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Throughout this document, various references are mentioned. All such references are incorporated herein by reference, including the references set forth in the following list:

REFERENCES

1. Siegel R, Ward E, Brawley O, Jemal A. Cancer statistics, 2011. CA: A Cancer Journal for Clinicians. 2011; 61(4): 212-236.
2. Compton C C. Colorectal Carcinoma: Diagnostic, Prognostic, and Molecular Features. Mod Pathol. 2003; 16(4): 376-388.
3. Quasar Collaborative Group, Gray R, Barnwell J, McConkey C, Hills R K, Williams N S, et al. Adjuvant chemotherapy versus observation in patients with colorectal cancer: a randomised study. Lancet. 2007; 370(9604): 2020-2029.
4. Figueredo A. Adjuvant Therapy for Stage II Colon Cancer: A Systematic Review From the Cancer Care Ontario Program in Evidence-Based Care's Gastrointestinal Cancer Disease Site Group. Journal of Clinical Oncology. 2004; 22(16):3395-3407.
5. Midgley R, Kerr D J. Adjuvant chemotherapy for stage II colorectal cancer: the time is right! Nat Clin Pract Oncol. 2005; 2(7):364-369.
6. Johnston P G. Stage II colorectal cancer: to treat or not to treat. Oncologist. 2005; 10(5):332-334.
7. Eschrich S. Molecular Staging for Survival Prediction of Colorectal Cancer Patients. Journal of Clinical Oncology. 2005; 23(15):3526-3535.
8. Smith J J, Deane N G, Wu F, Merchant N B, Zhang B, Jiang A, et al. Experimentally Derived Metastasis Gene Expression Profile Predicts Recurrence and Death in Patients With Colon Cancer. Gastroenterology. 2010; 138 (3):958-968.
9. Ogino S, Nosho K, Irahara N, Shima K, Baba Y, Kirkner G J, et al. Prognostic Significance and Molecular Associations of 18q Loss of Heterozygosity: A Cohort Study of Microsatellite Stable Colorectal Cancers. Journal of Clinical Oncology. 2009; 27(27):4591-4598.
10. Lugli A, Iezzi G, Hostettler I, Muraro M G, Mele V, Tornillo L, et al. Prognostic impact of the expression of putative cancer stem cell markers CD133, CD166, CD44s, EpCAM, and ALDH1 in colorectal cancer. Br J Cancer. 2010; 103(3):382-390.
11. Gerger A, Zhang W, Yang D, Bohanes P, Ning Y, Winder T, et al. Common cancer stem cell gene variants predict colon cancer recurrence. Clin. Cancer Res. 2011; 17(21): 6934-6943.
12. Witzel I, Schröder C, Müller V, Zander H, Tachezy M, Ihnen M, et al. Detection of Activated Leukocyte Cell Adhesion Molecule in the Serum of Breast Cancer Patients and Implications for Prognosis. Oncology. 2012; 82(6):305-312.
13. Miccichè F, Da Riva L, Fabbi M, Pilotti S, Mondellini P, Ferrini S, et al. Activated leukocyte cell adhesion molecule expression and shedding in thyroid tumors. PLoS ONE. 2011; 6(2):e17141.
14. Mezzanzanica D, Fabbi M, Bagnoli M, Staurengo S, Losa M, Balladore E, et al. Subcellular Localization of Activated Leukocyte Cell Adhesion Molecule Is a Molecular Predictor of Survival in Ovarian Carcinoma Patients. Clinical Cancer Research. 2008; 14(6):1726-1733.
15. Hansen A, Swart G W, Zijlstra A. ALCAM[Internet]. UCSD Nature Molecule Pages. 2011; Available from: http://www.signaling-gateway.org/molecule/query?afcsid=A004126&type=abstract
16. Weichert W, Knösel T, Bellach J, Dietel M, Kristiansen G. ALCAM/CD166 is overexpressed in colorectal carcinoma and correlates with shortened patient survival. Journal of Clinical Pathology. 2004; 57(11):1160-1164.
17. Horst D, Kriegl L, Engel J, Kirchner T, Jung A. Prognostic Significance of the Cancer Stem Cell Markers CD133, CD44, and CD166 in Colorectal Cancer. Cancer Invest. 2009; 27(8):844-850.
18. Levin T G, Powell A E, Davies P S, Silk A D, Dismuke A D, Anderson E C, et al. Characterization of the Intestinal Cancer Stem Cell Marker CD166 in the Human and Mouse Gastrointestinal Tract. Gastroenterology. 2010; 139(6):2072-2082.e5.
19. Kristiansen G, Pilarsky C, Wissmann C, Stephan C, Weissbach L, Loy V, et al. ALCAM/CD166 is up-regulated in low-grade prostate cancer and progressively lost in high-grade lesions. Prostate. 2002; 54(1):34-43.
20. Kristiansen G, Pilarsky C, Wissmann C, Kaiser S, Bruemmendorf T, Roepcke S, et al. Expression profiling of microdissected matched prostate cancer samples reveals CD166/MEMD and CD24 as new prognostic markers for patient survival. J. Pathol. 2005; 205(3):359-376.
21. S R, Dent C, Watkins G, King J A, Mokbel K, Jiang W G. Expression of the cell to cell adhesion molecule, ALCAM, in breast cancer patients and the potential link with skeletal metastasis. Oncol Rep. 2008; 19(2):555-561.
22. Ishigami S, Ueno S, Arigami T, Arima H, Uchikado Y, Kita Y, et al. Clinical implication of CD166 expression in gastric cancer. J Surg Oncol. 2011; 103(1):57-61.
23. Tachezy M, Zander H, Marx A H, Gebauer F, Rawnaq T, Kaifi J T, et al. ALCAM (CD166) expression as novel prognostic biomarker for pancreatic neuroendocrine tumor patients. J. Surg. Res. 2011; 170(2):226-232.
24. van Kempen L C L T, Meier F, Egeblad M, Kersten-Niessen M J F, Garbe C, Weidle U H, et al. Truncation of activated leukocyte cell adhesion molecule: a gateway to melanoma metastasis. J Invest Dermatol. 2004; 122(5): 1293-1301.
25. Swart G W M. Activated leukocyte cell adhesion molecule (CD166/ALCAM): developmental and mechanistic aspects of cell clustering and cell migration. European Journal of Cell Biology. 2002; 81(6):313-321.
26. Bech-Serra J J, Santiago-Josefat B, Esselens C, Saftig P, Baselga J, Arribas J, et al. Proteomic Identification of Desmoglein 2 and Activated Leukocyte Cell Adhesion Molecule as Substrates of ADAM17 and ADAM10 by Difference Gel Electrophoresis. Molecular and Cellular Biology. 2006; 26(13):5086-5095.
27. Rosso O, Piazza T, Bongarzone I, Rossello A, Mezzanzanica D, Canevari S, et al. The ALCAM shedding by the metalloprotease ADAM17/TACE is involved in motility of ovarian carcinoma cells. Mol. Cancer Res. 2007; 5(12):1246-1253.

28. Piao D, Jiang T, Liu G, Wang B, Xu J, Zhu A. Clinical implications of activated leukocyte cell adhesion molecule expression in breast cancer. Mol Biol Rep. 2012; 39(1):661-668.

29. Zijlstra A. Proangiogenic role of neutrophil-like inflammatory heterophils during neovascularization induced by growth factors and human tumor cells. Blood. 2006; 107(1):317-327.

30. Carpenter A E, Jones T R, Lamprecht M R, Clarke C, Kang I H, Friman O, et al. CellProfiler: image analysis software for identifying and quantifying cell phenotypes. Genome Biol. 2006; 7(10):R100.

31. Lamprecht M, Sabatini D, Carpenter A. CellProfller™: free, versatile software for automated biological image analysis. BioTechniques. 2007; 42(1):71-75.

32. Uhlen M, Oksvold P, Fagerberg L, Lundberg E, Jonasson K, Forsberg M, et al. Towards a knowledge-based Human Protein Atlas. Nature Publishing Group. 2010; 28(12): 1248-1250.

33. Merchant N B, Voskresensky I, Rogers C M, LaFleur B, Dempsey P J, Graves-Deal R, et al. TACE/ADAM-17: A Component of the Epidermal Growth Factor Receptor Axis and a Promising Therapeutic Target in Colorectal Cancer. Clinical Cancer Research. 2008; 14(4):1182-1191.

34. Zhang T-C, Zhu W-G, Huang M-D, Fan R-H, Chen X-F. Prognostic value of ADAM17 in human gastric cancer. Med Oncol. 2011.

35. Smedbakken L, Jensen J K, Hallen J, Atar D, Januzzi J L, Halvorsen B, et al. Activated Leukocyte Cell Adhesion Molecule and Prognosis in Acute Ischemic Stroke. Stroke. 2011; 42(9):2453-2458.

36. Hollmén M, Määttä J A, Bald L, Sliwkowski M X, Elenius K. Suppression of breast cancer cell growth by a monoclonal antibody targeting cleavable ErbB4 isoforms. Oncogene. 2009; 28(10):1309-1319.

37. Kahlert C, Weber H, Mogler C, Bergmann F, Schirmacher P, Kenngott H G, et al. Increased expression of ALCAM/ CD166 in pancreatic cancer is an independent prognostic marker for poor survival and early tumour relapse. Br J Cancer. 2009; 101(3):457-464.

38. Ihnen M, Müller V, Wirtz R M, Schröder C, Krenkel S, Witzel I, et al. Predictive impact of activated leukocyte cell adhesion molecule (ALCAM/CD166) in breast cancer. Breast Cancer Res Treat. 2008; 112(3):419-427.

39. Minner S, Kraetzig F, Tachezy M, Kilic E, Graefen M, Wilczak W, et al. Low activated leukocyte cell adhesion molecule expression is associated with advanced tumor stage and early prostate-specific antigen relapse in prostate cancer. Hum. Pathol. 2011; 42(12):1946-1952.

40. Hong X, Michalski C W, Kong B, Zhang W, Raggi M C, Sauliunaite D, et al. ALCAM is associated with chemoresistance and tumor cell adhesion in pancreatic cancer. J Surg Oncol. 2010; 101(7):564-569.

41. Siegel R, Naishadham D, Jemal A. Cancer statistics, 2012. CA Cancer J Clin 2012; 62(1):10-29.

42. van Rhijn B W, Burger M, Lotan Y, et al. Recurrence and progression of disease in non-muscle-invasive bladder cancer: from epidemiology to treatment strategy. European urology 2009; 56(3):430-42.

43. Yafi F A, Aprikian A G, Fradet Y, et al. Surveillance guidelines based on recurrence patterns after radical cystectomy for bladder cancer: the Canadian Bladder Cancer Network experience. BJU Int. 2012; 110(9):1317-1323.

44. Botteman M F, Pashos C L, Redaelli A, et al. The health economics of bladder cancer: a comprehensive review of the published literature. PharmacoEconomics 2003; 21(18):1315-30.

45. Collaboration ABCAM-a. Neoadjuvant chemotherapy in invasive bladder cancer: update of a systematic review and meta-analysis of individual patient data advanced bladder cancer (ABC) meta-analysis collaboration. Eur. Urol. 2005; 48(2):202-5-discussion 205-6.

46. Raghavan D, Burgess E, Gaston K E, et al. Neoadjuvant and adjuvant chemotherapy approaches for invasive bladder cancer. In. *Semin. Oncol.;* 2012, 588-597.

47. Masedunskas A, King J A, Tan F, et al. Activated leukocyte cell adhesion molecule is a component of the endothelial junction involved in transendothelial monocyte migration. FEBS Left 2006; 580(11):2637-45.

48. Smith J R, Chipps T J, Ilias H, et al. Expression and regulation of activated leukocyte cell adhesion molecule in human retinal vascular endothelial cells. Exp. Eye Res. 2012; 104:89-93.

49. Abidi S M, Saifullah M K, Zafiropulos M D, et al. CD166 expression, characterization, and localization in salivary epithelium: implications for function during sialoadenitis. Journal of clinical immunology 2006; 26(1): 12-21.

50. Fraboulet S, Kavvadia K, Pourquie O, et al. BEN/D M-GRASP/SC1 expression during mouse facial development: differential expression and regulation in molars and incisors. Gene expression patterns: GEP 2003; 3(3):255-9.

51. Jannie K M, Stipp C S, Weiner J A. ALCAM regulates motility, invasiveness, and adherens junction formation in uveal melanoma cells. In. *PLoS ONE;* 2012, e39330.

52. Weidle U H, Eggle D, Klostermann S, et al. ALCAM/CD166: cancer-related issues. Cancer Genomics Proteomics 2010; 7(5):231-43.

53. Eissa S, Kassim S, El-Ahmady O. Detection of bladder tumours: role of cytology, morphology-based assays, biochemical and molecular markers. Curr. Opin. Obstet. Gynecol. 2003; 15(5):395-403.

54. Kim W-J, Bae S-C. Molecular biomarkers in urothelial bladder cancer. Cancer Sci. 2008; 99(4):646-652.

55. Carboni G, Orengo A M, Mezzanzanica D, et al. Activated leukocyte cell adhesion molecule soluble form: a potential biomarker of epithelial ovarian cancer is increased in type II tumors. Int. J. Cancer 2012.

56. Ihnen M, Kress K, Kersten J F, et al. Relevance of activated leukocyte cell adhesion molecule (ALCAM) in tumor tissue and sera of cervical cancer patients. BMC Cancer 2012; 12:140.

57. Tachezy M, Effenberger K, Zander H, et al. ALCAM (CD166) expression and serum levels are markers for poor survival of esophageal cancer patients. Int. J. Cancer 2012; 131(2):396-405.

58. Tachezy M, Zander H, Marx A H, et al. ALCAM (CD166) expression and serum levels in pancreatic cancer. PLoS ONE 2012; 7(6):e39018.

59. M, Taylor J M, Feifer A, et al. Combination of a novel gene expression signature with a clinical nomogram improves the prediction of survival in high-risk bladder cancer. Clin. Cancer Res. 2012; 18(5):1323-1333.

60. R A, Krahn K N, Megens R T, et al. High resolution imaging of collagen organisation and synthesis using a versatile collagen specific probe. Journal of structural biology 2007; 159(3):392-9.

61. Krahn K N, Bouten C V, van Tuijl S, et al. Fluorescently labeled collagen binding proteins allow specific visualization of collagen in tissues and live cell culture. Analytical biochemistry 2006; 350(2):177-85.
62. R_Development_Core_Team. R: A language and environment for statistical computing. In. Vienna, Austria: R Foundation for Statistical Computing; 2008.
63. Efron B, Tibshirani R. Improvements on cross-validation: The 0.632+ bootstrap method. Journal of the American Statistical Association 1997; 92(438):548-560.
64. Liang S, Huang C, Jia S, et al. Activated leukocyte cell adhesion molecule expression is up-regulated in the development of endometrioid carcinoma. Int. J. Gynecol. Cancer 2011; 21(3):523-528.
65. Verma A, Shukla N K, Deo S V S, et al. MEMD/ALCAM: a potential marker for tumor invasion and nodal metastasis in esophageal squamous cell carcinoma. Oncology 2005; 68(4-6):462-470.
66. Ihnen M, Wirtz R M, Kalogeras K T, et al. Combination of osteopontin and activated leukocyte cell adhesion molecule as potent prognostic discriminators in HER2- and ER-negative breast cancer. British journal of cancer 2010; 103(7):1048-56.
67. Ofori-Acquah S F, King J, Voelkel N, et al. Heterogeneity of barrier function in the lung reflects diversity in endothelial cell junctions. Microvasc Res 2008; 75(3): 391-402.
68. Lee J S, Leem S H, Lee S Y, et al. Expression signature of E2F1 and its associated genes predict superficial to invasive progression of bladder tumors. Journal of clinical oncology: official journal of the American Society of Clinical Oncology 2010; 28(16):2660-7.
69. Sanchez-Carbayo M, Socci N D, Lozano J, et al. Defining molecular profiles of poor outcome in patients with invasive bladder cancer using oligonucleotide microarrays. Journal of clinical oncology: official journal of the American Society of Clinical Oncology 2006; 24(5):778-89.
70. Rhodes D R, Kalyana-Sundaram S, Mahavisno V, et al. Oncomine 3.0: genes, pathways, and networks in a collection of 18,000 cancer gene expression profiles. Neoplasia 2007; 9(2):166-80.
71. Chaker S, Kak I, Macmillan C, et al. Activated leukocyte cell adhesion molecule (ALCAM/CD166) is a marker for thyroid cancer aggressiveness and disease-free survival. Thyroid 2012.
72. Ishiguro F, Murakami H, Mizuno T, et al. Membranous expression of activated leukocyte cell adhesion molecule contributes to poor prognosis and malignant phenotypes of non-small-cell lung cancer. J. Surg. Res. 2013; 179(1): 24-32.
73. Tachezy M, Zander H, Gebauer F, et al. Activated leukocyte cell adhesion molecule (CD166)—its prognostic power for colorectal cancer patients. J. Surg. Res. 2012; 177(1):e15-20.
74. Rodriguez Alonso A, Pita Fernandez S, Gonzalez-Carrero J, et al. [Multivariate analysis of recurrence and progression in stage T1 transitional-cell carcinoma of the bladder. Prognostic value of p53 and Ki67]. Actas urologicas espanolas 2003; 27(2):132-41.
75. Arai, A., Nosaka, Y., Kanda, E., Yamamoto, K., Miyasaka, N. and Miura, O. (2001). Rap1 is activated by erythropoietin or interleukin-3 and is involved in regulation of beta1 integrin-mediated hematopoietic cell adhesion. J Biol Chem 276, 10453-10462.
76. Aruffo, A., Bowen, M. A., Patel, D. D., Haynes, B. F., Starling, G. C., Gebe, J. A. and Bajorath, J. (1997). CD6-ligand interactions: a paradigm for SRCR domain function? Immunol Today 18, 498-504.
77. Ashby, W. J., Wikswo, J. P. and Zijlstra, A. (2012). Magnetically attachable stencils and the non-destructive analysis of the contribution made by the underlying matrix to cell migration. Biomaterials 33, 8189-8203.
78. Bailey, C. L., Kelly, P. and Casey, P. J. (2009). Activation of Rap1 promotes prostate cancer metastasis. Cancer Res 69, 4962-4968.
79. Bessard, A., Frémin, C., Ezan, F., Coutant, A. and Baffet, G. (2007). MEK/ERK-dependent uPAR expression is required for motility via phosphorylation of P70S6K in human hepatocarcinoma cells. J Cell Physiol 212, 526-536.
80. Bivona, T. G., Wiener, H. H., Ahearn, I. M., Silletti, J., Chiu, V. K. and Philips, M. R. (2004). Rap1 up-regulation and activation on plasma membrane regulates T cell adhesion. J Cell Biol 164, 461-470.
81. Boettner, B. and Van Aelst, L. (2009). Control of cell adhesion dynamics by Rap1 signaling. Curr Opin Cell Biol 21, 684-693.
82. Bos, J. L., de Rooij, J. and Reedquist, K. A. (2001). Rap1 signalling: adhering to new models. Nat Rev Mol Cell Biol 2, 369-377.
83. Buhusi, M., Demyanenko, G. P., Jannie, K. M., Dalal, J., Darnell, E. P. B., Weiner, J. A. and Maness, P. F. (2009). ALCAM regulates mediolateral retinotopic mapping in the superior colliculus. J Neurosci 29, 15630-15641.
84. Cherfils, J. and Zeghouf, M. (2013). Regulation of small GTPases by GEFs, GAPs, and GDIs. Physiol. Rev. 93, 269-309.
85. Chometon, G., Zhang, Z.-G., Rubinstein, E., Boucheix, C., Mauch, C. and Aumailley, M. (2006). Dissociation of the complex between CD151 and laminin-binding integrins permits migration of epithelial cells. Exp Cell Res 312, 983-995.
86. Copeland, B. T., Bowman, M. J. and Ashman, L. K. (2012). Genetic Ablation of the Tetraspanin Cd151 Reduces Spontaneous Metastatic Spread of Prostate Cancer in the TRAMP Model. Mol Cancer Res 11, 95-105.
87. Crawford, N. P. S., Ziogas, A., Peel, D. J., Hess, J., Anton-Culver, H. and Hunter, K. W. (2006). Germline polymorphisms in SIPA1 are associated with metastasis and other indicators of poor prognosis in breast cancer. Breast Cancer Res 8, R16.
88. Dedhar, S., Saulnier, R., Nagle, R. and Overall, C. M. (1993). Specific alterations in the expression of alpha 3 beta 1 and alpha 6 beta 4 integrins in highly invasive and metastatic variants of human prostate carcinoma cells selected by in vitro invasion through reconstituted basement membrane. Clin Exp Metastasis 11, 391-400.
89. Deng, X., Li, Q., Hoff, J., Novak, M., Yang, H., Jin, H., Erfani, S. F., Sharma, C., Zhou, P., Rabinovitz, I., et al. (2012). Integrin-associated CD151 drives ErbB2-evoked mammary tumor onset and metastasis. Neoplasia 14, 678-689.
90. Gebäck, T., Schulz, M. M. P., Koumoutsakos, P. and Detmar, M. (2009). TScratch: a novel and simple software tool for automated analysis of monolayer wound healing assays.
91. Gilsanz, A., Sanchez-Martin, L., Gutiérrez-López, M. D., Ovalle, S., Machado-Pineda, Y., Reyes, R., Swart, G. W., Figdor, C. G., Lafuente, E. M. and Cabañas, C. (2013). ALCAM/CD166 adhesive function is regulated by the tetraspanin CD9. Cell Mol Life Sci 70, 475-493.
92. Golub, T. R., Slonim, D. K., Tamayo, P., Huard, C., Gaasenbeek, M., Mesirov, J. P., Coller, H., Loh, M. L., Downing, J. R., Caligiuri, M. A., et al. (1999). Molecular classification of cancer: class discovery and class prediction by gene expression monitoring. Science 286, 531-537.
93. Han, J., Lim, C. J., Watanabe, N., Soriani, A., Ratnikov, B., Calderwood, D. A., Puzon-McLaughlin, W., Lafuente, E. M., Boussiotis, V. A., Shattil, S. J., et al. (2006). Reconstructing and deconstructing agonist-induced activation of integrin alphaIIbbeta3. Curr Biol 16, 1796-1806.
94. Hansen, A. G., Freeman, T. J., Arnold, S. A., Starchenko, A., jones-paris, C. R., Gilger, M. A., Washington, M. K., Fan, K.-H., Shyr, Y., Beauchamp, R. D., et al. (2013). Elevated ALCAM Shedding in Colorectal Cancer Correlates with Poor Patient Outcome. Cancer Res 73, 2955-2964.
95. Hemler, M. E. (2005). Tetraspanin functions and associated microdomains. Nat Rev Mol Cell Biol 6, 801-811.
96. Hemler, M. E. (2008). Targeting of tetraspanin proteins—potential benefits and strategies. Nature reviews Drug discovery 7, 747-758.
97. Hunter, K. W. (2003). Allelic diversity in the host genetic background may be an important determinant in tumor metastatic dissemination. Cancer Lett 200, 97-105.
98. Ikeyama, S., Koyama, M., Yamaoko, M., Sasada, R. and Miyake, M. (1993). Suppression of cell motility and metastasis by transfection with human motility-related protein (MRP-1/CD9) DNA. J Exp Med 177, 1231-1237.
99. Jeon, T. J., Lee, D.-J., Merlot, S., Weeks, G. and Firtel, R. A. (2007). Rap1 controls cell adhesion and cell motility through the regulation of myosin II. J Cell Biol 176, 1021-1033.
100. Johnson, J. L., Winterwood, N., DeMali, K. A. and Stipp, C. S. (2009). Tetraspanin CD151 regulates RhoA activation and the dynamic stability of carcinoma cell-cell contacts. J Cell Sci 122, 2263-2273.
101. King, J. A., Tan, F., Mbeunkui, F., Chambers, Z., Cantrell, S., Chen, H., Alvarez, D., Shevde, L. A. and Ofori-Acquah, S. F. (2010). Mechanisms of transcriptional regulation and prognostic significance of activated leukocyte cell adhesion molecule in cancer. Mol Cancer 9, 266.
102. Kitayama, H., Matsuzaki, T., Ikawa, Y. and Noda, M. (1990). Genetic analysis of the Kirsten-ras-revertant 1 gene: potentiation of its tumor suppressor activity by specific point mutations. Proc Natl Acad Sci USA 87, 4284-4288.
103. Kitayama, H., Sugimoto, Y., Matsuzaki, T., Ikawa, Y. and Noda, M. (1989). A ras-related gene with transformation suppressor activity. Cell 56, 77-84.
104. Kohno, M., Hasegawa, H., Miyake, M., Yamamoto, T. and Fujita, S. (2002). CD151 enhances cell motility and metastasis of cancer cells in the presence of focal adhesion kinase. Int J Cancer 97, 336-343.
105. Kooistra, M. R. H., Dubé, N. and Bos, J. L. (2007). Rap1: a key regulator in cell-cell junction formation. J Cell Sci 120, 17-22.
106. Lammerding, J., Kazarov, A. R., Huang, H., Lee, R. T. and Hemler, M. E. (2003). Tetraspanin CD151 regulates alpha6beta1 integrin adhesion strengthening. Proc Natl Acad Sci USA 100, 7616-7621.
107. Li, Q., Yang, X. H., Xu, F., Sharma, C., Wang, H.-X., Knoblich, K., Rabinovitz, I., Granter, S. R. and Hemler, M. E. (2012). Tetraspanin CD151 plays a key role in skin squamous cell carcinoma. Oncogene.
108. Lifsted, T., Le Voyer, T., Williams, M., Muller, W., Klein-Szanto, A., Buetow, K. H. and Hunter, K. W. (1998). Identification of inbred mouse strains harboring genetic modifiers of mammary tumor age of onset and metastatic progression. Int J Cancer 77, 640-644.
109. Liu, J. J., Stockton, R. A., Gingras, A. R., Ablooglu, A. J., Han, J., Bobkov, A. A. and Ginsberg, M. H. (2011). A mechanism of Rap1-induced stabilization of endothelial cell—cell junctions. Mol Biol Cell 22, 2509-2519.
110. Nishiuchi, R., Sanzen, N., Nada, S., Sumida, Y., Wada, Y., Okada, M., Takagi, J., Hasegawa, H. and Sekiguchi, K. (2005). Potentiation of the ligand-binding activity of integrin alpha3beta1 via association with tetraspanin CD151. Proc Natl Acad Sci USA 102, 1939-1944.
111. Ossowski, L., Russo, H., Gartner, M. and Wilson, E. L. (1987). Growth of a human carcinoma (HEp3) in nude mice: rapid and efficient metastasis. J Cell Physiol 133, 288-296.
112. Palmer, D. T. and Zijlstra, A. (2011). CD151. UCSD-Nature Molecule Pages.
113. Palmer, T. D., Ashby, W. J., Lewis, J. D. and Zijlstra, A. (2011a). Targeting tumor cell motility to prevent metastasis. Adv Drug Deliv Rev 63, 568-581.
114. Palmer, T. D., Lewis, J. and Zijlstra, A. (2011b). Quantitative analysis of cancer metastasis using an avian embryo model. J Vis Exp.
115. Palmer, T. D., Martinez, C. H., Vasquez, C., Hebron, K. E., jones-paris, C. R., Arnold, S. A., Chan, S. M., Chalasani, V., gomez-lemus, J. A., Williams, A. K., et al. Integrin-free tetraspanin CD151 can inhibit tumor cell motility upon clustering and is a clinical indicator of prostate cancer progression. Cancer Res Submitted.
116. Partin, A. W., Schoeniger, J. S., Mohler, J. L. and Coffey, D. S. (1989). Fourier analysis of cell motility: correlation of motility with metastatic potential. Proc Natl Acad Sci USA 86, 1254-1258.
117. Price, L. S., Hajdo-Milasinovic, A., Zhao, J., Zwartkruis, F. J. T., Collard, J. G. and Bos, J. L. (2004). Rap1 regulates E-cadherin-mediated cell-cell adhesion. J Biol Chem 279, 35127-35132.
118. Radford, K. J., Thorne, R. F. and Hersey, P. (1997). Regulation of tumor cell motility and migration by CD63 in a human melanoma cell line. J Immunol 158, 3353-3358.
119. Reedquist, K. A., Ross, E., Koop, E. A., Wolthuis, R. M., Zwartkruis, F. J., van Kooyk, Y., Salmon, M., Buckley, C. D. and Bos, J. L. (2000). The small GTPase, Rap1, mediates CD31-induced integrin adhesion. J Cell Biol 148, 1151-1158.
120. Ross, S. H., Spanjaard, E., Post, A., Vliem, M. J., Kristyanto, H., Bos, J. L. and de Rooij, J. (2012). Rap1 can bypass the FAK-Src-Paxillin cascade to induce cell spreading and focal adhesion formation. PLoS ONE 7, e50072.
121. Rubinstein, E., Charrin, S. and Tomlinson, M. G. (2013). Organisation of the Tetraspanin Web. 47-90.
122. Silletti, S., Yebra, M., Perez, B., Cirulli, V., McMahon, M. and Montgomery, A. M. P. (2004). Extracellular signal-regulated kinase (ERK)-dependent gene expression contributes to L1 cell adhesion molecule-dependent motility and invasion. J Biol Chem 279, 28880-28888.
123. Simpson, K. J., Selfors, L. M., Bui, J., Reynolds, A., Leake, D., Khvorova, A. and Brugge, J. S. (2008). Identification of genes that regulate epithelial cell migration using an siRNA screening approach. Nat Cell Biol 10, 1027-1038.
124. Takeda, Y., Li, Q., Kazarov, A. R., Epardaud, M., Elpek, K., Turley, S. J. and Hemler, M. E. (2011). Diminished metastasis in tetraspanin CD151-knockout mice. Blood 118, 464-472.

125. Takino, J., Nagamine, K. and Hori, T. (2013). Ras guanyl nucleotide releasing protein 2 affects cell viability and cell-matrix adhesion in ECV304 endothelial cells. Cell Adh Migr 7.

126. Testa, J. E., Brooks, P. C., Lin, J. M. and Quigley, J. P. (1999). Eukaryotic expression cloning with an antimetastatic monoclonal antibody identifies a tetraspanin (PETA-3/CD151) as an effector of human tumor cell migration and metastasis. Cancer Res 59, 3812-3820.

127. van Kilsdonk, J. W. J., Takahashi, N., Weidle, U., Burtscher, H., Jarry, J., Daha, M. R., Swart, G. W. M. and van Kempen, L. C. L. T. (2012). Modulation of activated leukocyte cell adhesion molecule-mediated invasion triggers an innate immune gene response in melanoma. J Invest Dermatol 132, 1462-1470.

128. Varzavand, A., Drake, J. M., Svensson, R. U., Herndon, M. E., Zhou, B., Henry, M. D. and Stipp, C. S. (2013). Integrin α3β1 regulates tumor cell responses to stromal cells and can function to suppress prostate cancer metastatic colonization. Clin Exp Metastasis 30, 541-552.

129. Winterwood, N. E., Varzavand, A., Meland, M. N., Ashman, L. K. and Stipp, C. S. (2006). A critical role for tetraspanin CD151 in alpha3beta1 and alpha6beta4 integrin-dependent tumor cell functions on laminin-5. Mol Biol Cell 17, 2707-2721.

130. Yang, Y.-M., Zhang, Z.-W., Liu, Q.-M., Sun, Y.-F., Yu, J.-R. and Xu, W.-X. (2013). Overexpression of CD151 Predicts Prognosis in Patients with Resected Gastric Cancer. PLoS ONE 8, e58990.

131. Yauch, R. L. and Hemler, M. E. (2000). Specific interactions among transmembrane 4 superfamily (TM4SF) proteins and phosphoinositide 4-kinase. Biochem J 351 Pt 3, 629-637.

132. Yauch, R. L., Berditchevski, F., Harler, M. B., Reichner, J. and Hemler, M. E. (1998). Highly stoichiometric, stable, and specific association of integrin alpha3beta1 with CD151 provides a major link to phosphatidylinositol 4-kinase, and may regulate cell migration. Mol Biol Cell 9, 2751-2765.

133. Yunta, M. and Lazo, P. A. (2003). Tetraspanin proteins as organisers of membrane microdomains and signalling complexes. 15, 559-564.

134. Zhang, B., Kirov, S. and Snoddy, J. (2005). WebGestalt: an integrated system for exploring gene sets in various biological contexts. Nucleic Acids Res 33, W741-8.

135. Zhang, X. A., Bontrager, A. L. and Hemler, M. E. (2001). Transmembrane-4 superfamily proteins associate with activated protein kinase C (PKC) and link PKC to specific beta(1) integrins. J Biol Chem 276, 25005-25013.

136. Zijlstra, A. (2010). Tetraspanins in Cancer. Cell-Extracellular Matrix Interactions in Cancer.

137. Zijlstra, A., Lewis, J., Degryse, B., Stuhlmann, H. and Quigley, J. P. (2008). The inhibition of tumor cell intravasation and subsequent metastasis via regulation of in vivo tumor cell motility by the tetraspanin CD151. Cancer Cell 13, 221-234.

138. Zimmerman, A. W., Nelissen, J. M. D. T., van Emst-de Vries, S. E., Willems, P. H. G. M., de Lange, F., Collard, J. G., van Leeuwen, F. N. and Figdor, C. G. (2004). Cytoskeletal restraints regulate homotypic ALCAM-mediated adhesion through PKCalpha independently of Rho-like GTPases. J Cell Sci 117, 2841-2852.

139. Zöller, M. (2010). Tetraspanins and Cancer Metastasis. The Tumor Microenvironment.

140. Mundy G R. Metastasis to bone: causes, consequences and therapeutic opportunities. Nat Rev Cancer. 2002; 2:584-93.

141. Pound C R, Partin A W, Eisenberger M A, Chan D W, Pearson J D, Walsh P C. Natural history of progression after PSA elevation following radical prostatectomy. JAMA. 1999; 281:1591-7.

142. Jin J-K, Dayyani F, Gallick G E. Steps in prostate cancer progression that lead to bone metastasis. Int J Cancer. 2011; 128:2545-61.

143. van Kempen L C, Nelissen J M, Degen W G, Torensma R, Weidle U H, Bloemers H P, et al. Molecular basis for the homophilic activated leukocyte cell adhesion molecule (ALCAM)-ALCAM interaction. J Biol Chem. 2001; 276:25783-90.

144. Pokutta S, Weis W I. Structure and mechanism of cadherins and catenins in cell-cell contacts. Annu Rev Cell Dev Biol. 2007; 23:237-61.

145. King J A, Ofori-Acquah S F, Stevens T, Al-Mehdi A-B, Fodstad O, Jiang W G. Activated leukocyte cell adhesion molecule in breast cancer: prognostic indicator. Breast Cancer Res. 2004; 6:R478-87.

146. Lunter P C, van Kilsdonk J W J, van Beek H, Cornelissen I M H A, Bergers M, Willems P H G M, et al. Activated leukocyte cell adhesion molecule (ALCAM/CD166/MEMD), a novel actor in invasive growth, controls matrix metalloproteinase activity. Cancer Res. 2005; 65:8801-8.

147. Li H, Jiang M, Honorio S, Patrawala L, Jeter C R, Calhoun-Davis T, et al. Methodologies in assaying prostate cancer stem cells. Methods Mol Biol. 2009; 568:85-138.

148. Park S I, Kim S-J, McCauley L K, Gallick G E. Pre-clinical mouse models of human prostate cancer and their utility in drug discovery. Curr Protoc Pharmacol. 2010; Chapter 14:Unit 14.15.

149. Varambally S, Yu J, Laxman B, Rhodes D R, Mehra R, Tomlins S A, et al. Integrative genomic and proteomic analysis of prostate cancer reveals signatures of metastatic progression. Cancer Cell. 2005; 8:393-406.

150. Nakagawa T, KollmeyerT M, Morlan B W, Anderson S K, Bergstralh E J, Davis B J, et al. A Tissue Biomarker Panel Predicting Systemic Progression after PSA Recurrence Post-Definitive Prostate Cancer Therapy. PLoS ONE. Public Library of Science; 2008; 3:e2318.

151. Kim W, Ahn H J, Zelner D J, Shaw J W, Sensibar J A, Kim J H, et al. Genetic change in transforming growth factor beta (TGF-beta) receptor type I gene correlates with insensitivity to TGF-beta 1 in human prostate cancer cells. Cancer Res. 1996; 56:44-8.

152. Wang S E, Xiang B, Guix M, Olivares M G, Parker J, Chung C H, et al. Transforming growth factor beta engages TACE and ErbB3 to activate phosphatidylinositol-3 kinase/Akt in ErbB2-overexpressing breast cancer and desensitizes cells to trastuzumab. Mol Cell Biol. 2008; 28:5605-20.

153. Soond S M, Everson B, Riches D W H, Murphy G. ERK-mediated phosphorylation of Thr735 in TNFalpha-converting enzyme and its potential role in TACE protein trafficking. J Cell Sci. 2005; 118:2371-80.

154. Ott G R, Asakawa N, Lu Z, Anand R, Liu R-Q, Covington M B, et al. Potent, exceptionally selective, orally bioavailable inhibitors of TNF-alpha Converting Enzyme (TACE): novel 2-substituted-1H-benzo[d]imidazol-1-yl)methyl)benzamide P1' substituents. Bioorganic & Medicinal Chemistry Letters. 2008; 18:1577-82.

155. Wang Y, Xue H, Cutz J-C, Bayani J, Mawji N R, Chen W G, et al. An orthotopic metastatic prostate cancer model in SCID mice via grafting of a transplantable human prostate tumor line. Lab Invest. 2005; 85:1392-404.

156. Ofori-Acquah S F, King J A. Activated leukocyte cell adhesion molecule: a new paradox in cancer. Translational research: the journal of laboratory and clinical medicine. 2008; 151:122-8.
157. Karan D, Lin F C, Bryan M, Ringel J, Moniaux N, Lin M-F, et al. Expression of ADAMs (a disintegrin and metalloproteases) and TIMP-3 (tissue inhibitor of metalloproteinase-3) in human prostatic adenocarcinomas. Int J Oncol. 2003; 23:1365-71.
158. Jezierska A, Matysiak W, Motyl T. ALCAM/CD166 protects breast cancer cells against apoptosis and autophagy. Med Sci Monit. 2006; 12:BR263-73.
159. Buijs J T, Que I, Löwik C W G M, Papapoulos S E, van der Pluijm G. Inhibition of bone resorption and growth of breast cancer in the bone microenvironment. Bone. 2009; 44:380-6.
160. Zijlstra A. Tetraspanins in Cancer. Cell-Extracellular Matrix Interactions in Cancer. 2010.
161. Wang H X, Li Q, Sharma C, Knoblich K, Hemler M E. Tetraspanin protein contributions to cancer. Biochem Soc Trans. 2011; 39:547-52.
162. Hong I-K, Jin Y-J, Byun H-J, Jeoung D-I, Kim Y-M, Lee H. Homophilic interactions of Tetraspanin CD151 up-regulate motility and matrix metalloproteinase-9 expression of human melanoma cells through adhesion-dependent c-Jun activation signaling pathways. J Biol Chem. 2006; 281:24279-92.
163. Stipp C S, Kolesnikova T V, Hemler M E. EWI-2 is a major CD9 and CD81 partner and member of a novel Ig protein subfamily. J Biol Chem. 2001; 276:40545-54.
164. Yáñez-Mó M, Barreiro O, Gonzalo P, Batista A, Megias D, Genis L, et al. MT1-MMP collagenolytic activity is regulated through association with tetraspanin CD151 in primary endothelial cells. Blood. 2008; 112:3217-26.
165. Kazarov A R, Yang X, Stipp C S, Sehgal B, Hemler M E. An extracellular site on tetraspanin CD151 determines alpha 3 and alpha 6 integrin-dependent cellular morphology. J Cell Biol. 2002; 158:1299-309.
166. Novitskaya V, Romanska H, Dawoud M, Jones J L, Berditchevski F. Tetraspanin CD151 regulates growth of mammary epithelial cells in three-dimensional extracellular matrix: implication for mammary ductal carcinoma in situ. Cancer Res. 2010; 70:4698-708.
167. Yang X H, Flores L M, Li Q, Zhou P, Xu F, Krop I E, et al. Disruption of laminin-integrin-CD151-focal adhesion kinase axis sensitizes breast cancer cells to ErbB2 antagonists. Cancer Res. 2010; 70:2256-63.
168. Lau L-M, Wee J L, Wright M D, Moseley G W, Hogarth P M, Ashman L K, et al. The tetraspanin superfamily member CD151 regulates outside-in integrin alphaIIbbeta3 signaling and platelet function. Blood. 2004; 104:2368-75.
169. Sachs N, Kreft M, van den Bergh Weerman M A, Beynon A J, Peters T A, Weening J J, et al. Kidney failure in mice lacking the tetraspanin CD151. J Cell Biol. 2006; 175:33-9.
170. Berditchevski F, Gilbert E, Griffiths M R, Fitter S, Ashman L, Jenner S J. Analysis of the CD151-alpha3beta1 integrin and CD151-tetraspanin interactions by mutagenesis. J Biol Chem. 2001; 276:41165-74.
171. Zhang X A, Kazarov A R, Yang X, Bontrager A L, Stipp C S, Hemler M E. Function of the tetraspanin CD151-alpha6beta1 integrin complex during cellular morphogenesis. Mol Biol Cell. 2002; 13:1-11.
172. Yamada M, Tamura Y, Sanzen N, Sato-Nishiuchi R, Hasegawa H, Ashman L K, et al. Probing the interaction of tetraspanin CD151 with integrin alpha 3 beta 1 using a panel of monoclonal antibodies with distinct reactivities toward the CD151-integrin alpha 3 beta 1 complex. Biochem J. 2008; 415:417-27.
173. Haeuw J F, Goetsch L, Bailly C, Corvaia N. Tetraspanin CD151 as a target for antibody-based cancer immunotherapy. Biochem Soc Trans. 2011; 39:553-8.
174. Serra V, Le Naour F, Billard M, Azorsa D O, Lanza F, Boucheix C, et al. Selective tetraspan-integrin complexes (CD81/alpha4beta1, CD151/alpha3beta1, CD151/alpha6beta1) under conditions disrupting tetraspan interactions. Biochem J [Internet]. 1999; 340 (Pt 1):103-11.
175. Geary S M, Cambareri A C, Sincock P M, Fitter S, Ashman L K. Differential tissue expression of epitopes of the tetraspanin CD151 recognised by monoclonal antibodies. Tissue Antigens. 2001; 58:141-53.
176. Sterk L M T, Geuijen C A W, van den Berg J G, Claessen N, Weening J J, Sonnenberg A. Association of the tetraspanin CD151 with the laminin-binding integrins alpha3beta1, alpha6beta1, alpha6beta4 and alpha7beta1 in cells in culture and in vivo. 2002; 115:1161-73.
177. Ossowski L, Reich E. Changes in malignant phenotype of a human carcinoma conditioned by growth environment. Cell. 1983; 33:323-33.
178. Marjoram R J, Voss B, Pan Y, Dickeson S K, Zutter M M, (null), et al. Suboptimal activation of protease-activated receptors enhances alpha2beta1 integrin-mediated platelet adhesion to collagen. J. Biol. Chem. 2009; 284:34640-7.
179. Cerami E, Gao J, Dogrusoz U, Gross B E, Sumer S O, Aksoy B A, et al. The cBio Cancer Genomics Portal: An Open Platform for Exploring Multidimensional Cancer Genomics Data. Cancer Discovery. 2012; 2:401-4.
180. Chandran U R, Ma C, Dhir R, Bisceglia M, Lyons-Weiler M, Liang W, et al. Gene expression profiles of prostate cancer reveal involvement of multiple molecular pathways in the metastatic process. 2007; 7:21.
181. Tomlins S A, Mehra R, Rhodes D R, Cao X, Wang L, Dhanasekaran S M, et al. Integrative molecular concept modeling of prostate cancer progression. Nat Genet. 2007; 39:41-51.
182. Taylor B S, Schultz N, Hieronymus H, Gopalan A, Xiao Y, Carver B S, et al. Integrative genomic profiling of human prostate cancer. Cancer Cell. 2010; 18:11-22.
183. Derso Z, Nikolsky Y, Sviridov E, Shi W, Serebriyskaya T, Dosymbekov D, et al. A comprehensive functional analysis of tissue specificity of human gene expression. BMC Biol. 2008; 6:49.
184. Fogerty F J, Akiyama S K, Yamada K M, Mosher D F. Inhibition of binding of fibronectin to matrix assembly sites by anti-integrin (alpha 5 beta 1) antibodies. J Cell Biol. 1990; 111:699-708.
185. Offermanns S. Activation of platelet function through G protein-coupled receptors. Circ Res. 2006; 99:1293-304.
186. Nishiuchi R, Murayama O, Fujiwara H, Gu J, Kawakami T, Aimoto S, et al. Characterization of the ligand-binding specificities of integrin alpha3beta1 and alpha6beta1 using a panel of purified laminin isoforms containing distinct alpha chains. J Biochem. 2003; 134:497-504.
187. Yang X H, Richardson A L, Torres-Arzayus M I, Zhou P, Sharma C, Kazarov A R, et al. CD151 accelerates breast cancer by regulating alpha 6 integrin function, signaling, and molecular organization. Cancer Res. 2008; 68:3204-13.
188. Liu L, He B, Liu W M, Zhou D, Cox T V, Zhang X A. Tetraspanin CD151 promotes cell migration by regulating integrin trafficking. J Biol Chem. 2007; 282:31631-42.

189. Ke H, Wang P, Yu W, Liu X, Liu C, Yang F, et al. Derivation, characterization and gene modification of cynomolgus monkey mesenchymal stem cells. Differentiation. 2009; 77:256-62.
190. Tsujino K, Takeda Y, Arai T, Shintani Y, Inagaki R, Saiga H, et al. Tetraspanin CD151 protects against pulmonary fibrosis by maintaining epithelial integrity. Am J Respir Crit Care Med. 2012; 186:170-80.
191. Palecek S P, Loftus J C, Ginsberg M H, Lauffenburger D A, Horwitz A F. Integrin-ligand binding properties govern cell migration speed through cell-substratum adhesiveness. Nature. 1997; 385:537-40.
192. Sachs N, Sonnenberg A. Cell-matrix adhesion of podocytes in physiology and disease. Nat Rev Nephrol. Nature Publishing Group; 2013; 9:200-10.

What is claimed is:

1. A method for detecting an amount of shed ALCAM, intact ALCAM, and total ALCAM in a biological sample from a subject, comprising:
   (a) obtaining or having obtained the sample from the subject;
      (i) contacting the sample with one or more antibodies for each of intracellular ALCAM and extracellular ALCAM;
      (ii) detecting an amount of shed ALCAM in the sample by identifying, through the one or more antibodies, a portion of the sample that includes the intracellular domain of ALCAM and lacks the extracellular domain of ALCAM;
      (iii) detecting an amount of intact ALCAM in the sample by identifying, through the one or more antibodies, a portion of the sample that includes the intracellular domain of ALCAM and also includes the extracellular domain of ALCAM; and
      (iv) determining the total ALCAM in the sample by calculating the sum of the portion of the sample including shed ALCAM and the portion of the sample including intact ALCAM; and
   (b) obtaining or having obtained a second tissue sample from the subject at a time point after the first sample is obtained;
      (i) contacting the second sample with one or more antibodies for each of intracellular ALCAM and extracellular ALCAM;
      (ii) detecting an amount of shed ALCAM in the second sample by identifying, through the one or more antibodies, a portion of the sample that includes the intracellular domain of ALCAM and lacks the extracellular domain of ALCAM;
      (iii) detecting an amount of intact ALCAM in the second sample by identifying, through the one or more antibodies, a portion of the sample that includes the intracellular domain of ALCAM and also includes the extracellular domain of ALCAM; and
      (iv) determining the total ALCAM in the second sample by calculating the sum of the portion of the sample including shed ALCAM and the portion of the sample including intact ALCAM.

2. The method of claim 1, and further comprising determining whether there is an increase or decrease in the area of shed ALCAM.

3. The method of claim 1, and further comprising calculating a ratio of intact ALCAM to shed ALCAM.

* * * * *

UNITED STATES PATENT AND TRADEMARK OFFICE
CERTIFICATE OF CORRECTION

PATENT NO. : 10,585,102 B2
APPLICATION NO. : 14/433519
DATED : March 10, 2020
INVENTOR(S) : Zijlstra et al.

It is certified that error appears in the above-identified patent and that said Letters Patent is hereby corrected as shown below:

In the Specification

Replace the second paragraph, which appears on Column 1, with the following:
Government Interest
This invention was made with government support under grant numbers CA120711, CA143081, CA040035, TR000445, CA136228, CA009592, CA098131, HL007751, and DK079341 awarded by the National Institutes of Health. The government has certain rights in the invention.

Signed and Sealed this
Seventeenth Day of September, 2024

Katherine Kelly Vidal
*Director of the United States Patent and Trademark Office*